(12) United States Patent
Whayne et al.

(10) Patent No.: US 7,837,681 B2
(45) Date of Patent: Nov. 23, 2010

(54) STRUCTURES FOR SUPPORTING MULTIPLE ELECTRODE ELEMENTS

(75) Inventors: James G Whayne, Saratoga, CA (US); Sidney D Fleischman, Menlo Park, CA (US); Russell B Thompson, Los Altos, CA (US); David K Swanson, Mountain View, CA (US); Yi Yang, San Francisco, CA (US)

(73) Assignee: EP Technologies, Inc., San Jose, CA (US)

( * ) Notice: Subject to any disclaimer, the term of this patent is extended or adjusted under 35 U.S.C. 154(b) by 1268 days.

(21) Appl. No.: 11/278,569

(22) Filed: Apr. 4, 2006

(65) Prior Publication Data

US 2006/0189975 A1 Aug. 24, 2006

Related U.S. Application Data

(63) Continuation of application No. 10/112,407, filed on Mar. 29, 2002, now Pat. No. 7,025,766, which is a continuation of application No. 09/523,685, filed on Mar. 13, 2000, now Pat. No. 6,402,746, which is a continuation of application No. 08/771,217, filed on Dec. 19, 1996, now Pat. No. 6,071,279.

(51) Int. Cl.
*A61B 18/14* (2006.01)
(52) U.S. Cl. .......................... 606/41; 606/47
(58) Field of Classification Search ............ 606/41, 606/45–50
See application file for complete search history.

(56) References Cited

U.S. PATENT DOCUMENTS

| | | | |
|---|---|---|---|
| 1,207,479 A | 12/1916 | Bisgaard | |
| 4,033,331 A | 7/1977 | Guss et al. | |
| 4,181,131 A | 1/1980 | Ogiu | |
| 4,245,624 A | 1/1981 | Komiya | |
| 4,753,223 A | 6/1988 | Bremer | |
| 4,826,087 A | 5/1989 | Chinery | |
| 5,041,085 A | 8/1991 | Osbourne | |
| 5,098,412 A | 3/1992 | Shiu | |
| 5,156,151 A | 10/1992 | Imran | |
| 5,263,493 A | 11/1993 | Avitall | |
| 5,273,535 A | 12/1993 | Edwards | |
| 5,284,473 A | 2/1994 | Calabria | |
| 5,306,245 A | 4/1994 | Heavan | |
| 5,327,905 A | 7/1994 | Avitall | |

(Continued)

FOREIGN PATENT DOCUMENTS

DE 3920707 A1 1/1991

(Continued)

*Primary Examiner*—Michael Peffley
(74) *Attorney, Agent, or Firm*—Henricks, Slavin & Holmes LLP

(57) ABSTRACT

A catheter assembly comprises a first branch body having a first axis, a second branch body extending in a non-parallel relationship with respect to the first axis, and at least one electrode carried by the second branch body. In use, the first branch body can be located within a pulmonary vein within the left atrium, while the electrode carried by the second branch body is located in contact with endocardial tissue outside the pulmonary vein. Ablation energy can be transmitted from the electrode to contacted endocardial tissue while the first branch body is located within the pulmonary vein.

17 Claims, 34 Drawing Sheets

U.S. PATENT DOCUMENTS

| | | | |
|---|---|---|---|
| 5,330,518 A | 7/1994 | Neilson et al. | |
| 5,354,296 A * | 10/1994 | Turkel | 606/41 |
| 5,366,490 A | 11/1994 | Edwards et al. | |
| 5,368,592 A | 11/1994 | Stern | |
| 5,370,675 A | 12/1994 | Edwards | |
| 5,399,165 A | 3/1995 | Paul, Jr. | |
| 5,415,656 A | 5/1995 | Tihon et al. | |
| 5,437,665 A * | 8/1995 | Munro | 606/47 |
| 5,439,006 A | 8/1995 | Brennen | |
| 5,482,037 A | 1/1996 | Borghi | |
| 5,487,385 A | 1/1996 | Avitall | |
| 5,487,757 A | 1/1996 | Truckai | |
| 5,500,012 A | 3/1996 | Brucker | |
| 5,549,661 A | 8/1996 | Kordis | |
| 5,571,088 A | 11/1996 | Lennox | |
| 5,637,090 A | 6/1997 | McGee | |
| 5,672,174 A | 9/1997 | Gough | |
| 5,702,368 A | 12/1997 | Stevens | |
| 5,702,438 A | 12/1997 | Avitall | |
| 5,709,224 A | 1/1998 | Behl | |
| 5,730,127 A | 3/1998 | Avitall | |
| 5,738,683 A | 4/1998 | Osypka | |
| 5,741,249 A | 4/1998 | Moss | |
| 5,775,327 A | 7/1998 | Randolph et al. | |
| 5,782,899 A | 7/1998 | Imran | |
| 5,800,482 A | 9/1998 | Pomeranz | |
| 5,800,484 A | 9/1998 | Gough | |
| 5,820,591 A | 10/1998 | Thompson | |
| 5,836,947 A | 11/1998 | Fleischman | |
| 5,863,291 A | 1/1999 | Schaer | |
| 5,865,800 A | 2/1999 | Mirarchi | |
| 5,879,295 A | 3/1999 | Li | |
| 5,895,417 A | 4/1999 | Pomeranz | |
| 5,910,129 A | 6/1999 | Koblish | |
| 5,931,811 A | 8/1999 | Haissaguerre | |
| 5,938,660 A | 8/1999 | Swartz | |
| 5,971,983 A * | 10/1999 | Lesh | 606/41 |
| 6,012,457 A | 1/2000 | Lesh | |
| 6,013,052 A | 1/2000 | Durman | |
| 6,016,811 A | 1/2000 | Knopp | |
| 6,027,473 A | 2/2000 | Ponzi | |
| 6,048,329 A | 4/2000 | Thompson | |
| 6,050,993 A * | 4/2000 | Tu et al. | 606/41 |
| 6,064,902 A | 5/2000 | Haissaguerre | |
| 6,068,629 A | 5/2000 | Haissaguerre | |
| 6,071,274 A | 6/2000 | Thompson | |
| 6,071,279 A | 6/2000 | Whayne | |
| 6,076,012 A | 6/2000 | Swanson | |
| 6,120,500 A | 9/2000 | Bednarek | |
| 6,200,315 B1 | 3/2001 | Gaiser | |
| 6,203,525 B1 | 3/2001 | Whayne | |
| 6,237,605 B1 | 5/2001 | Vaska | |
| 6,290,699 B1 * | 9/2001 | Hall et al. | 606/41 |
| 6,311,692 B1 | 11/2001 | Vaska | |
| 6,314,962 B1 | 11/2001 | Vaska | |
| 6,314,963 B1 | 11/2001 | Vaska | |
| 6,332,880 B1 | 12/2001 | Yang | |
| 6,402,746 B1 | 6/2002 | Whayne | |
| 6,413,234 B1 | 7/2002 | Thompson | |
| 6,454,758 B1 | 9/2002 | Thompson | |
| 6,464,700 B1 | 10/2002 | Koblish | |
| 6,527,769 B2 * | 3/2003 | Langberg et al. | 606/41 |
| 6,607,505 B1 | 8/2003 | Thompson | |
| 6,758,830 B1 * | 7/2004 | Schaer et al. | 604/95.04 |
| 7,025,766 B2 | 4/2006 | Whayne | |
| 7,029,471 B2 | 4/2006 | Thompson | |

FOREIGN PATENT DOCUMENTS

| | | |
|---|---|---|
| EP | 0238106 A1 | 9/1987 |
| EP | 0737487 A2 | 10/1996 |
| EP | 0868922 A2 | 10/1998 |
| EP | 0916360 A2 | 5/1999 |
| WO | WO-95/10253 A1 | 4/1995 |
| WO | WO-95/10322 A1 | 4/1995 |
| WO | WO-95/15115 A1 | 6/1995 |
| WO | WO-97/37607 A2 | 10/1997 |
| WO | WO-97/42996 A1 | 11/1997 |
| WO | WO-98/26724 A1 | 6/1998 |
| WO | WO-99/18878 A2 | 4/1999 |

* cited by examiner

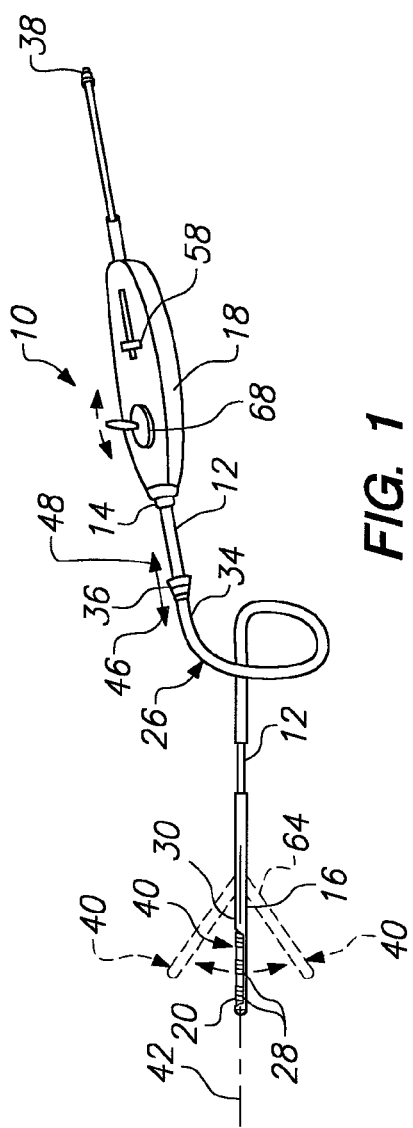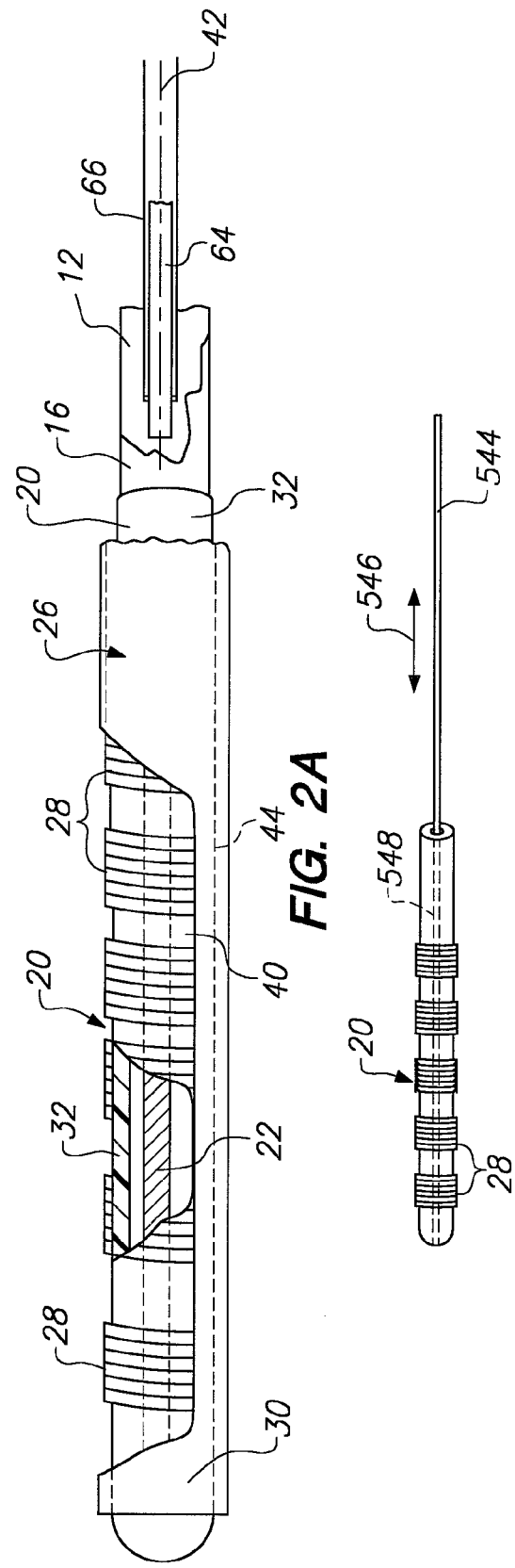

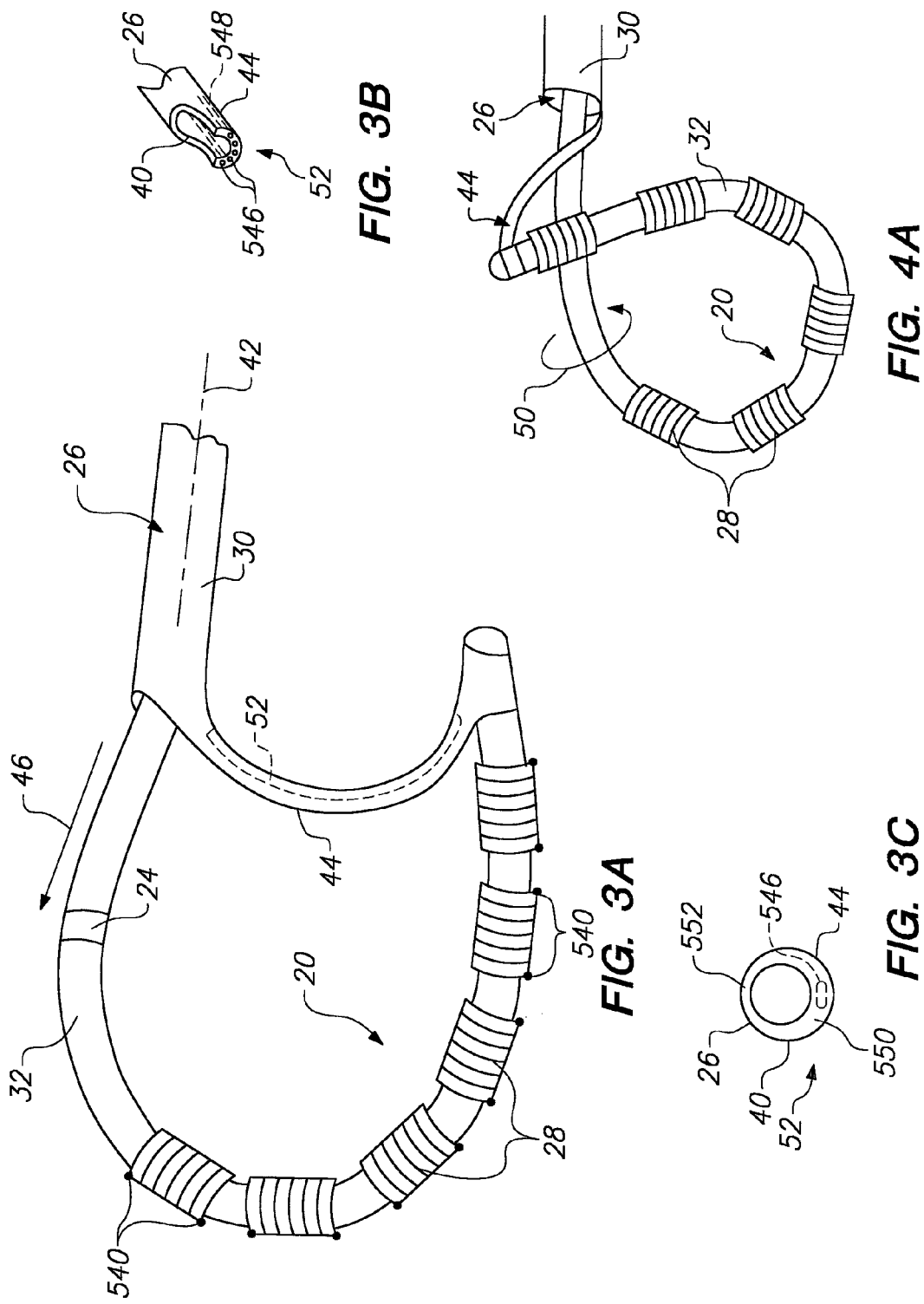

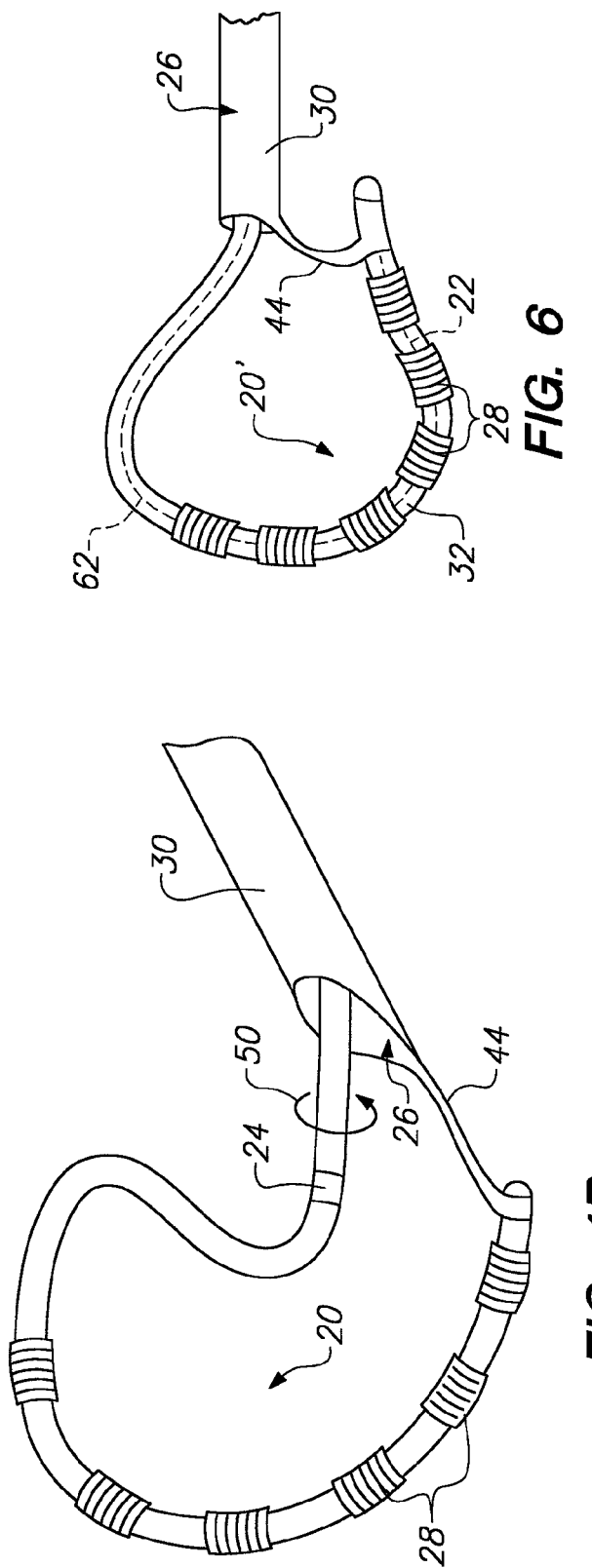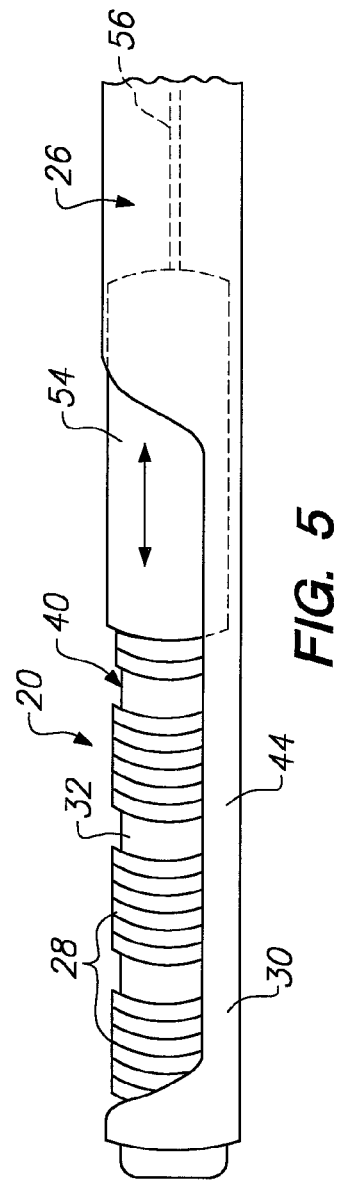

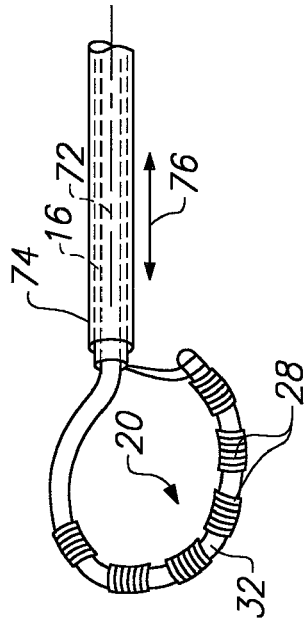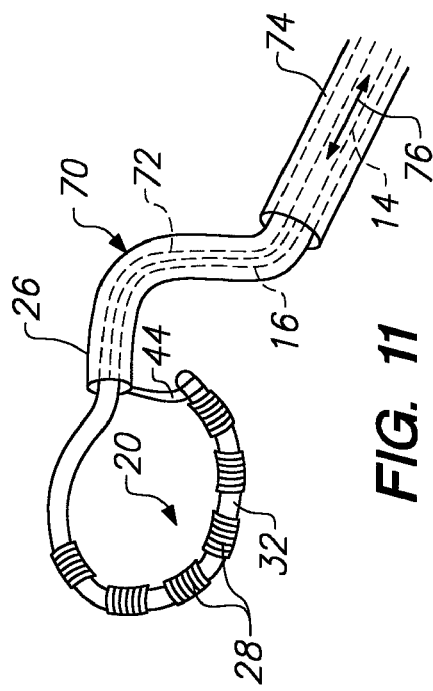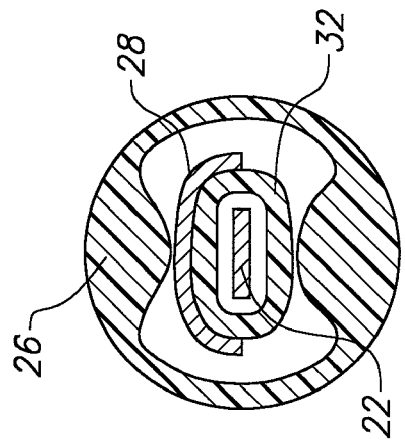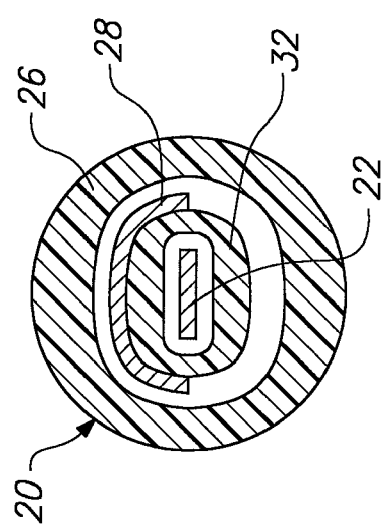

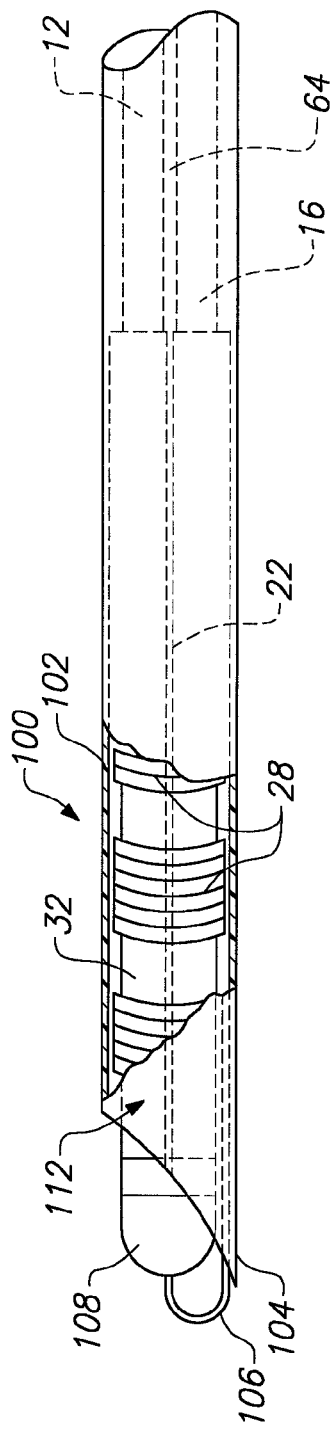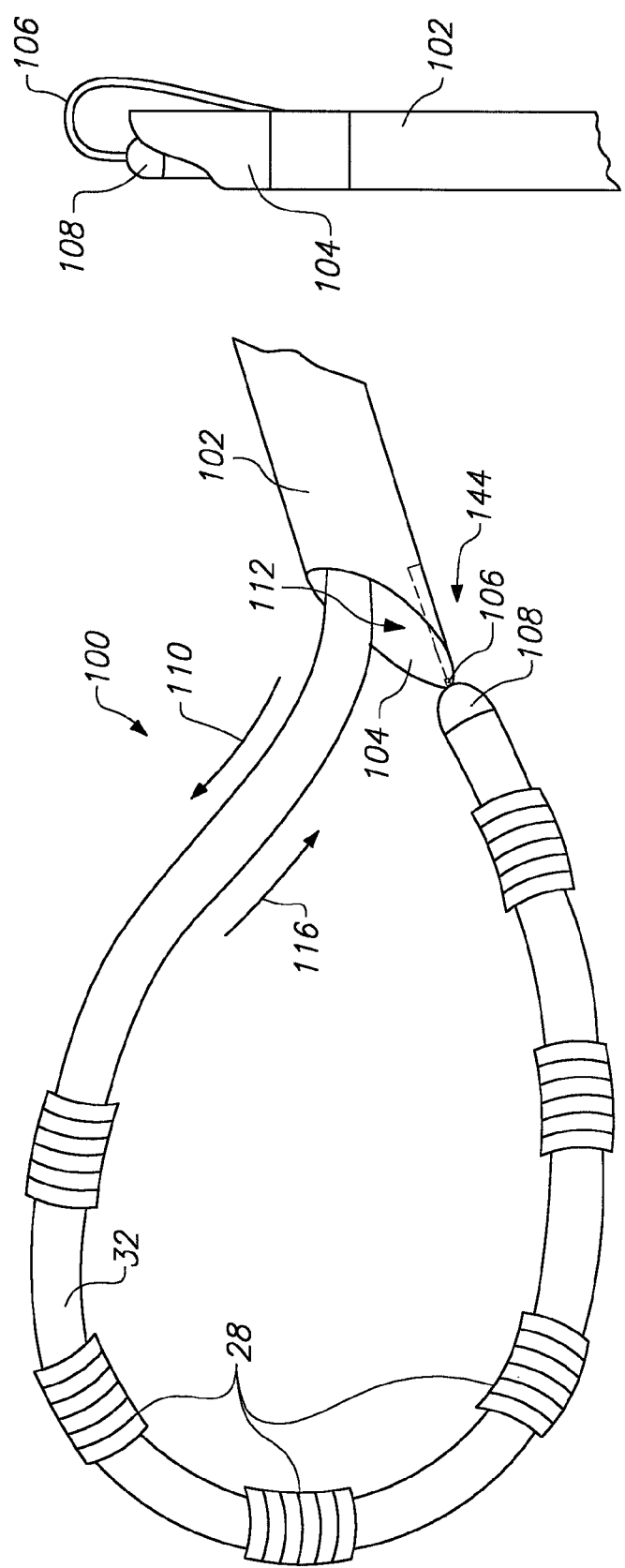

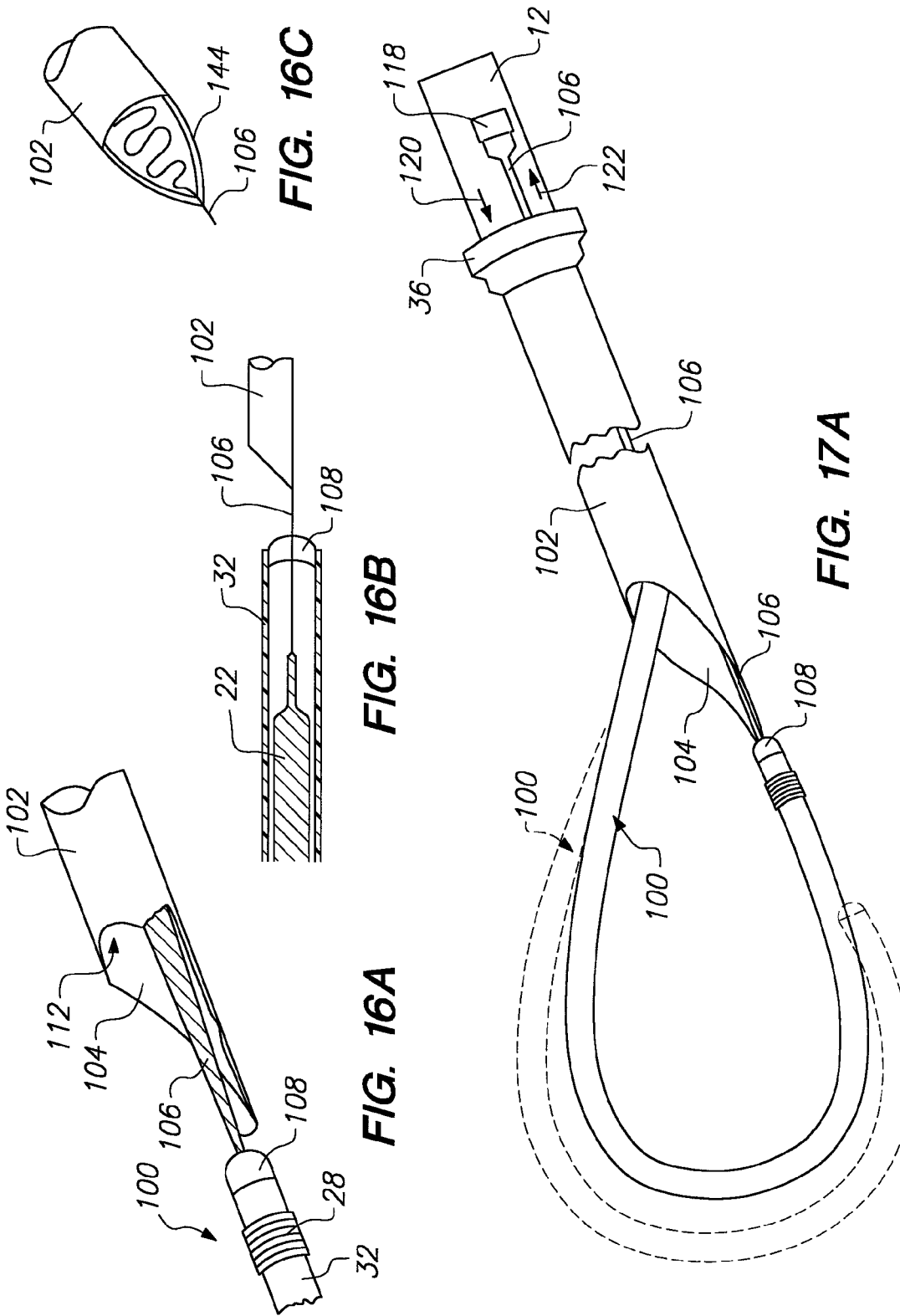

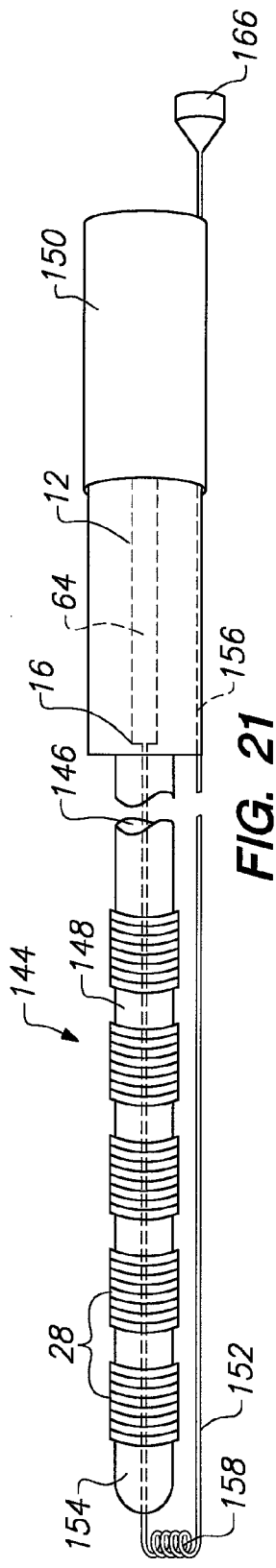
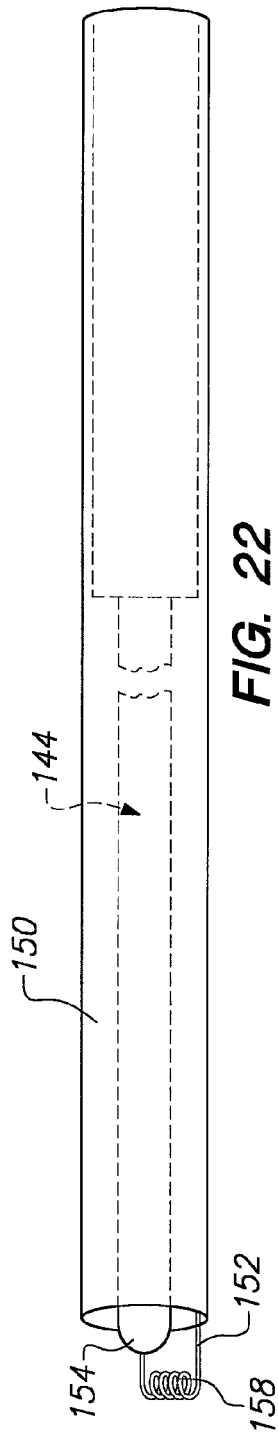
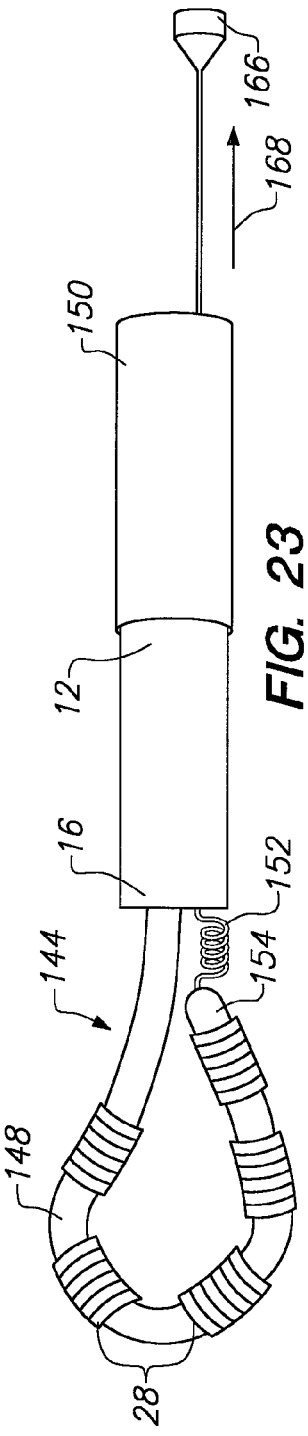
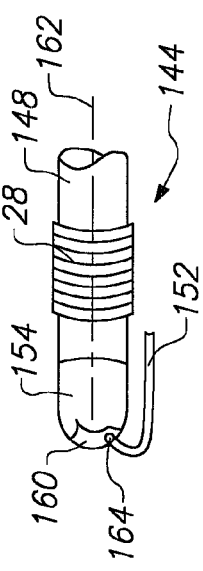
FIG. 21
FIG. 22
FIG. 23
FIG. 24

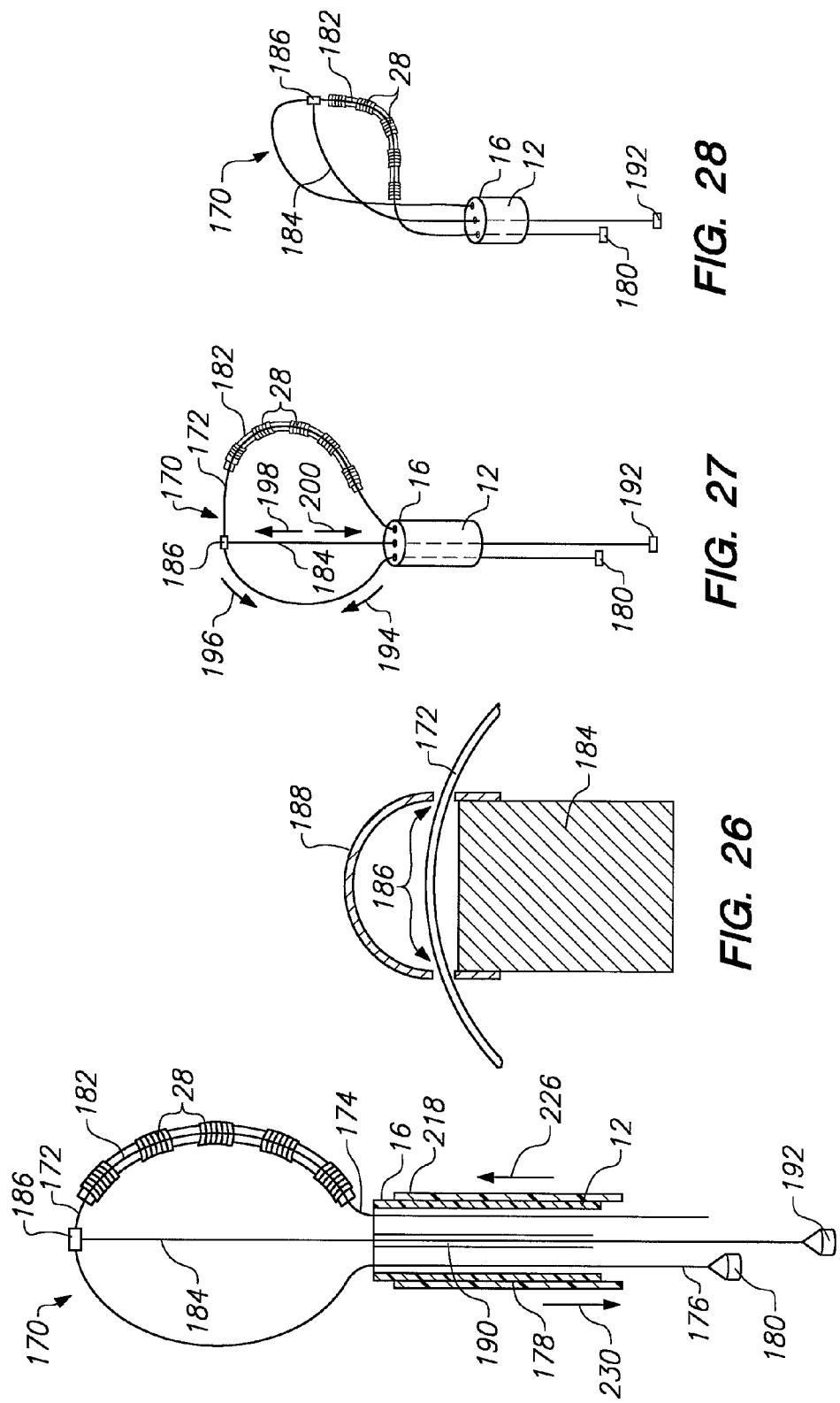

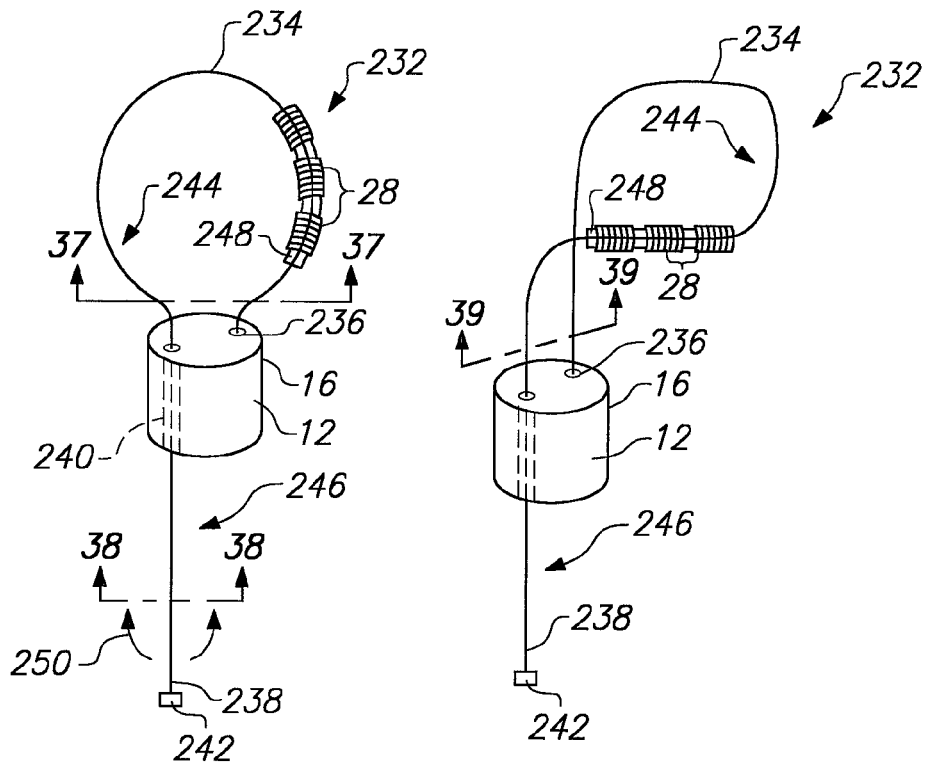
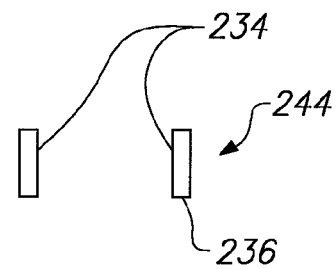
FIG. 35
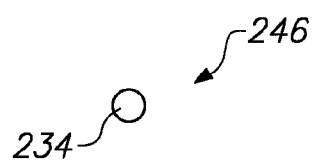
FIG. 36
FIG. 37
FIG. 38
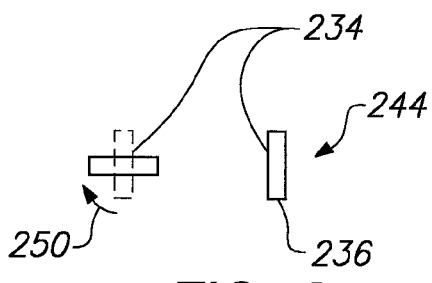
FIG. 39

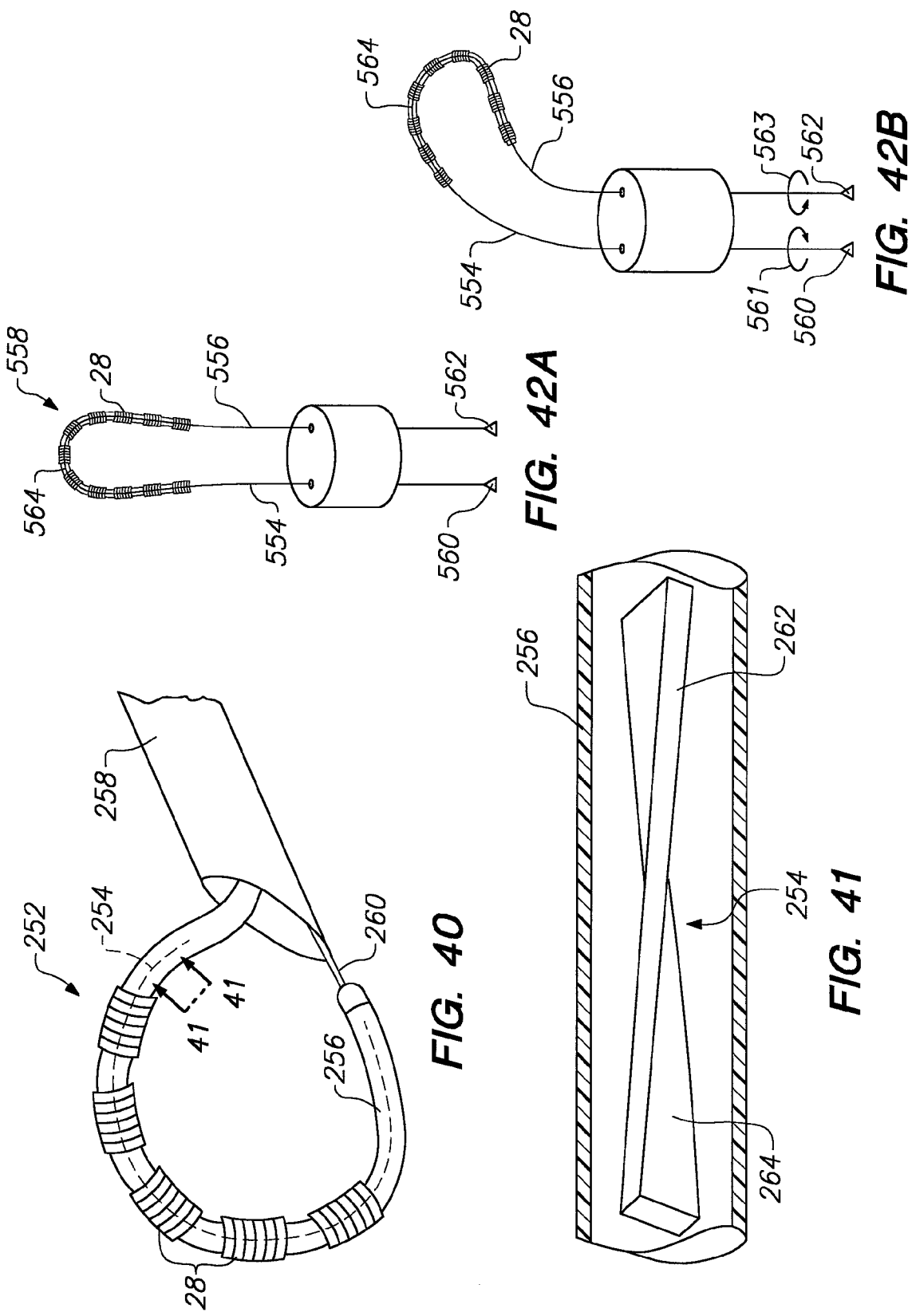

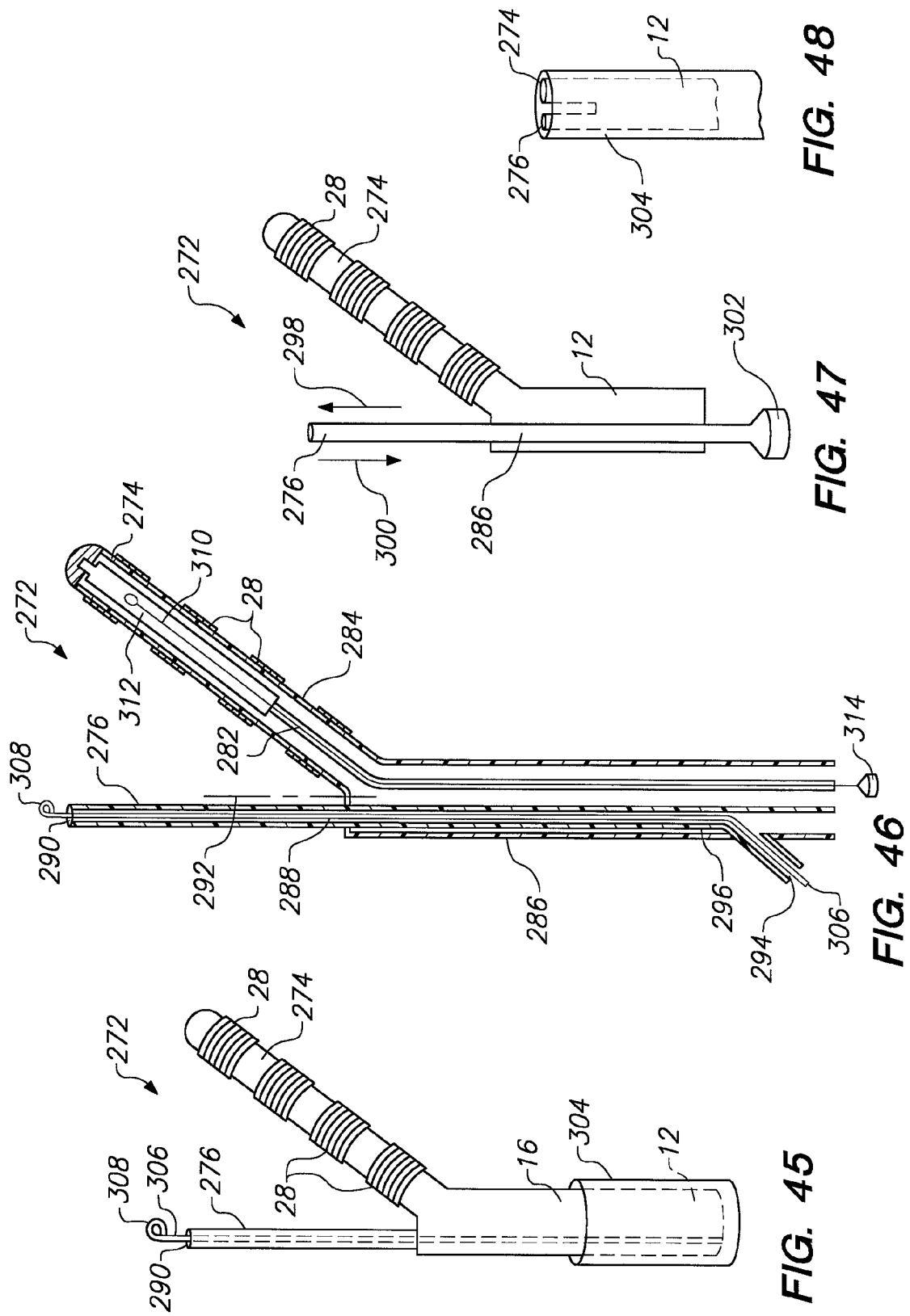

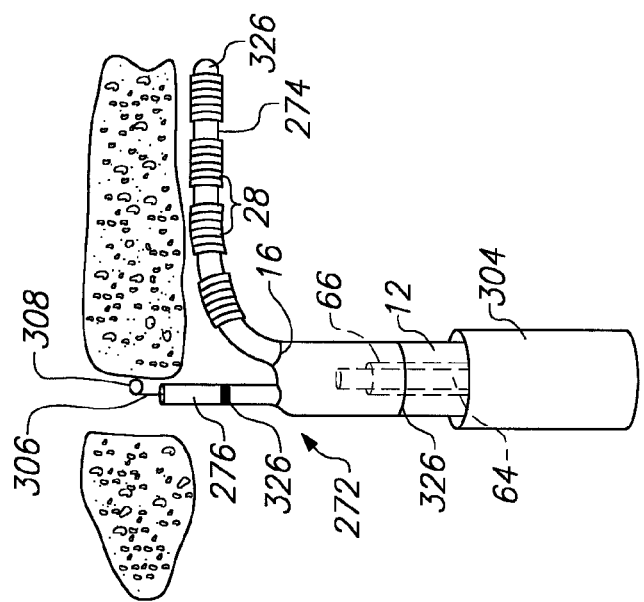
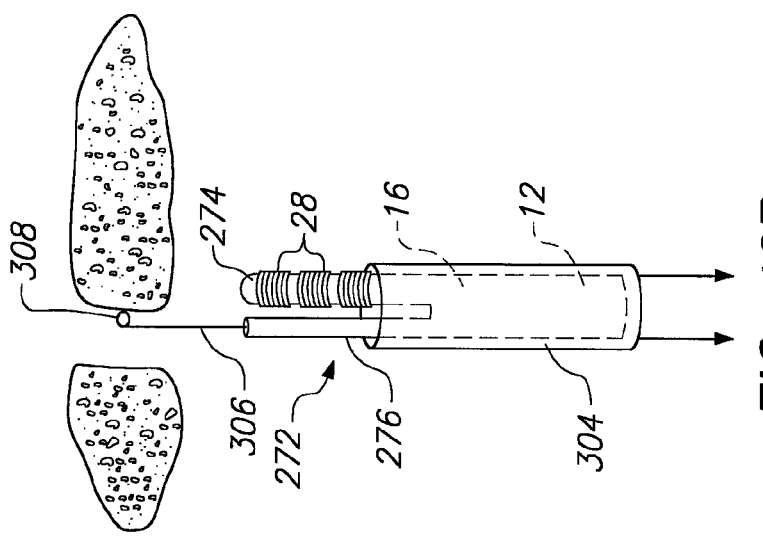
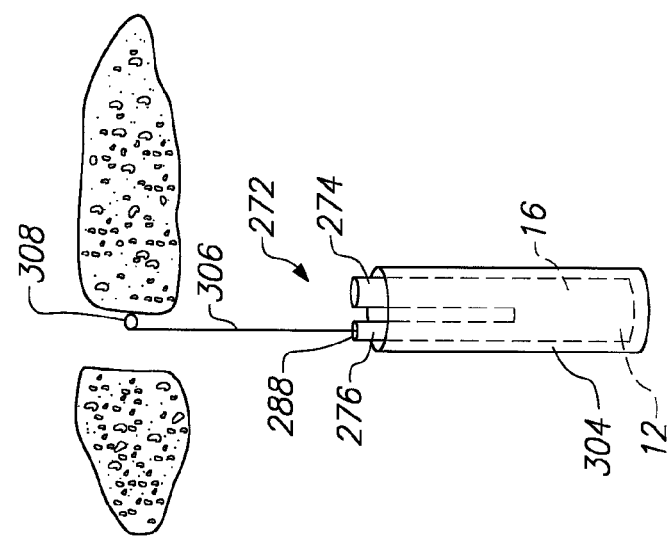

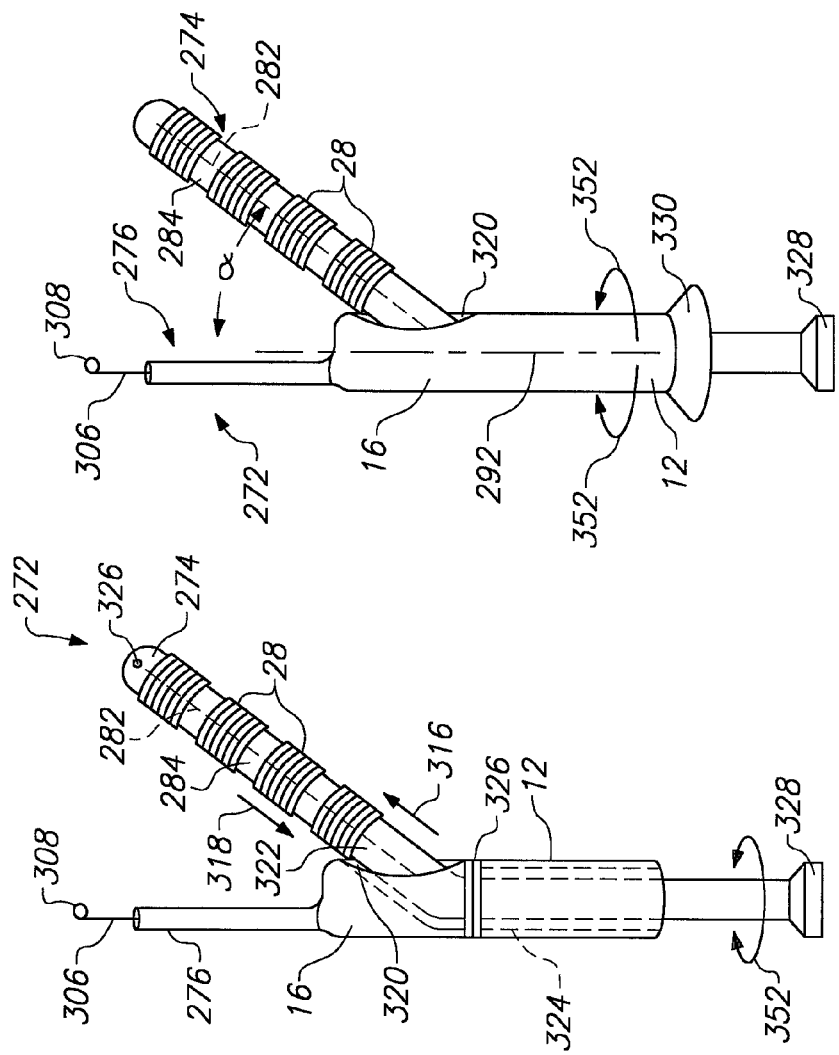
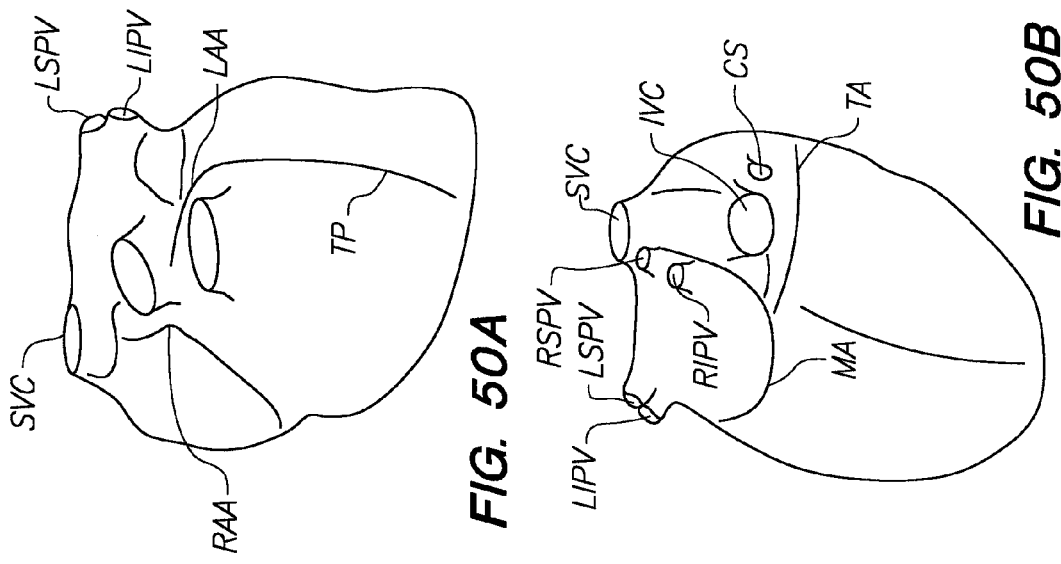
FIG. 50A
FIG. 50B
FIG. 51
FIG. 52

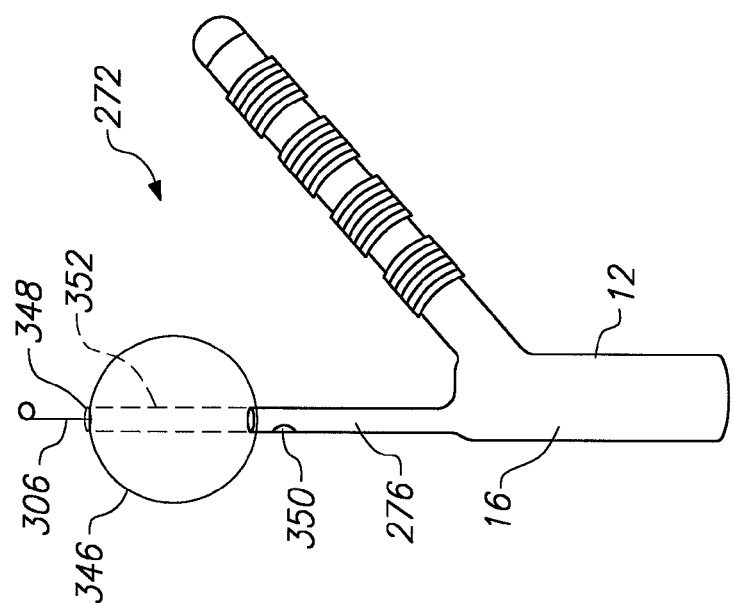
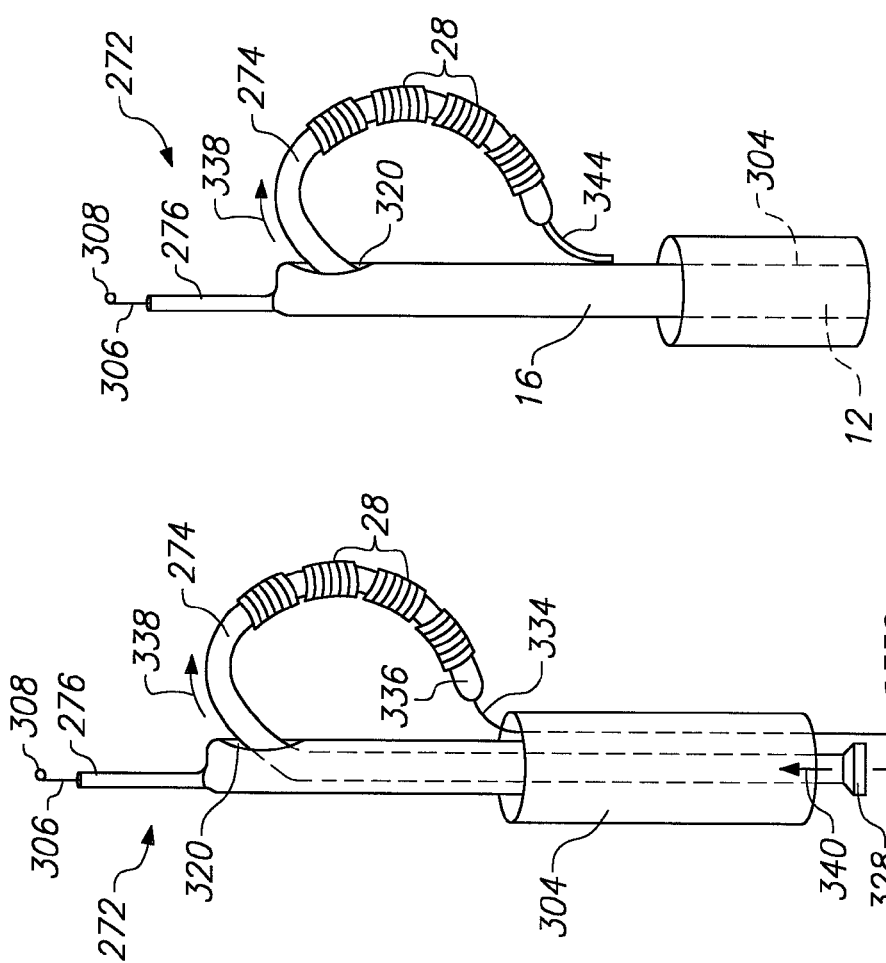
FIG. 55
FIG. 54
FIG. 53

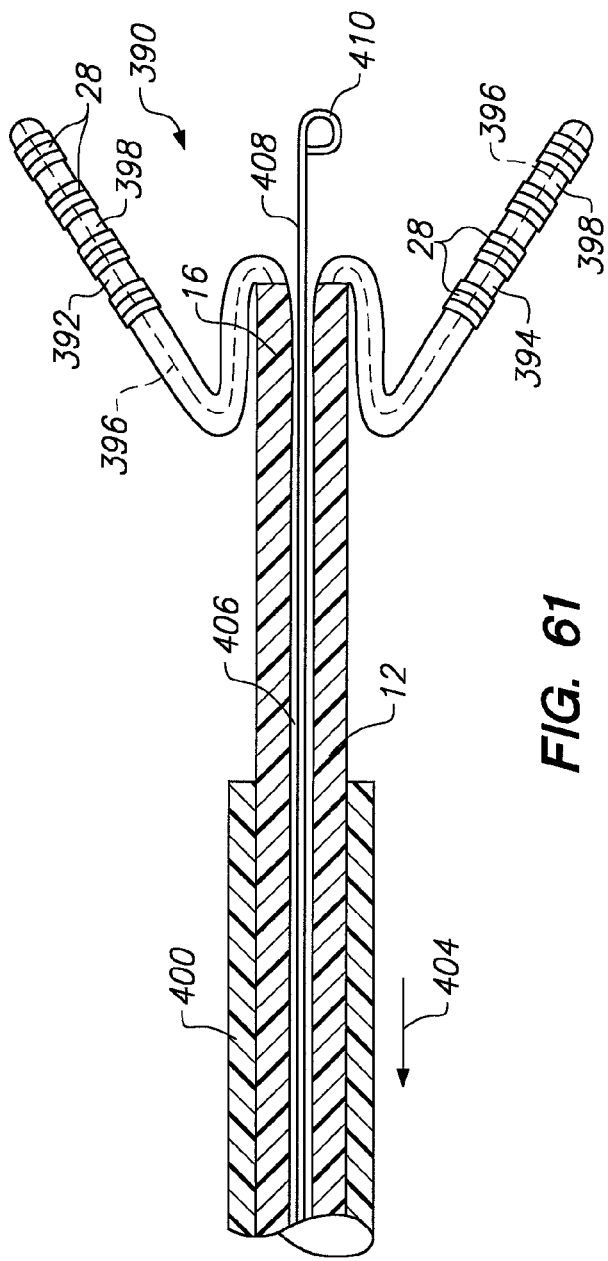
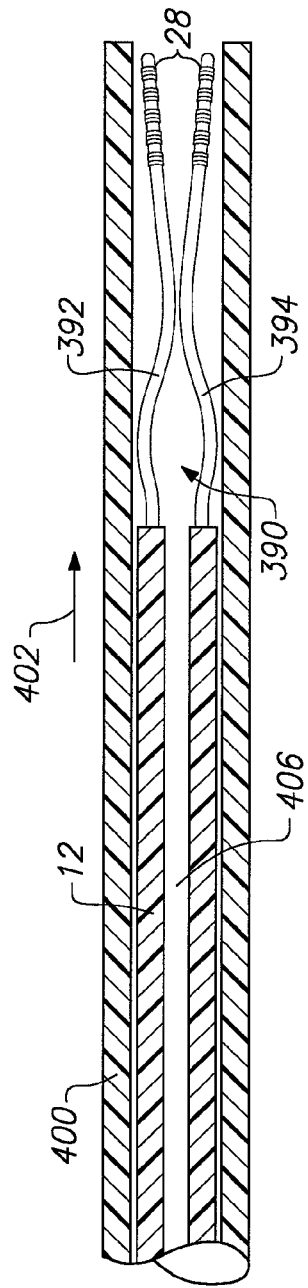
FIG. 61
FIG. 62

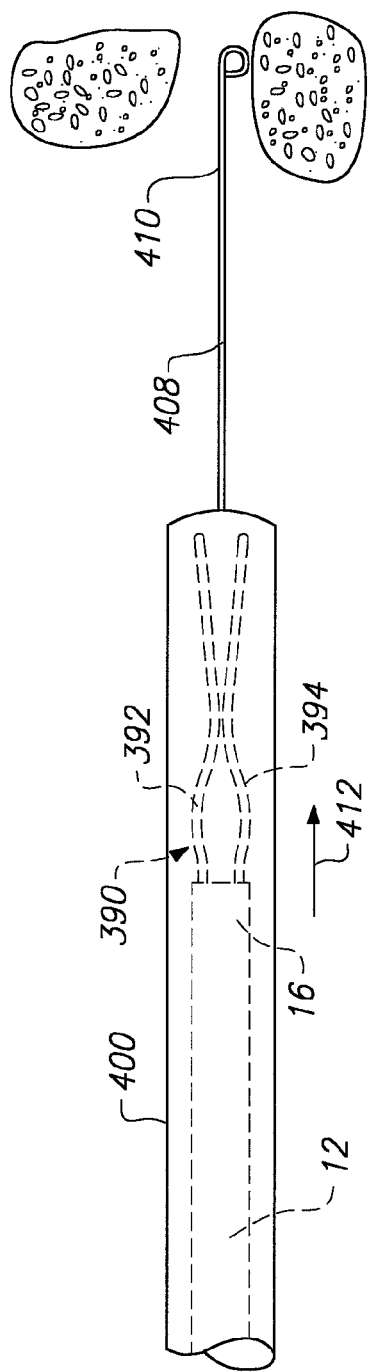
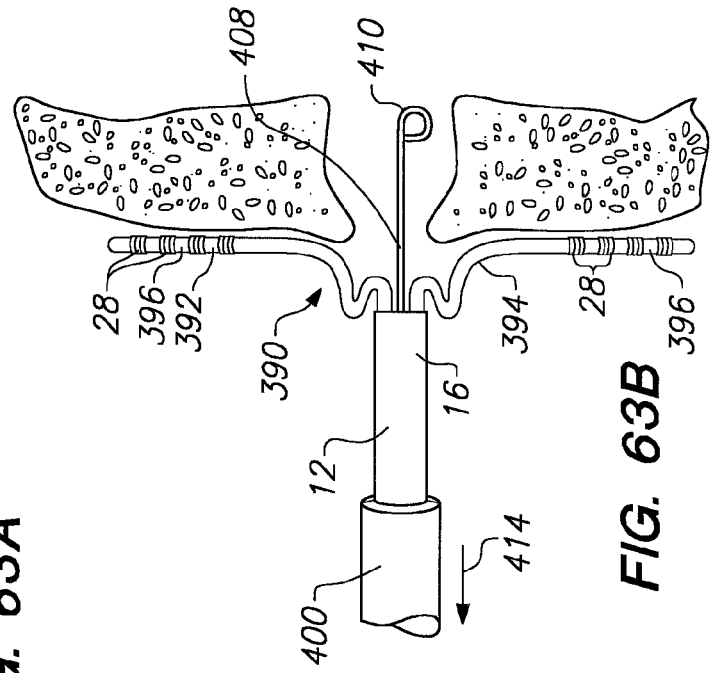
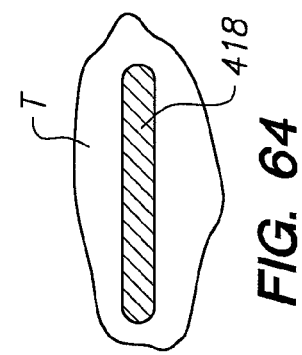
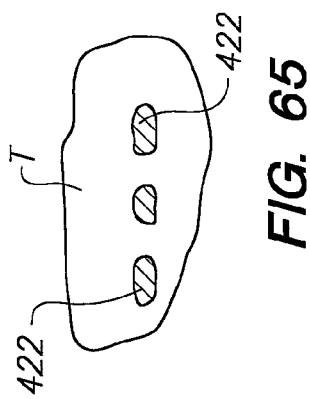
FIG. 63A
FIG. 63B
FIG. 64
FIG. 65

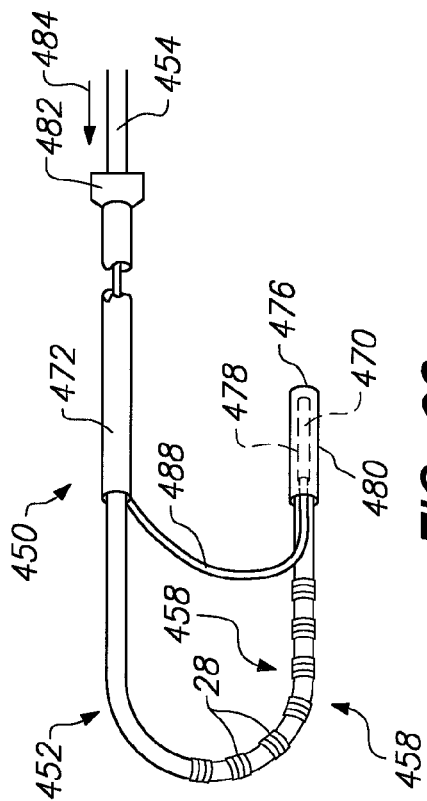
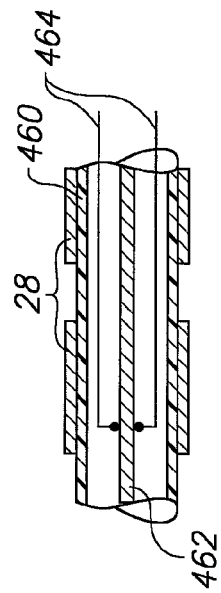
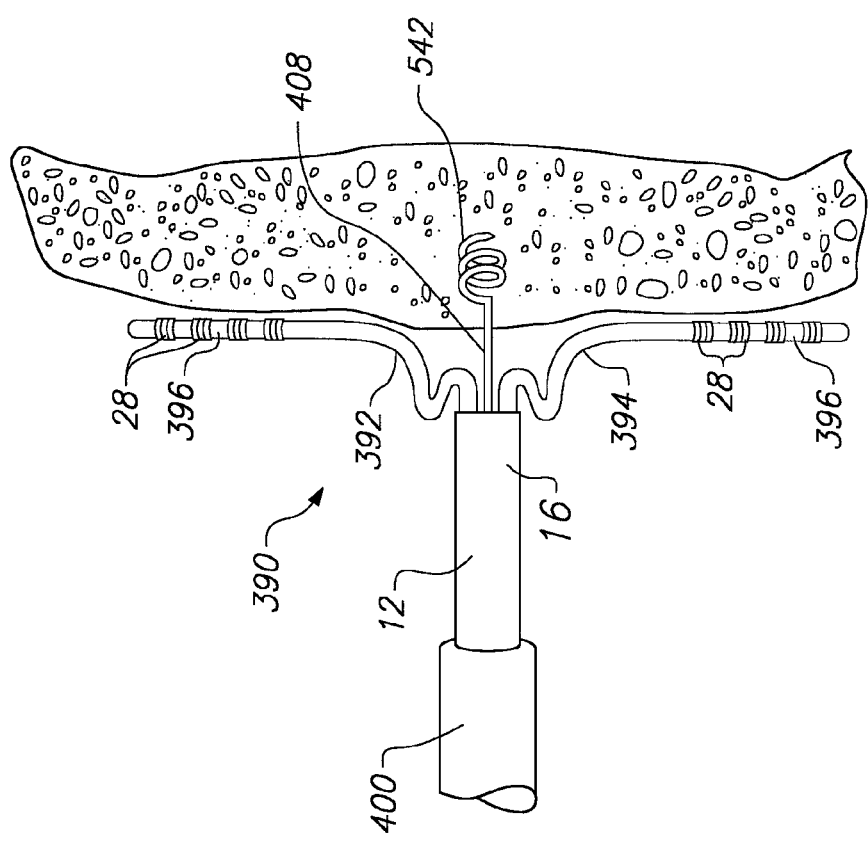
FIG. 68
FIG. 69
FIG. 63C

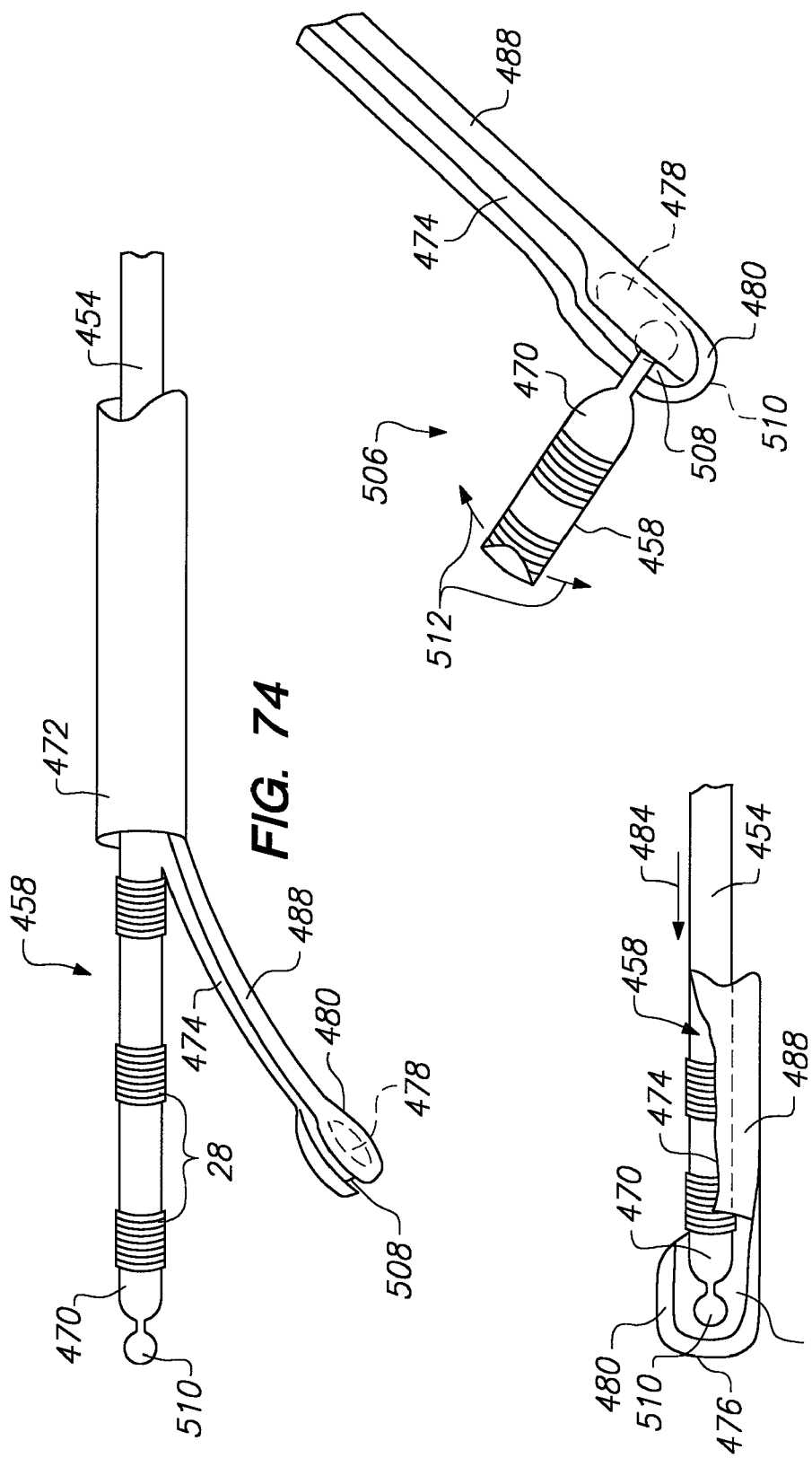

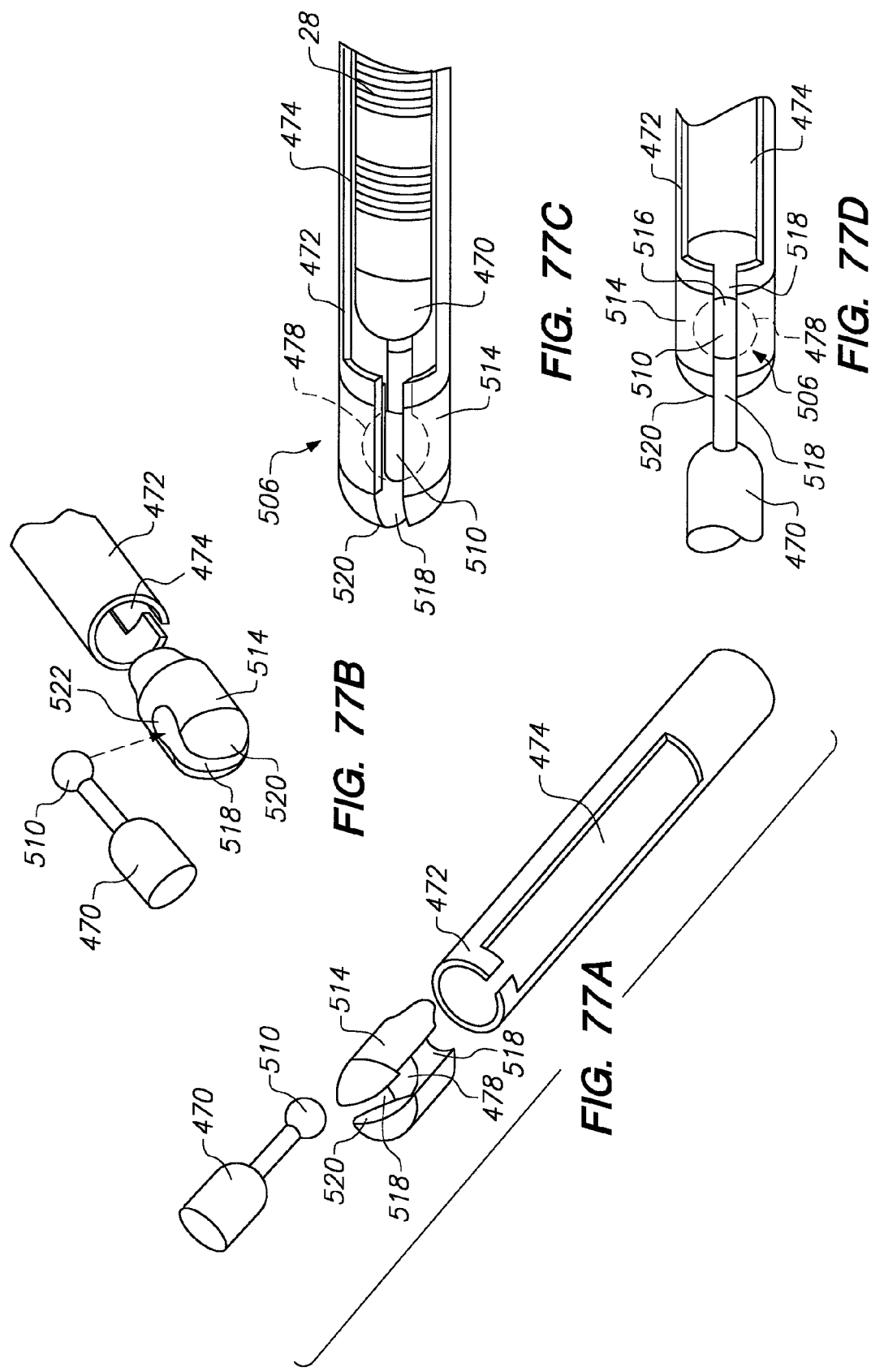

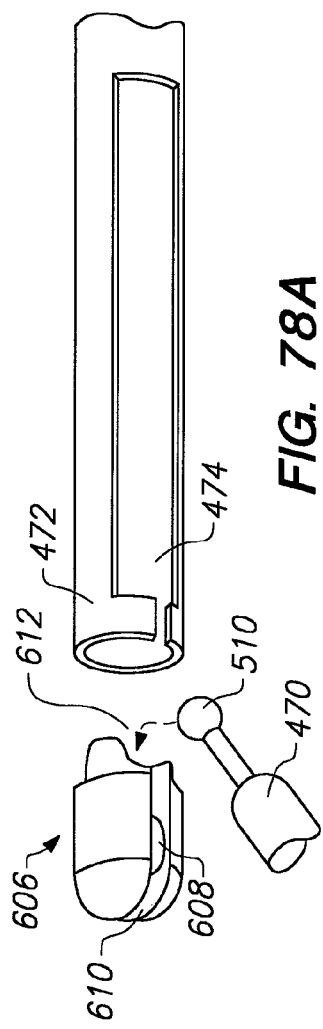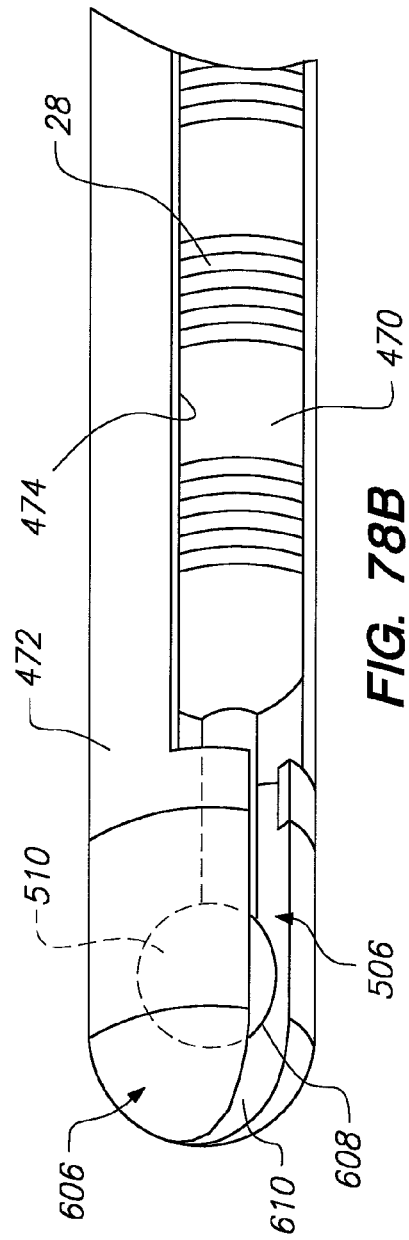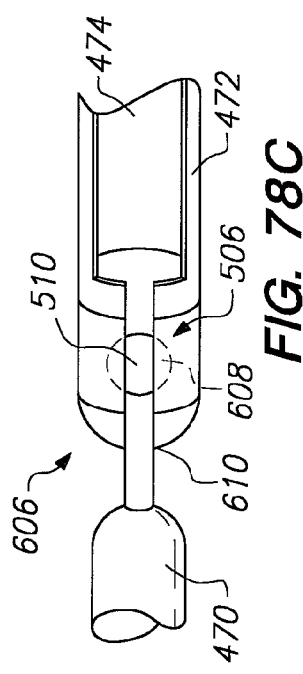

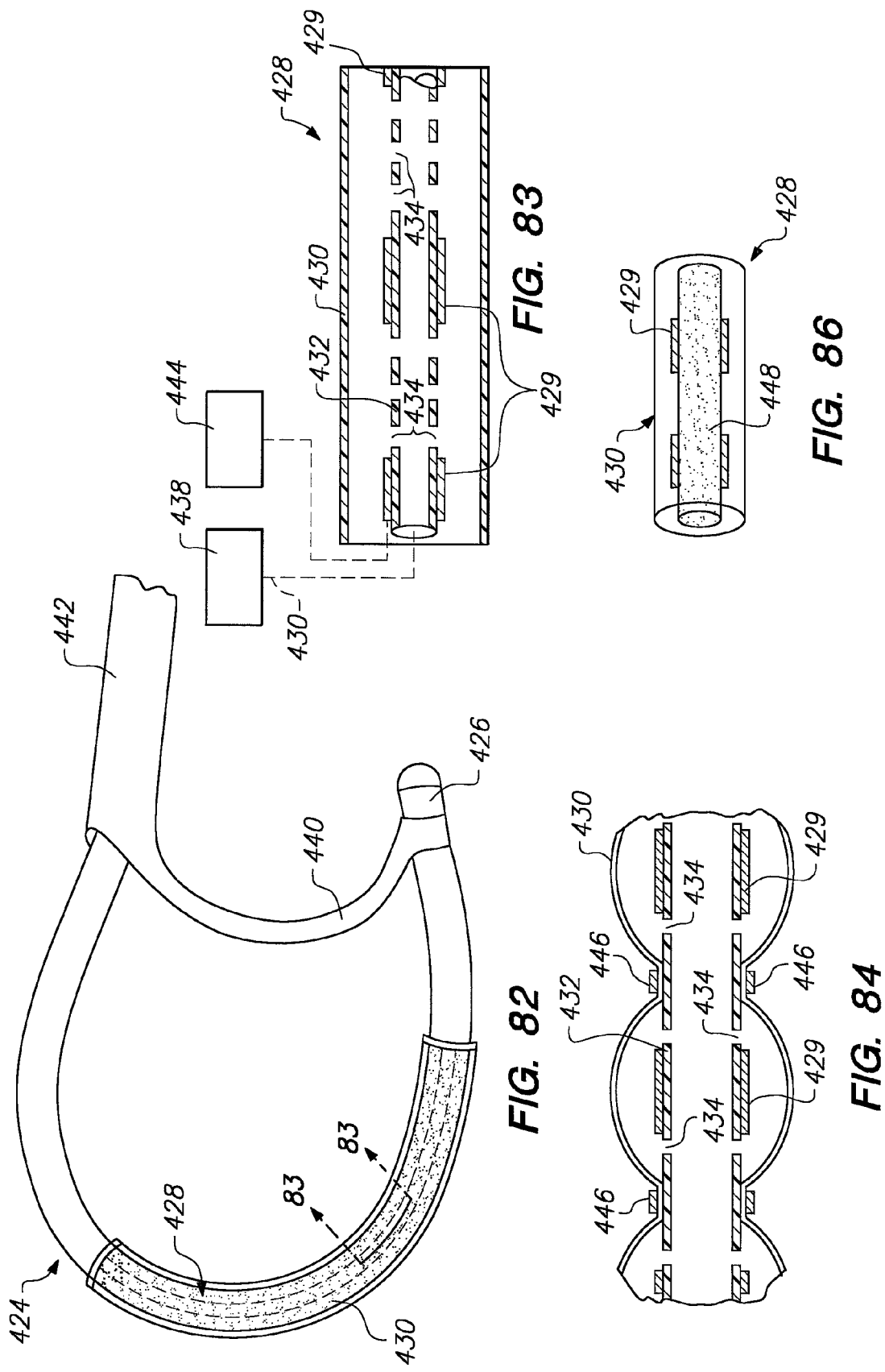

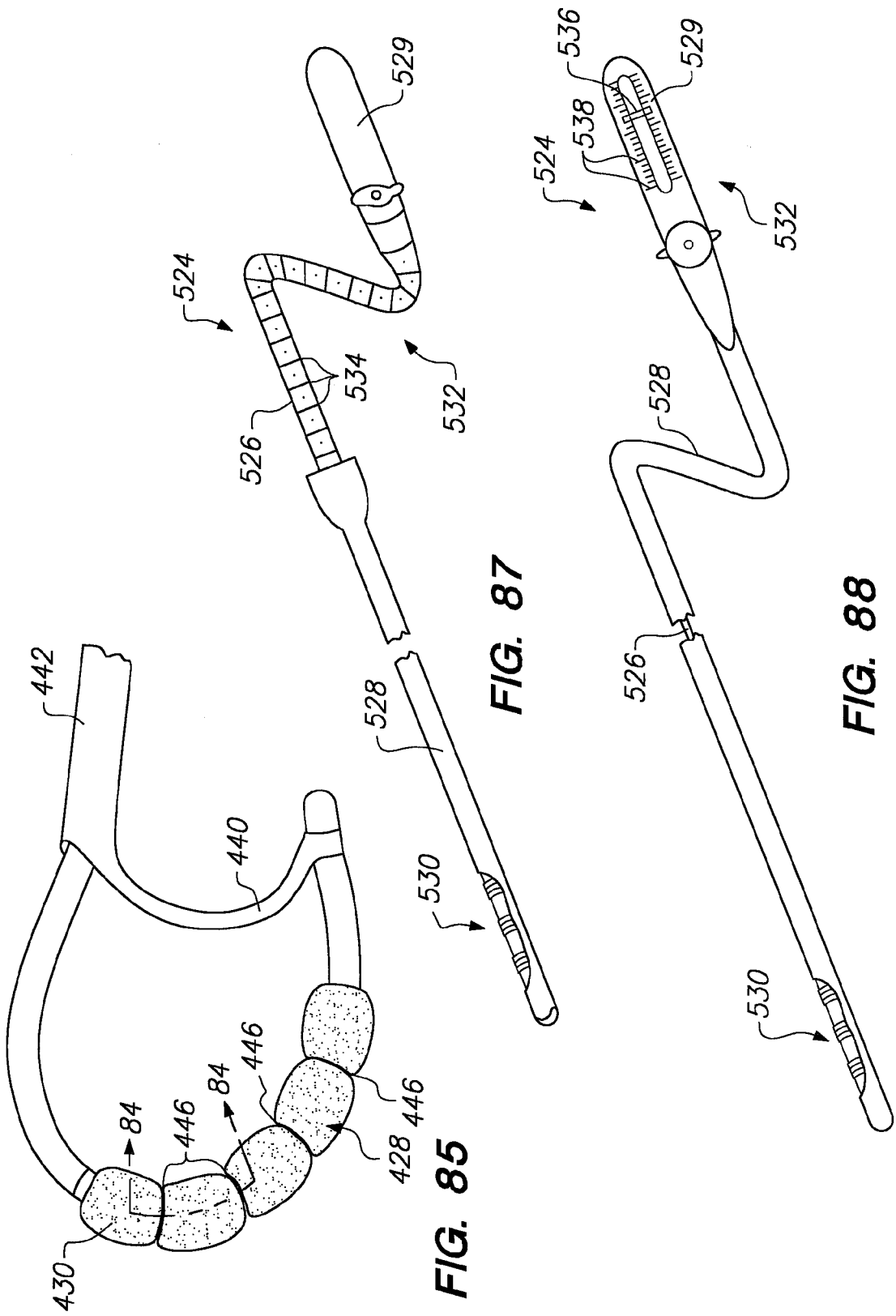

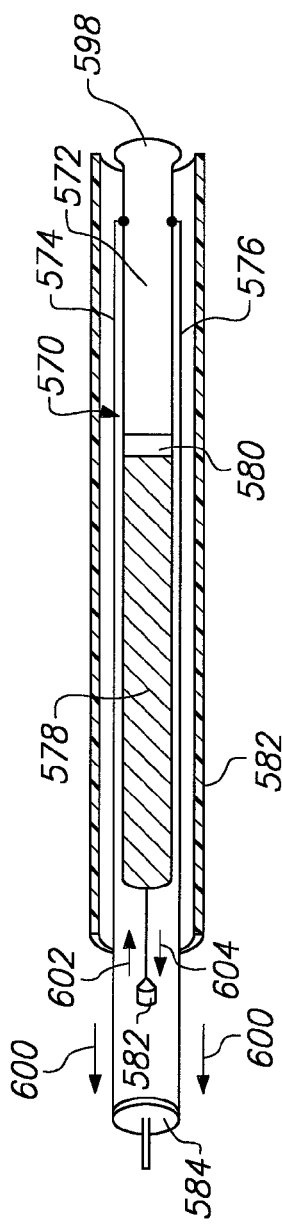
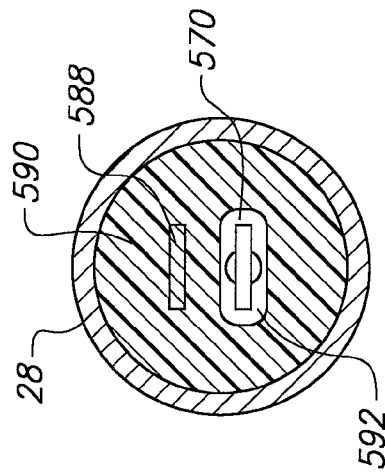
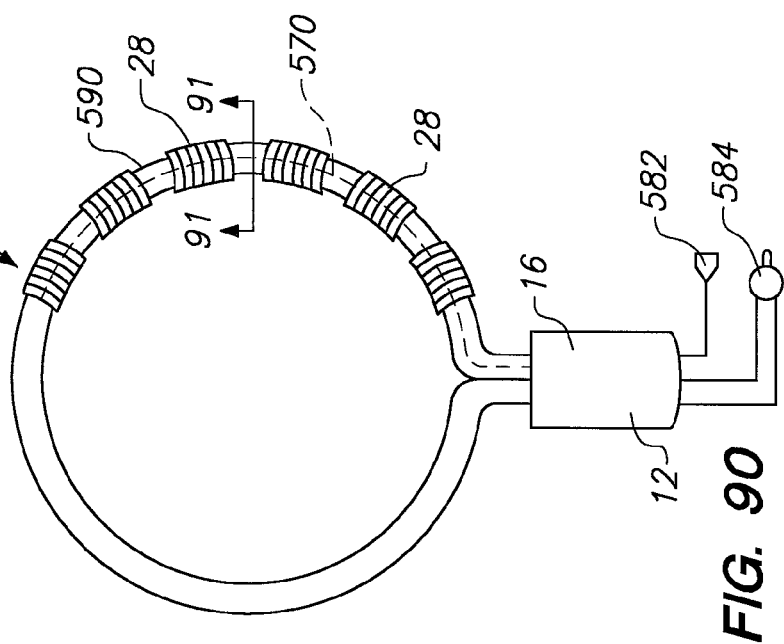
FIG. 89
FIG. 91
FIG. 90

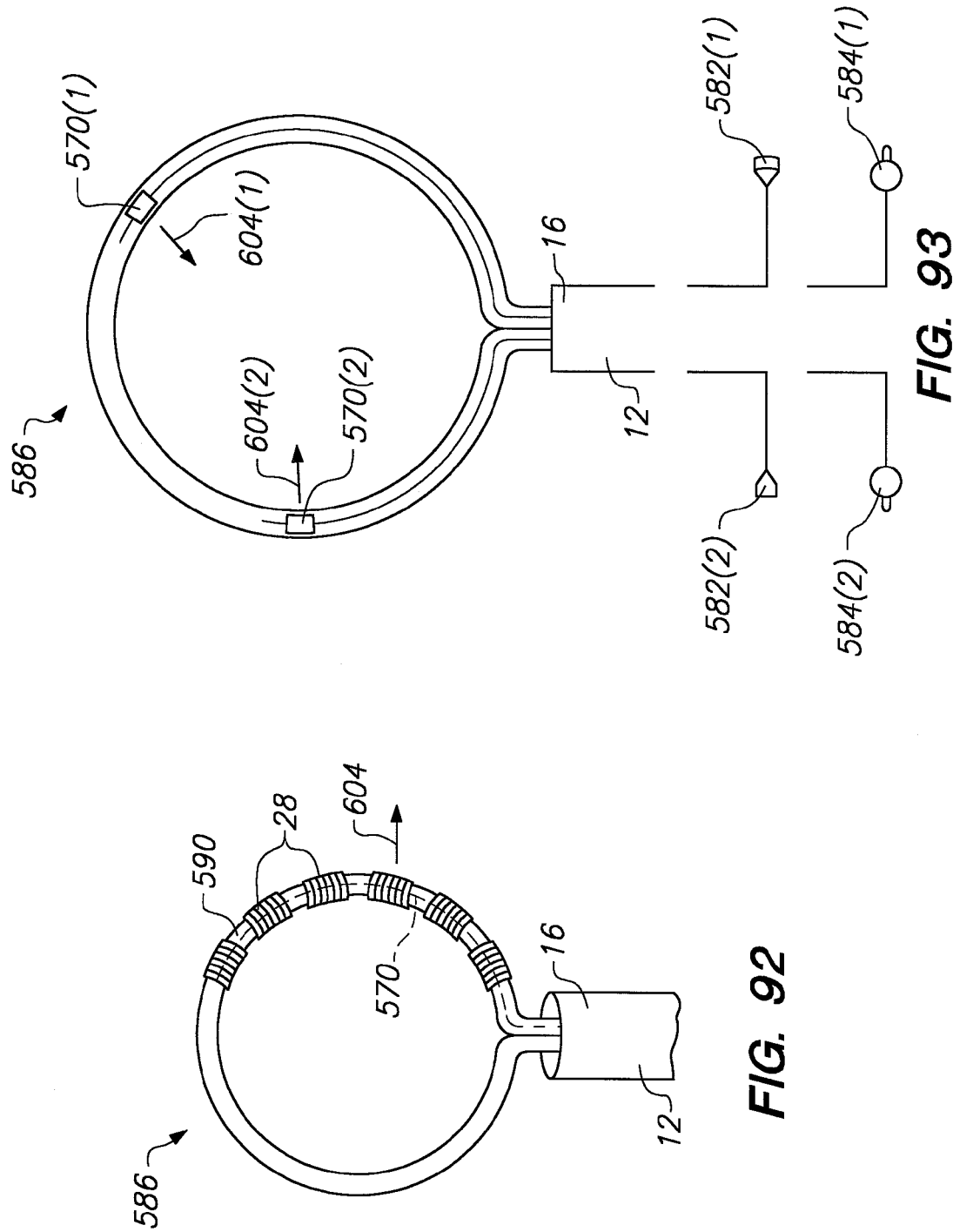

STRUCTURES FOR SUPPORTING MULTIPLE ELECTRODE ELEMENTS

CROSS-REFERENCE TO RELATED APPLICATIONS

This application is a continuation of U.S. application Ser. No. 10/112,407, filed Mar. 29, 2002 now U.S. Pat. No. 7,025,766, which is itself a continuation of U.S. application Ser. No. 09/523,685, filed Mar. 13, 2000, now U.S. Pat. No. 6,402,746, which is itself a continuation of U.S. application Ser. No. 08/771,217, filed Dec. 19, 1996, now U.S. Pat. No. 6,071,279.

FIELD OF THE INVENTION

The invention generally relates structures for supporting one or more diagnostic or therapeutic elements in contact with body tissue. In a more particular sense, the invention relates to structures well suited for supporting one or more electrode elements within the heart.

BACKGROUND OF THE INVENTION

The treatment of cardiac arrhythmias requires electrodes capable of creating tissue lesions having a diversity of different geometries and characteristics, depending upon the particular physiology of the arrhythmia to be treated.

For example, it is believed the treatment of atrial fibrillation and flutter requires the formation of continuous lesions of different lengths and curvilinear shapes in heart tissue. These lesion patterns require the deployment within the heart of flexible ablating elements having multiple ablating regions. The formation of these lesions by ablation can provide the same therapeutic benefits that the complex incision patterns that the surgical maze procedure presently provides, but without invasive, open heart surgery.

By way of another example, small and shallow lesions are desired in the sinus node for sinus node modifications, or along the A-V groove for various accessory pathway ablations, or along the slow zone of the tricuspid isthmus for atrial flutter (AFL) or AV node slow pathways ablations. However, the elimination of ventricular tachycardia (VT) substrates is thought to require significantly larger and deeper lesions.

There also remains the need to create lesions having relatively large surface areas with shallow depths.

The task is made more difficult because heart chambers vary in size from individual to individual. They also vary according to the condition of the patient. One common effect of heart disease is the enlargement of the heart chambers. For example, in a heart experiencing atrial fibrillation, the size of the atrium can be up to three times that of a normal atrium.

A need exists for electrode support structures that can create lesions of different geometries and characteristics, and which can readily adopt to different contours and geometries within a body region, e.g., the heart.

SUMMARY OF THE INVENTION

The invention provides structures for supporting operative therapeutic or diagnostic elements within an interior body region, like the heart. The structures possess the requisite flexibility and maneuverability permitting safe and easy introduction into the body region. Once deployed in the body region, the structures possess the capability to conform to different tissue contours and geometries to provide intimate contact between the operative elements and tissue.

In one embodiment, the invention provides a catheter assembly comprising a first branch body having a first axis and a second branch body, which extends in a non-parallel relationship with respect to the first axis. The assembly also includes a control to rotate the second branch body about the first axis.

In one embodiment, the second branch body includes a second axis. In this embodiment, a control rotates the second branch body about the second axis, as well as move the second branch body axially along the second axis.

In one embodiment, the second branch body carries at least one operative element, e.g., an electrode.

Another embodiment of the invention provides a method for forming lesions in the left atrium. The method provides a catheter assembly comprising a first branch body having a first axis, a second branch body extending in a non-parallel relationship with respect to the first axis, and at least one electrode carried by the second branch body. The method locates the first branch body within a pulmonary vein within the left atrium. The method locates the electrode carried by the second branch body in contact with endocardial tissue outside the pulmonary vein, while the first branch body is located within the pulmonary vein. The method transmits ablation energy from the electrode to contacted endocardial tissue while the first branch body is located within the pulmonary vein.

Other features and advantages of the inventions are set forth in the following Description and Drawings, as well as in the appended Claims.

BRIEF DESCRIPTION OF THE DRAWINGS

FIG. 1 is a perspective view of a probe, which carries on its distal region a multiple electrode support structure that embodies features of the invention;

FIG. 2A is an enlarged side view, with portions broken away and in section, of the distal region of the probe shown in FIG. 1;

FIG. 2B is a side view of the multiple electrode structure shown in FIG. 1, in which stiffness is varied using a slidable, tapered spline leg;

FIG. 3A is an enlarged side view of the distal region of the probe shown in FIG. 1, showing the multiple electrode structure advanced from the associated sheath to form a loop;

FIG. 3B is a perspective end view of an embodiment of the sheath shown in FIG. 3A, in which wires are placed to provide added torsional stiffness;

FIG. 3C is an end view of an embodiment of the sheath shown in FIG. 3A, which has been eccentrically extruded to provide added torsional stiffness;

FIG. 4A is a side view of the distal region shown in FIG. 3A, in which the catheter tube is stiffer than the sheath, and in which the catheter tube has been rotated within the sheath and flipped over upon itself;

FIG. 4B is a side view of the distal region shown in FIG. 3A, in which the catheter tube is not as stiff as the sheath, and in which the catheter tube has been rotated within the sheath to form an orthogonal bend in the loop;

FIG. 5 is a side view of an embodiment of the distal region shown in FIG. 3A, in which the size of the slot through which the loop extends can be varied;

FIG. 6 is a side view of an embodiment of the distal region shown in FIG. 3A, in which a prestressed spline within the loop structure alters the geometry of the structure;

FIG. 11 is a side view of an embodiment of the distal region shown in FIG. 3A, with the catheter tube having a prebent geometry orthogonal to the loop structure;

FIG. 12 is a side view of an embodiment of the distal region shown in FIG. 11, with the sheath advanced forward to straighten the prebent geometry;

FIG. 13A is a section view of the catheter tube within the sheath, in which the geometries of the sheath and catheter tube are extruded to prevent relative rotation;

FIG. 13B is a section view of the catheter tube within the sheath, in which the geometries of the sheath and catheter tube are extruded to permit limited relative rotation;

FIG. 14 is an enlarged side view of an alternative embodiment the distal region of the probe shown in FIG. 1;

FIG. 15A is a side view of the distal region shown in FIG. 14, showing the multiple electrode structure advanced from the associated sheath to form a loop;

FIG. 15B is a side view of an alternative embodiment of the distal region shown in FIG. 14;

FIGS. 16A, 16B, and 16C are view of the distal region shown in FIG. 14, showing alternative ways to stiffen the flexible junction between the sheath and the catheter tube;

FIG. 17A is an enlarged side view of an alternative embodiment the distal region of the probe shown in FIG. 1;

FIG. 21 is an enlarged side view of an alternative embodiment of the distal region of the probe shown in FIG. 1, with the associated sheath withdrawn and with no rearward force applied to the associated pull wire;

FIG. 22 is an enlarged side view of the distal region of the probe shown in FIG. 21, with the associated sheath advanced;

FIG. 23 is an enlarged side view of distal region of the probe shown in FIG. 21, with the associated sheath withdrawn and with rearward force applied to the associated pull wire to form a loop structure;

FIG. 24 is an enlarged side view of an alternative embodiment of the distal region shown in FIG. 21, with a pivot connection;

FIG. 25 is an enlarged elevation side view of an alternative embodiment of the distal region of the probe shown in FIG. 1, showing a preformed loop structure;

FIG. 26 is an enlarged, side section view of the slidable end cap shown in FIG. 25;

FIG. 27 is a side view of the distal region shown in FIG. 25, with the interior wire pulled axially to change the geometry of the preformed loop structure;

FIG. 28 is a side view of the distal region shown in FIG. 25, with the interior wire bend across its axis to change the geometry of the preformed loop structure;

FIG. 35 is an enlarged elevation side view of an alternative embodiment of the distal region of the probe shown in FIG. 1, showing a preformed loop structure, which, upon rotation, forms an orthogonal bend;

FIG. 36 is an enlarged side view of the distal region shown in FIG. 35, with the orthogonal bend formed;

FIG. 37 is a section view of the distal region shown in FIG. 35, taken generally along line 37-37 in FIG. 35;

FIG. 38 is a section view of the distal region shown in FIG. 35, taken generally along line 38-38 in FIG. 35;

FIG. 39 is a section view of the distal region shown in FIG. 36, taken generally along line 39-39 in FIG. 36;

FIG. 40 is an enlarged, perspective side view of an alternative embodiment of the distal region of the probe shown in FIG. 1, showing a pretwisted loop structure, which forms an orthogonal bend;

FIG. 41 is a side section view of a portion of the loop structure shown in FIG. 40, taken generally along line 41-41 in FIG. 40;

FIG. 42A is an enlarged side view of an alternative embodiment of the distal region of the probe shown in FIG. 1, showing a preformed loop structure, which, upon rotation, forms an orthogonal bend;

FIG. 42B is an enlarged side view of the distal region shown in FIG. 42A, with the orthogonal bend formed;

FIG. 45 is a side elevation view of an alternative embodiment of the distal region of the probe shown in FIG. 1, showing a self-anchoring, multiple electrode structure;

FIG. 46 is a section view of the self-anchoring structure shown in FIG. 45;

FIG. 47 is a side elevation view of an embodiment of the distal region shown in FIG. 48, in which the anchoring branch is movable;

FIG. 48 is a side elevation view of the distal region of the probe shown in FIG. 45, with the self-anchoring, multiple electrode structure withdrawn within an associated sheath;

FIGS. 49A, 49B, and 49C show the deployment of the multiple, self-anchoring electrode structure shown in FIG. 45 within a body region;

FIGS. 50A and 50B show, in diagrammatic form, the location of regions within the heart in which the self-anchoring structure shown in FIG. 45 can be anchored;

FIG. 51 is a side view of an embodiment of the self-anchoring structure shown in FIG. 45, in which the branch carrying electrode elements can be advanced or retracted or rotated along or about its axis;

FIG. 52 is a side view of an embodiment of the self-anchoring structure shown in FIG. 45, in which the branch carrying electrode elements can be torqued about the main axis of the structure;

FIG. 53 is a side elevation view of an alternative embodiment of the distal region of the probe shown in FIG. 1, showing a self-anchoring, loop structure;

FIG. 54 is a side elevation view of an alternative embodiment of the distal region shown in FIG. 54, also showing a type of a self-anchoring, loop structure;

FIG. 55 is a side elevation view of an alternative embodiment of the distal region shown in FIG. 45, showing a self-anchoring structure with an active anchoring element;

FIG. 61 is a side view of an alternative embodiment of the distal region of the probe shown in FIG. 1, showing a spring-assisted, spanning branch structure;

FIG. 62 is a side sectional view of the spring-assisted, spanning branch structure shown in FIG. 61, with the associated sheath advanced;

FIGS. 63A and 63B are side views of the deployment in a body region of the spring-assisted, spanning branch structure shown in FIG. 61;

FIG. 63C is a side view a spring-assisted, spanning branch structure, like that shown in FIG. 61, with an active tissue anchoring element;

FIG. 64 is a representative top view of long, continuous lesion pattern in tissue;

FIG. 65 is a representative top view of segmented lesion pattern in tissue;

FIG. 68 is a side view of the self-anchoring, loop structure shown in FIG. 67, showing the catheter tube advanced in an outwardly bowed loop shape from the associated sheath;

FIG. 69 is a side section view of a portion of the distal region shown in FIG. 66, showing the inclusion of a bendable spring to steer the self-anchoring loop structure;

FIG. 74 is a side view of a embodiment of a pivoting connection of the type shown in FIG. 73, with the catheter tube released from the associated sheath;

FIG. 75 is a side view, with parts broken away and in section, the pivoting connection shown in FIG. 74, with the catheter tube attached to the associated sheath;

FIG. 76 is a side perspective view of the pivoting connection shown in FIG. 75, with the catheter tube pivoting with respect to the associated sheath;

FIG. 77A is an exploded, perspective view of an alternative embodiment of a releasable pivoting connection of the type shown in FIG. 73, with the catheter tube detached from the associated sheath;

FIG. 77B is an exploded, perspective view of the reverse side of the pivoting connection shown in FIG. 77A, with the catheter tube detached from the associated sheath;

FIG. 77C is a top side view of the releasable pivoting connection shown in FIG. 77A, with the catheter tube attached to the associated sheath;

FIG. 77D is a top side view of the releasable pivoting connection shown in FIG. 77C, with the catheter tube attached to the associated sheath and pivoted with respect to the sheath;

FIG. 78A is an exploded, perspective view of an alternative embodiment of a releasable pivoting connection of the type shown in FIG. 73, with the catheter tube detached from the associated sheath;

FIG. 78B is a top view of the releasable pivoting connection shown in FIG. 78A, with the catheter tube attached to the associated sheath;

FIG. 78C is a top side view of the releasable pivoting connection shown in FIG. 78B, with the catheter tube attached to the associated sheath and pivoted with respect to the sheath;

FIG. 82 shows a loop structure of the type shown in FIG. 34A, which carries a porous ablation element;

FIG. 83 is a side section view of the porous ablation element taken generally along line 83-83 in FIG. 82;

FIG. 84 is a side section view of an alternative embodiment of the porous ablation element, showing segmented ablation regions, taken generally along line-84-84 in FIG. 85;

FIG. 85 is an exterior side view of the segmented ablation regions shown in section in FIG. 84;

FIG. 86 is a side section view of an alternative embodiment of a porous electrode element of the type shown in FIG. 82;

FIG. 87 is a side view of a probe, like that shown in FIG. 1, that includes indicia for marking the extent of movement of the catheter tube relative to the associated sheath;

FIG. 88 is a side view of an alternative embodiment of a probe, of the type shown in FIG. 1, showing indicia for marking the extent of movement of the catheter tube relative to the associated sheath;

FIG. 89 is a side sectional view of a catheter tube having a movable steering assembly;

FIG. 90 is an elevated side view of a preformed loop structure having a movable steering mechanism as shown in FIG. 89;

FIG. 91 is a section view of the loop structure shown in FIG. 90, taken generally alone line 91-91 in FIG. 90;

FIG. 92 is an elevated side view of using the movable steering mechanism shown in FIG. 89 to change the geometry of the loop structure shown in FIG. 90; and FIG. 93 is an elevated side view of using two movable steering mechanisms, as shown in FIG. 89, to change the geometry of a loop structure.

Figure 9:
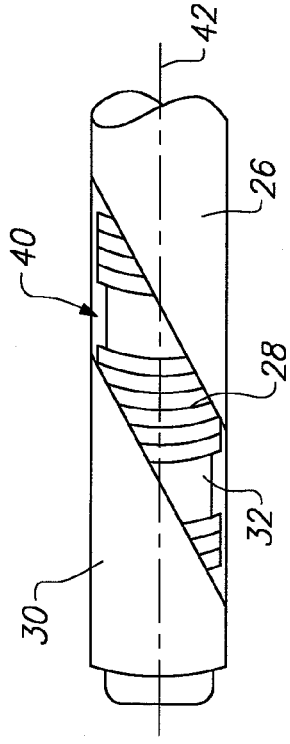
FIG. 9 is a side view of an embodiment of the distal region shown in FIG. 3A, in which the slot has a helical geometry.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

This Specification discloses various multiple electrode structures in the context of catheter-based cardiac ablation. That is because the structures are well suited for use in the field of cardiac ablation.

Still, it should be appreciated that the disclosed structures are applicable for use in other applications. For example, the various aspects of the invention have application in procedures requiring access to other regions of the body, such as, for example, the prostrate, brain, gall bladder, and uterus. The structures are also adaptable for use with systems that are not necessarily catheter-based.

I. Flexible Loop Structures

A. Slotted Jointed Sheath

FIG. 1 shows a multiple electrode probe 10 that includes a structure 20 carrying multiple electrode elements 28.

The probe 10 includes a flexible catheter tube 12 with a proximal end 14 and a distal end 16. The proximal end 14 has an attached handle 18. The multiple electrode structure 20 is attached to the distal end 16 of the catheter tube 14 (see FIG. 2A).

The electrode elements 28 can serve different purposes. For example, the electrode elements 28 can be used to sense electrical events in heart tissue. Alternatively, or in addition, the electrode elements 28 can serve to transmit electrical pulses to measure the impedance of heart tissue, to pace heart tissue, or to assess tissue contact. In the illustrated embodiment, the principal use of the electrode elements 28 is to transmit electrical energy, and, more particularly, electromagnetic radio frequency energy, to ablate heart tissue.

The electrode elements 28 are electrically coupled to individual wires (not shown in FIG. 1, but which will be discussed in greater detail later) to conduct ablating energy to them. The wires from the structure 20 are passed in conventional fashion through a lumen in the catheter tube 12 and into the handle 18, where they are electrically coupled to a connector 38 (see FIG. 1). The connector 38 plugs into a source of RF ablation energy.

As FIG. 2A shows, the support structure 20 comprises a flexible spline leg 22 surrounded by a flexible, electrically nonconductive sleeve 32. The multiple electrodes 28 are carried by the sleeve 32.

The spline leg 22 is preferably made from resilient, inert wire, like Nickel Titanium (commercially available as Nitinol material) or 17-7 stainless steel. However, resilient injection molded inert plastic can also be used. Preferably, the spline leg 22 comprises a thin, rectilinear strip of resilient metal or plastic material. Still, other cross sectional configurations can be used.

The spline leg 22 can decrease in cross sectional area in a distal direction, by varying, e.g., thickness or width or diameter (if round), to provide variable stiffness along its length. Variable stiffness can also be imparted by composition changes in materials or by different material processing techniques.

As FIG. 2B shows, the stiffness of the support structure 20 can be dynamically varied on the fly by providing a tapered wire 544 slidably movable within a lumen 548 in the structure 20. Movement of the tapered wire 544 (arrows 546 in FIG. 2B) adjusts the region of stiffness along the support structure 20 during use.

The sleeve 32 is made of, for example, a polymeric, electrically nonconductive material, like polyethylene or polyurethane or PEBAX™ material (polyurethane and nylon). The signal wires for the electrodes 28 preferably extend within the sleeve 32.

The electrode elements 28 can be assembled in various ways. They can, for example, comprise multiple, generally rigid electrode elements arranged in a spaced apart, segmented relationship along the sleeve 32. The segmented electrodes can each comprise solid rings of conductive material, like platinum, which makes an interference fit about the sleeve 32. Alternatively, the electrode segments can comprise a conductive material, like platinum-iridium or gold, coated upon the sleeve 32 using conventional coating techniques or an ion beam assisted deposition (IBAD) process.

Alternatively, the electrode elements 28 can comprise spaced apart lengths of closely wound, spiral coils wrapped about the sleeve 32 to form an array of generally flexible electrode elements 28. The coils are made of electrically conducting material, like copper alloy, platinum, or stainless steel, or compositions such as drawn-filled tubing. The electrically conducting material of the coils can be further coated with platinum-iridium or gold to improve its conduction properties and biocompatibility.

The electrode elements 28 can also comprise porous materials, which transmit ablation energy through transport of an electrified ionic medium. Representative embodiments of porous electrode elements 28 are shown in FIGS. 82 to 85, and will be described in greater detail later.

The electrode elements 28 can be operated in a uni-polar mode, in which the ablation energy emitted by the electrode elements 28 is returned through an indifferent patch electrode 420 (see FIG. 44) externally attached to the skin of the patient. Alternatively, the elements 28 can be operated in a bi-polar mode, in which ablation energy emitted by one or more electrode element 28 is returned through an electrode element 28 on the structure 20 (see FIG. 3A).

The diameter of the support structure 20 (including the electrode elements 28, flexible sleeve 32, and the spline leg 22) can vary from about 2 French to about 10 French.

The support structure 20 must make and maintain intimate contact between the electrode elements 28 and the endocardium. Furthermore, the support structure 20 must be capable of assuming a relatively low profile for steering and introduction into the body.

To accomplish these objectives, the probe 10 includes a sheath 26 carried by the catheter tube 12. The distal section 30 of the sheath 26 extends about the multiple electrode structure 20 (see FIGS. 1 and 2A). The distal section 30 of the sheath 26 is joined to the end of the multiple electrode structure, e.g. by adhesive or thermal bonding.

In the embodiment shown in FIG. 1, the proximal section 34 of the sheath 26 terminates short of the handle 18 and includes a raised gripping surface 36. The proximal section 34 also includes a hemostatic valve and side port (not shown) for fluid infusion. Preferably the hemostatic valve locks about the catheter tube 12.

The distal section 30 of the sheath 26 (proximal of its connection to the multiple electrode structure 20) includes a preformed slot 40, which extends along the axis of the catheter tube 12 (see FIG. 2A). A portion of the multiple electrode structure 20 is exposed through the slot 40.

The length and size of the slot 40 can vary, as will be described in greater detail later. The circumferential distance that slot 40 extends about the axis 42 can also vary, but is always less than the outer diameter of the sheath 26. Thus, a remnant 44 of the sheath 26 underlies the slot 40. In the illustrated embodiment, the slot 40 extends about 180° about the sheath 26.

The catheter tube 12 is slidable within the sheath in a forward and rearward direction, as indicated by arrows 46 and 48 in FIG. 1. By grasping the raised gripping surface 36 at the proximal end of the sheath 26, and pushing the catheter tube 12 in the forward direction (arrow 46) through the sheath 26 (see FIG. 3A), the structure 20, secured to the catheter tube 12 and to the end 30 of the sheath 26, bends outwardly from the slot 40. The sheath remnant 44 forms a flexible joint, keeping the distal end of the structure 20 close to the catheter tube axis 42, while the element 20 bends into a loop, as FIG. 3A shows. The flexible joint 44 maintains loop stress within the structure 20, to thereby establish and maintain intimate contact between the electrode elements 28 and tissue.

The physician can alter the diameter of the loop structure 20 from large to small, by incrementally moving the catheter tube 12 in the forward and rearward directions (arrows 46 and 48) through the sheath 26. In this way, the physician can manipulate the loop structure 20 to achieve the desired degree of contact between tissue and the electrode elements 28.

If desired, the physician can, while grasping the raised gripping surface 36, rotate the catheter tube 12 within the sheath 26. As FIG. 4A shows, when the catheter tube 12 is torsionally stiffer than the sheath 26, the relative rotation (arrow 50) flips the loop structure 20 over upon itself (compare FIGS. 3A and 4A), to place the electrode elements 28 in a different orientation for tissue contact. As FIG. 4B shows, when the sheath 26 is torsionally stiffer than the catheter tube 12, rotation of the catheter tube within the sheath 26 bends the structure 20 generally orthogonally to the axis of the loop.

By grasping the raised gripping surface 36 and pulling the catheter tube 12 in the rearward direction (arrow 48), the physician draws the multiple electrode structure 20 back into the sheath 26, as FIG. 2A shows. Housed within the sheath 26, the multiple electrode structure 20 and sheath 26 form a generally straight, low profile geometry for introduction into and out of a targeted body region.

The sheath 26 is made from a material having a greater inherent stiffness (i.e., greater durometer) than the support structure 20 itself. Preferably, the sheath material is relatively thin (e.g., with a wall thickness of about 0.005 inch) so as not to significantly increase the overall diameter of the distal region of the probe 10 itself. The selected material for the sheath 26 is preferably also lubricious, to reduce friction during relative movement of the catheter tube 12 within the sheath 26. For example, materials made from polytetrafluoroethylene (PTFE) can be used for the sheath 26.

Additional stiffness can be imparted by lining the sheath 26 with a braided material coated with PEBAX™ material (comprising polyurethane and nylon). Increasing the sheath stiffness imparts a more pronounced D-shape geometry to the formed loop structure 20 orthogonal to the axis of the slot 40. Other compositions made from PTFE braided with a stiff outer layer and other lubricious materials can be used. Steps are taken to keep remnants of braided materials away from the exposed edges of the slot 40. For example, the pattern of braid can be straightened to run essentially parallel to the axis of the sheath 26 in the region of the slot 40, so that cutting the slot does not cut across the pattern of the braid.

The flexible joint 44 is durable and helps to shape the loop structure. The flexible joint 44 also provides an anchor point for the distal end 16 of the catheter tube 12. The joint 44 also provides relatively large surface area, to minimize tissue trauma. The geometry of the loop structure 20 can be altered by varying either the stiffness or the length of the flexible joint 44, or both at the same time.

As FIG. 3A shows, a stiffening element 52 can be placed along the joint 44. For example, the stiffening element 52 can comprise an increased durometer material (e.g., from about 35 D to about 72 D), which is thermally or chemically bonded to the interior of the joint 44. Examples of increased durometer materials, which will increase joint stiffness, include nylon, tubing materials having metal or nonmetallic braid in the wall, and PEBAX™ material. Alternatively, the stiffening element 52 can comprise memory wire bonded to the interior of the joint 44. The memory wire can possess variable thickness, increasing in the proximal direction, to impart variable stiffness to the joint 44, likewise increasing stiffness in the proximal direction. The memory wire can also be preformed with resilient memory, to normally bias the joint 44 in a direction at an angle to the axis of the slot 40.

As FIG. 3B shows, the stiffening element 52 can comprise one or more lumens 546 within the joint 44, which carry wire material 548. The lumens 546 and wire material 548 can extend only in the region of the joint 44, or extend further in a proximal direction into the main body of the sheath 26, to thereby impart greater stiffness to the sheath 26 as well.

As FIG. 3C shows, greater stiffness for the joint 44 can be imparted by extruding the sheath 26 to possess an eccentric wall thickness. In this arrangement, the wall of the sheath 26 has a region 550 of greater thickness in the underbody of the sheath 26, which becomes the joint 44, than the region 552 which is cut away to form the slot 40. As shown in phantom lines in FIG. 3C, one or more of the lumens 546 can be extruded in the thicker region 550, to receive wire material to further stiffen the region of the joint 44.

Regardless of its particular form, the stiffening element 52 for the joint 44 changes the geometry of the formed loop structure 20.

Figure 7A:
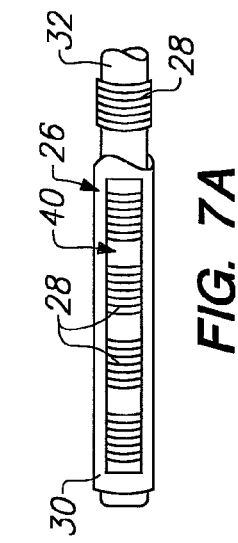
FIGS. 7A, 7B, and 7C are top views of different embodiments of the distal region shown in FIG. 3A, in which the slot is shown having different geometries, which affect the geometry of the resulting loop.
Figure 7B:
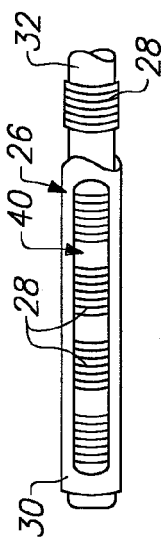
Figure 7C:
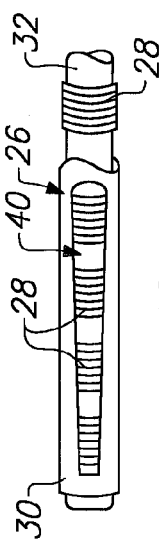

The geometry of the formed loop structure 20 can also be modified by altering the shape and size of the slot 40. The slot periphery can have different geometries, e.g., rectangular (see FIG. 7A), elliptical (see FIG. 7B), or tapered (see FIG. 7C), to establish different geometries and loop stresses in the formed structure 20.

The effective axial length of the slot 44 can be adjusted by use of a movable mandrel 54, controlled by a push-pull stylet member 56 (see FIG. 5) attached to a slider controller 58 in the handle 18. Axial movement of the mandrel 54 affected by the stylet member 56 enlarges or decreases the effective axial length of the slot 44. A nominal slot length in the range of 1¼ inch to 1½ inch will provide the D-shape loop structure 20 shown in FIG. 3A. Shorter slot lengths will provide a less pronounced D-shape, with a smaller radius of curvature.

Figure 8:
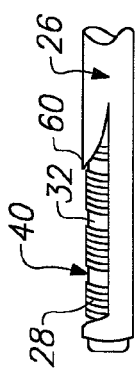
FIG. 8 is a side view of an embodiment of the distal region shown in FIG. 3A, in which the proximal end of the slot is tapered to facilitate formation of the loop.

Larger slot lengths will provide a more pronounced D-shape, with a larger radius of curvature. As FIG. 8 shows, the proximal edge 60 of the slot 40 can be tapered distally to guide bending of the structure 20 into the desired loop shape while being advanced through the slot 40.

Figure 10:
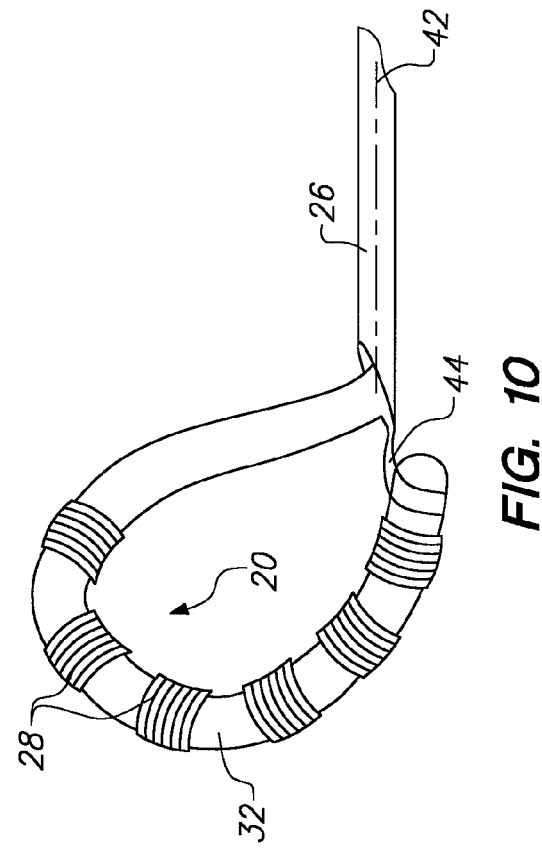
FIG. 10 is a side view of the distal region shown in FIG. 9, with the loop support structure deployed through the helical slot.

Instead of extending generally parallel to the catheter tube axis 42, as FIGS. 1 to 8 show, the slot 40 can extend across the catheter tube axis 42, as FIG. 9 shows. When advanced from the cross-axis slot 40, the loop structure 20 extends more orthogonally to the catheter tube axis 42, as FIG. 10 shows, compared to the more distal extension achieved when the slot 40 is axially aligned with the catheter tube axis 42, as FIG. 3A generally shows.

As FIG. 6 shows, a region 62 of the spline 22 within the structure 20 away from the electrode elements 28 can be preformed with elastic memory to bow radially away from the electrode elements 28 when advanced from the sheath 26. The radially outward bow of the preformed region 62 forms a more symmetric loop structure 20', in contrast to the more asymmetric D-shaped loop 20 shown in FIG. 3A. When in contact with tissue, the preformed, outwardly bowed region 62 generates a back pressure that, in combination with the loop stress maintained by the flexible joint 44, establishes greater contact pressure between electrode elements 28 and tissue.

In FIG. 6, the region 62 is preformed with a generally uniform bend in a single plane. The region 62 can be preformed with complex, serpentine bends along a single plane, or with bends that extend in multiple planes. Further details of representative loop structures having complex, curvilinear geometries will be described in greater detail later.

Additional tissue contact forces can be generated by mounting a bendable spring 64 in the distal end 16 of the catheter tube (see FIG. 2A). One or more steering wires 66 are bonded (e.g., soldered, spot welded, etc.) to the bendable spring 64 extend back to a steering mechanism 68 in the handle 18 (see FIG. 1). Details of steering mechanisms that can be used for this purpose are shown in Lundquist and Thompson U.S. Pat. No. 5,254,088, which is incorporated into this Specification by reference. Operation of the steering mechanism 68 pulls on the steering wires 66 to apply bending forces to the spring 64. Bending of the spring 64 bends the distal end 16 of the catheter tube 12, as shown in phantom lines in FIG. 1.

The plane of bending depends upon the cross section of the spring 64 and the attachment points of the wires 66. If the spring 64 is generally cylindrical in cross section, bending in different planes is possible. If the spring 64 is generally rectilinear in cross section, anisotropic bending occurs perpendicular to the top and bottom surfaces of the spring 64, but not perpendicular to the side surfaces of the spring 64.

Alternatively, or in combination with the manually bendable spring 64, the distal end 16 of the catheter tube 12 can be prebent to form an elbow 70 (see FIG. 11) generally orthogonal or at some other selected angle to the loop structure 20. In the illustrated embodiment, a preformed wire 72 is secured, e.g., by soldering, spot welding, or with adhesive, to the end 16 of the catheter tube 12. The preformed wire 72 is biased to normally curve. The preformed wire 72 may be made from stainless steel 17/7, nickel titanium, or other memory elastic material. It may be configured as a wire or as a tube with circular, elliptical, or other cross-sectional geometry.

The wire 72 normally imparts its curve to the distal catheter tube end 16, thereby normally bending the end 16 in the direction of the curve. The direction of the normal bend can vary, according to the functional characteristics desired. In this arrangement, a sheath 74 slides (arrows 76) along the exterior of the catheter body 14 between a forward position overlying the wire 72 (FIG. 12) and an aft position away from the wire 72 (FIG. 11). In its forward position, the sheath 74 retains the distal catheter end 16 in a straightened configuration against the normal bias of the wire 72, as FIG. 12 shows. The sheath 74 may include spirally or helically wound fibers to provide enhanced torsional stiffness to the sheath 74. Upon movement of the sheath 74 to its aft position, as FIG. 11 shows, the distal catheter end 16 yields to the wire 72 and assumes its normally biased bent position. The slidable sheath 74 carries a suitable gripping surface (not shown), like the gripping surface 36 of the sheath 26, to affect forward and aft movement of the sheath 74 for the purposes described.

FIG. 4 shows the loop structure 20 flipped upon itself by rotation of the loop structure 20 within the sheath 26. The rotation is allowed, because both the loop structure 20 and sheath 26 possess generally cylindrical cross sections. If it is desired to prevent relative rotation of the structure 20 within the sheath 26, the outer geometry of the structure 20 and the interior geometry of the sheath 26 can be formed as an ellipse, as FIG. 13A shows. The interference (elliptically keyed) arrangement in FIG. 13A prevents rotation of the structure 20 and also provides improved torque response and maintains the electrode elements 28 is a fixed orientation with respect to the sheath 26. By matching the outer geometry of the structure 20 and the interior geometry of the sheath 26 (see FIG. 13B), a prescribed range of relative rotation can be allowed before interference occurs. In FIG. 13B, the elliptical sleeve 32 will rotate until it contacts the butterfly shaped keyway within the sheath 26. The prescribed range allows the loop structure 20 to be flipped over upon itself in the manner shown in FIG. 4, without wrapping the flexible joint 44 about the sheath 26. Should the flexible joint 44 become wrapped about the sheath 26, the physician must rotate of the catheter tube 12 to unwrap the joint 44, before retracting the structure 20 back into the slotted sheath 26.

B. Distal Wire Joint

FIGS. 14 and 15 show another structure 100 carrying multiple electrode elements 28. In many respects, the structure 100 shares structural elements common to the structure 20 shown in FIGS. 2 and 3, as just discussed. For this reason, common reference numerals are assigned. Like the structure 20 shown in FIGS. 2 and 3, the structure 100 is intended, in use, to be carried at the distal end 16 of a flexible catheter tube 12, as a part of a probe 10, as shown in FIG. 1.

Like the structure 20 shown in the FIGS. 2 and 3, the support structure 100 comprises a flexible spline leg 22 surrounded by a flexible, electrically nonconductive sleeve 32. The multiple electrodes 28 are carried by the sleeve 32. The range of materials usable for the spline leg 22 and the electrodes 28 of the structure 100 are as previously described for the structure 20.

A sheath 102 is carried by the catheter tube 12. The distal section 104 of the sheath 102 extends about the multiple electrode structure 100. As FIGS. 14 and 15A show, the distal section 104 of the sheath 102 is joined to the distal end 108 of the multiple electrode structure 100 by a short length of wire 106. The wire 106 is joined to the two ends 104 and 108, for example, by adhesive or thermal bonding. The proximal section of the sheath 102 is not shown in FIG. 13, but terminates short of the handle 18 and includes a raised gripping surface 36, as shown for the probe 10 in FIG. 1. In FIG. 15A, the wire 106 is joined to the interior of the sheath 102. Alternatively, as FIG. 15B shows, the wire 106 can be joined to the exterior of the sheath 102.

Like the sheath 26 described in connection with FIGS. 2 and 3A, the sheath 102 is made from a material having a greater inherent stiffness than the support structure 100 itself, e.g., composite materials made from PTFE, braid, and polyimide. The selected material for the sheath 102 is preferably also lubricious. For example, materials made from polytetrafluoroethylene (PTFE) can be used for the sheath 102. As for the sheath 26 in FIGS. 2 and 3, additional stiffness can be imparted by incorporating a braided material coated with PEBAX™ material.

The wire 106 comprises a flexible, inert cable constructed from strands of metal wire material, like Nickel Titanium or 17-7 stainless steel. Alternatively, the wire 106 can comprise a flexible, inert stranded or molded plastic material. The wire 106 in FIG. 14 is shown to be round in cross section, although other cross sectional configurations can be used. The wire 106 may be attached to the sheath 102 by thermal or chemical bonding, or be a continuation of the spline leg 22 that forms the core of the structure 100. The wire 106 can also extend through the wall of the sheath 102, in the same way that the stiffening wires 548 are placed within the sheath 26 (shown in FIG. 3B). The need to provide an additional distal hub component to secure the wire 106 to the remainder of the structure 100, is thereby eliminated.

The catheter tube 12 is slidable within the sheath 102 to deploy the structure 100. Grasping the raised gripping surface 36 at the proximal end of the sheath 102, while pushing the catheter tube 12 in the forward direction through the sheath 102 (as shown by arrow 110 in FIG. 15A), moves the structure 100 outward from the open distal end 112 of the sheath 102. The wire 106 forms a flexible joint 144, pulling the distal end 108 of the structure 100 toward the sheath distal section 104. The structure 100 thereby is bent into a loop, as FIG. 15A shows.

The flexible wire joint 106, like the sheath joint 44 in FIG. 3A, possesses the flexibility and strength to maintain loop stress within the structure 100 during manipulation, to thereby establish and maintain intimate contact between the electrode elements 28 and tissue. The wire 106 presents a relatively short length, thereby minimizing tissue trauma. A representative length for the wire 106 is about 0.5 inch.

Like the loop structure 20, the physician can alter the diameter of the loop structure 100 from large to small, by incrementally moving the catheter tube 12 in the forward direction (arrow 110 in FIG. 15) and rearward direction (arrow 116 in FIG. 15) through the sheath 102. In this way, the physician can manipulate the loop structure 100 to achieve the desired degree of contact between tissue and the electrode elements 28.

Moving the structure 100 fully in the rearward direction (arrow 116) returns the structure 100 into a low profile, generally straightened configuration within the sheath 102 (as FIG. 14 shows), well suited for introduction into the intended body region.

The points of attachment of the wire joint 106 (between the distal structure end 108 and the distal sheath section 104), coupled with its flexible strength, make it possible to form loops with smaller radii of curvature than with the flexible sheath joint 44 shown in FIG. 3A.

The geometry of the loop structure 100 can be altered by varying either the stiffness or the length of the flexible wire 106, or both at the same time. As FIG. 16A shows, the flexible wire 106 can be tapered, to provide a cross section that decreases in the distal direction. The tapered cross section provides varying stiffness, which is greatest next to the sheath 102 and decreases with proximity to the distal end 108 of the structure 100.

The stiffness can also be changed by changing the thickness of the wire 106 in a step fashion. FIG. 16B shows the wire 106 attached to the sheath 102 and having the smallest thickness to increase the bending radius. The thickness of the wire 106 increases in a step fashion leading up to its junction with the spline leg 22. Changing the thickness of the wire can be done by rolling the wire in steps, or by pressing it, or by chemical etching.

As FIG. 16C shows, the wire 106 can also be used to impart greater stiffness to the flexible joint 144, for the reasons described earlier with regard to the flexible joint 44 shown in FIG. 3A. In FIG. 16C, the wire 106 is thermally or chemically bonded to the flexible joint 144 in a serpentine path of increasing width. The alternative ways of stiffening the flexible joint 44 (shown in FIGS. 3A, 3B, and 3C) can also be used to stiffen the flexible joint 144.

In the illustrated embodiment (see FIGS. 15A and 16A), the distal sheath section 104 is cut at an angle and tapered in a transverse direction relative to the axis of the sheath 102. The angled linear cut on the distal sheath section 104 may also be a contoured elongated opening (see FIG. 15B) to make the initiation of the loop formation easier. The angle cut on the sheath 102 helps deploy and minimizes the length of the wire 106. It is advantageous to cover with the sheath section 104 a significant portion of the wire joint 144. The sheath section 104 thereby also serves to shield the wire as much as possible from direct surface contact with tissue. The possibility of cutting tissue due to contact with the wire 106 is thereby minimized.

As before described in the context of the structure 20, additional tissue contact forces between the structure 100 and tissue can be generated by mounting a bendable spring 64 in the distal end 16 of the catheter tube (see FIG. 14). Alternatively, or in combination with the manually bendable spring 64, the distal end 16 of the catheter tube 12 can be prebent to form an elbow 70 (as shown in FIG. 11 in association with the structure 20) generally orthogonal or at some other selected angle to the loop structure 100.

FIG. 17A shows an alternative embodiment for the structure 100. In this embodiment, the wire 106 is not attached to the distal sheath section 104. Instead, the wire 106 extends through the sheath 102 to a stop 118 located proximal to the gripping surface 36 of the sheath 102. Holding the stop 118 stationary, the physician deploys the loop structure 100 in the manner already described, by advancing the catheter tube 12 through the sheath 102 (arrow 120 in FIG. 17A). Once the loop structure 100 has been formed, the physician can pull on the wire 106 (arrow 122 in FIG. 17A) to decrease its exposed length beyond the distal sheath section 104, to minimize tissue trauma. Further adjustments to the loop are made by advancing or retracting the catheter tube 12 within the sheath 102. The wire 106 unattached to the sheath 102 allows the physician to interchangeably use the structure 100 with any sheath.

Figure 17B:
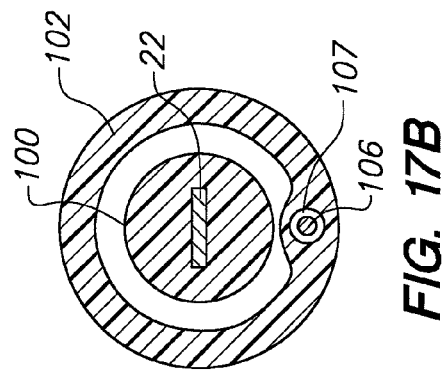
FIG. 17B is a section view of an embodiment of the distal region shown in FIG. 17A.

Alternatively, as FIG. 17B shows, the sheath 102 can include a lumen 107 through which the wire 106 passes. In this embodiment, the presence of the wire 106 within the body of the sheath 102 provides increased torque. Unlike FIG. 17A, however, the sheath and the wire 106 comprise one integrated unit and cannot be interchanged.

Figure 20:
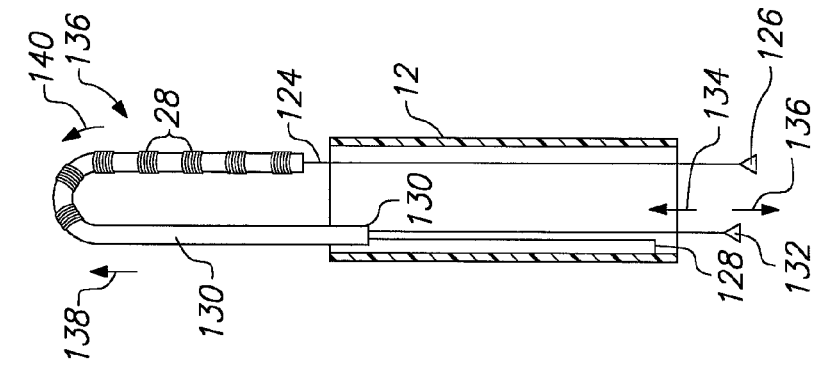
FIGS. 18, 19, and 20, are side sectional view, largely diagrammatic, showing an embodiment of the distal region shown in FIG. 1, in which the electrode array is movable.
Figure 19:
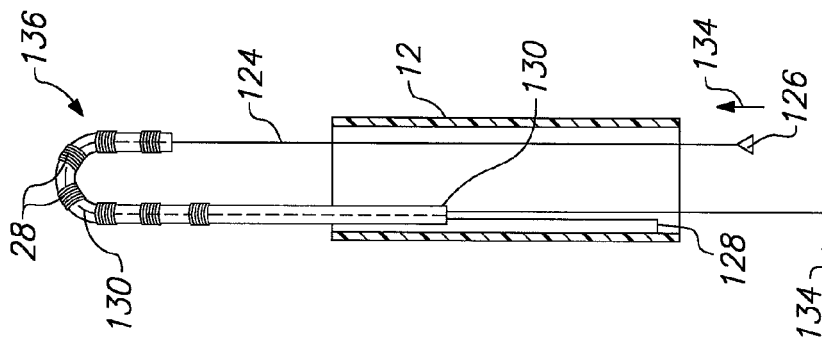
Figure 18:
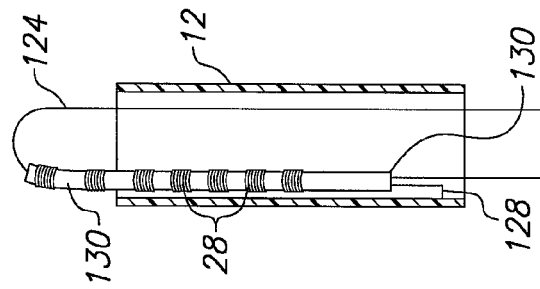

The embodiment shown in schematic form in FIGS. 18, 19, and 20 offers additional options for adjusting the nature and extent of contact between the electrode elements 28 and tissue. As FIG. 18 shows, a flexible spline leg 124 extends from an external push-pull control 126 through the catheter tube 12 and is looped back to a point of attachment 128 within the catheter tube 12. A sheath 130, made of an electrically insulating material, is slidable along the spline leg 124, both within and outside the catheter tube 12. The sheath 130 carries the electrode elements 28. The proximal end of the sheath 130 is attached to a push pull control 132 exposed outside the catheter tube 12.

By pushing both controls 126 and 132 simultaneously (arrows 134 in FIG. 19), both the spline leg 124 and the sheath 130 are deployed beyond the distal end 16 of the catheter tube 12. Together, the spline leg and sheath 130 form a loop structure 136 to present the electrode elements 28 for contact with tissue, in much the same way that the structure 100 and the structure 20, previously described, establish contact between the electrode elements 28 and tissue.

In addition, by holding the spline leg control 126 stationary while pushing or pulling the sheath control 132 (arrows 134 and 136 in FIG. 20), the physician is able to slide the sheath 130, and thus the electrode elements 28 themselves, along the spline leg 124 (as arrows 138 and 140 in FIG. 20 show). The physician is thereby able to adjustably locate the region and extent of contact between tissue and the electrode elements 28.

Furthermore, by holding the sheath control 132 stationary while pushing or pulling upon the spline leg control 126, the physician is able to adjust the length of the spline leg 124 exposed beyond the distal end 16 of the catheter tube 12. The physician is thereby able to incrementally adjust the radius of curvature in generally the same fashion previously described in the context of FIG. 17.

The arrangement in FIGS. 18, 19, and 20, thereby provides a wide range of adjustment options for establishing the desired degree of contact between tissue and the electrode elements 28 carried by the loop structure 136.

By pulling both controls 126 and 128 simultaneously (arrows 142 in FIG. 18), both the spline leg 124 and the sheath 130 are moved to a position close to or within the distal end 16 of the catheter tube 12 for introduction into a body region.

C. Free Pull Wire

FIG. 21 shows a multiple electrode support structure 144 formed from a spline leg 146 covered with an electrically insulating sleeve 148. The electrode elements 28 are carried by the sleeve 148.

The structure 144 is carried at the distal end 16 of a catheter tube 12, and comprises the distal part of a probe 10, in the manner shown in FIG. 1. In this respect, the structure 144 is like the structure 100, previously described, and the same materials as previously described can be used in making the structure 144.

Unlike the previously described structure 100, a slidable sheath 150 is intended to be moved along the catheter tube 12 and structure 144 between a forward position, covering the structure 144 for introduction into a body region (shown in FIG. 22), and an aft, retracted position, exposing the structure 144 for use (shown in FIGS. 21 and 23). Thus, unlike the structure 100, which is deployed by advancement forward beyond a stationary sheath 102, the structure 144 is deployed by being held stationary while the associated sheath 150 is moved rearward.

A pull wire 152 extends from the distal end 154 of the structure 144. In the illustrated embodiment, the pull wire 152 is an extension of the spline leg 146, thereby eliminating the need for an additional distal hub component to join the wire 152 to the distal structure end 154.

Unlike the structure 100, the pull wire 152 is not attached to the sheath 150. Instead, the catheter tube 12 includes an interior lumen 156, which accommodates sliding passage of the pull wire 152. The pull wire 152 passes through the lumen 156 to an accessible push-pull control 166, e.g., mounted on a handle 18 as shown in FIG. 1. When the structure 144 is free of the rearwardly withdrawn sheath 150, the physician pulls back on the wire 152 (arrow 168 in FIG. 23) to bend the structure 144 into a loop.

As FIGS. 21 and 23 show, the wire 152 may include a preformed region 158 adjacent to the distal structure end 154, wound into one or more loops, forming a spring. The region 158 imparts a spring characteristic to the wire 152 when bending the structure 144 into a loop. The region 158 mediates against extreme bending or buckling of the wire 152 during formation of the loop structure 144. The region 158 thereby reduces the likelihood of fatigue failure arising after numerous flex cycles.

FIG. 24 shows an alternative embodiment for the structure 144. In this embodiment, the distal structure end 154 includes a slotted passage 160, which extends across the distal structure end 154. In FIG. 24, the slotted passage 160 extends transverse of the main axis 162 of the structure 144. Alternatively, the slottage passage 160 could extend at other angles relative to the main axis 162.

Unlike the embodiment shown in FIGS. 21 to 23, the wire 152 in FIG. 24 is not an extension of the spline leg 146 of the structure 144. Instead, the wire 152 comprises a separate element, which carries a ball 164 at its distal end. The ball 164 is engaged for sliding movement within the slotted passage 160. The ball 164 also allows rotation of the wire 152 relative to the structure 144. The ball 164 and slotted passage 160 form a sliding joint, which, like the spring region 158 in FIGS. 21 to 23, reduces the likelihood of fatigue failure arising after numerous flex cycles.

As before described in the context of the structure 100, additional tissue contact forces between the structure 144 and tissue can be generated by mounting a bendable spring 64 in the distal end 16 of the catheter tube (see FIG. 21). Alternatively, or in combination with the manually bendable spring 64, the distal end 16 of the catheter tube 12 can be prebent to form an elbow (like elbow 70 shown in FIG. 11 in association with the structure 20) generally orthogonal or at some other selected angle to the loop structure 144.

D. Preformed Loop Structures

1. Single Loops

FIG. 25 shows an adjustable, preformed loop structure 170. The structure 170 is carried at the distal end 16 of a catheter tube 12, which is incorporated into a probe, as shown in FIG. 1.

The structure 170 includes a single, continuous, flexible spline element 172 having two proximal ends 174 and 176. One proximal end 174 is secured to the distal catheter tube end 16. The other proximal end 176 slidably passes through a lumen 178 in the catheter tube 12. The proximal end 176 is attached to an accessible push-pull control 180, e.g., mounted in the handle 18 shown in FIG. 1. The flexible spline element 172 is bent into a loop structure, which extends beyond the distal end 16 of the catheter tube 12. The spline element 172 can be preformed in a normally bowed condition to accentuate the loop shape.

The continuous spline element 172 can be formed from resilient, inert wire, like Nickel Titanium or 17-7 stainless steel, or from resilient injection molded inert plastic, or from composites. In the illustrated embodiment, the spline element 172 comprises a thin, rectilinear strip of resilient metal, plastic material, or composite. Still, other cross sectional configurations can be used.

As before described in connection with other structures, a sleeve 182 made of, for example, a polymeric, electrically nonconductive material, like polyethylene or polyurethane or PEBAX™ material is secured, e.g., by heat shrinking, adhesives, or thermal bonding about the spline element 172 in a region of the structure 170. The sleeve 182 carries one or more electrode elements 28, which can be constructed in manners previously described.

The structure 170 includes an interior wire 184. The interior wire can be made from the same type of materials as the spline element 172. The distal end of the wire 184 carries a cap 186, which is secured, e.g., by crimping or soldering or spot welding, to the wire 184. The cap includes a through passage 188 (see FIG. 26), through which the mid portion of the spline element 172 extends. The spline element 172 is slidable within the through passage 188. It should be appreciated that the wire 184 can be attached to the spline element 172 in other ways to permit relative movement, e.g., by forming a loop or eyelet on the distal end of the wire 184, through which the spline leg 172 passes. It should also be appreciated that the cap 186 can be secured to the spline leg 172, if relative movement is not desired.

The proximal end of the interior wire 184 slidably passes through a lumen 190 in the catheter tube 12 for attachment to an accessible push-pull control 192, e.g., also on a handle 18 like that shown in FIG. 1.

As FIG. 27 shows, pushing on the control 180 (arrow 194) or pulling on the control 180 (arrow 196) moves the spline element 172 to alter the shape and loop stresses of the structure 170. Likewise, pushing on the control 192 (arrow 198) or pulling on the control 192 (arrow 200) moves the interior wire 184 in the lumen 190, which applies force to the cap 186 in the midportion of the structure 172, and which further alters the shape and loop stresses of the structure 170.

In particular, manipulation of the controls 180 and 192 creates asymmetric geometries for the structure 170, so that the physician is able to shape the structure 170 to best conform to the interior contours of the body region targeted for contact with the electrode elements. Manipulation of the controls 180 and 192 also changes the back pressures, which urge the electrode elements 28 into more intimate contact with tissue.

As FIG. 28 shows, further variations in the shape of and physical forces within the structure 170 can be accomplished by bending the interior wire 184 along its axis. In one embodiment, the wire 184 is made from temperature memory wire, which bends into a preestablished shape in response to exposure to blood (body) temperature, and which straightens in response to exposure to room temperature. Bending the interior wire 184 imparts forces (through the cap 186) to bend the spline element 172 into, for example, an orthogonal orientation. This to better access the body region where the electrode elements 28 are to be located in contact with tissue.

Alternatively, one or more steering wires (not shown) can be attached to the interior wire 184. Coupled to an accessible control (not shown), e.g. on the handle 18, pulling on the steering wires bends the wire 184, in generally the same fashion that the steering wires 66 affect bending of the spring 64, as previously described with reference to FIG. 2A.

Figure 29:
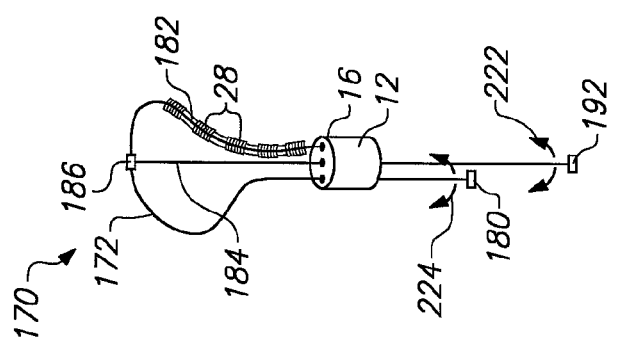
FIG. 29 is a side view of the distal region shown in FIG. 25, with the interior wire rotated about its axis to change the geometry of the preformed loop structure.

As FIG. 29 shows, the control 192 can also be rotated (arrows 222) to twist the interior wire 184 about its axis. Twisting the wire 184 imparts (through the cap 186) transverse bending forces along the spline element 172. The transverse bending forces form curvilinear bends along the spline element 172, and therefore along the electrode elements 28 as well. The loop stresses can also be further adjusted by causing the control 180 to rotate (arrows 224) the spline element 172.

Figure 31:
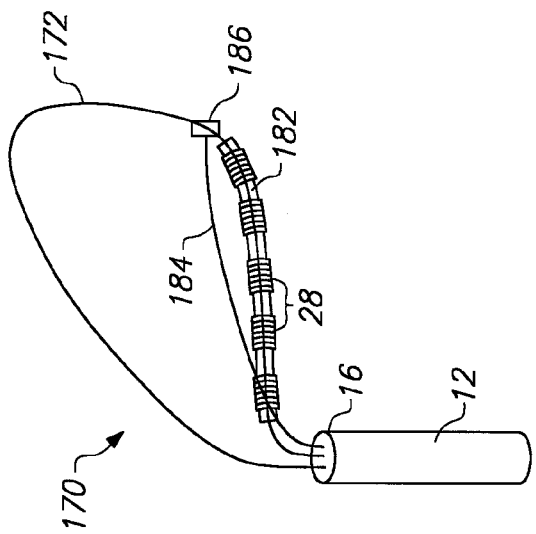
FIGS. 30 and 31 are side views of the distal region shown in FIG. 25, with the location of the slidable cap moved to change the geometry of the preformed loop structure.
Figure 30:
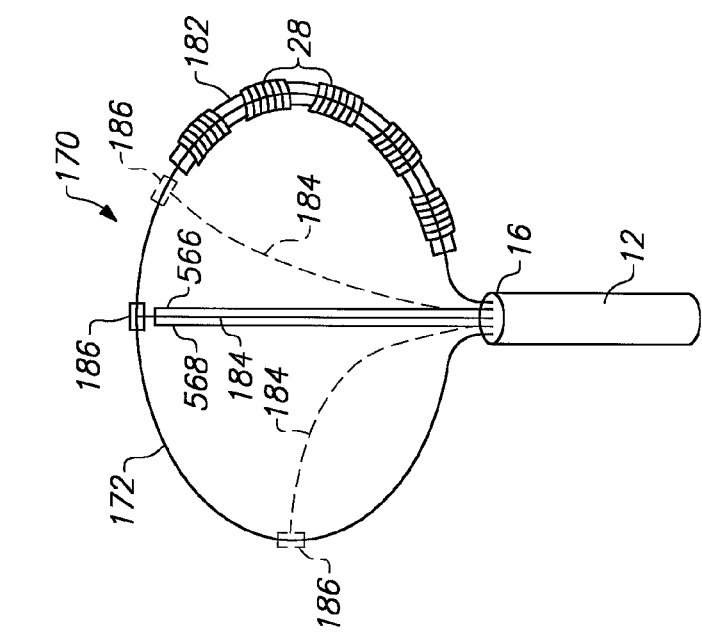

As FIG. 30 shows, the through passage cap 186 (see FIG. 26) permits the cap 186 to be repositioned along the spline element 172. In this way, the point where the wire 184 applies forces (either push-pull, or twisting, or bending, or a combination thereof) can be adjusted to provide a diverse variety of shapes (shown in phantom lines) for and loop stresses within the structure 170. FIG. 31 shows, by way of example, how changing the position of the cap 186 away from the midregion of the spline element 172 alters the orthogonal bend geometry of the spline element 172, compared to the bend geometry shown in FIG. 28. The cap 186 can be moved along the spline element 172, for example, by connecting steering wires 566 and 568 to the distal region of the interior wire 184. Pulling on a steering wire 566 or 568 will bend the interior wire 184 and slide the cap 186 along the spline element 172.

The single loop structure 170 is introduced into the targeted body region within an advanceable sheath 218, which is slidably carried about the catheter tube 12 (see FIG. 25). Movement of the sheath 218 forward (arrow 226 in FIG. 25) encloses and collapses the loop structure 170 within the sheath 218 (in generally the same fashion that the structure 144 in FIG. 21 is enclosed within the associated sheath 150). Movement of the sheath 218 rearward (arrow 230 in FIG. 25) frees the loop structure 170 of the sheath 218.

2. Multiple Loop Assemblies

Figure 32:
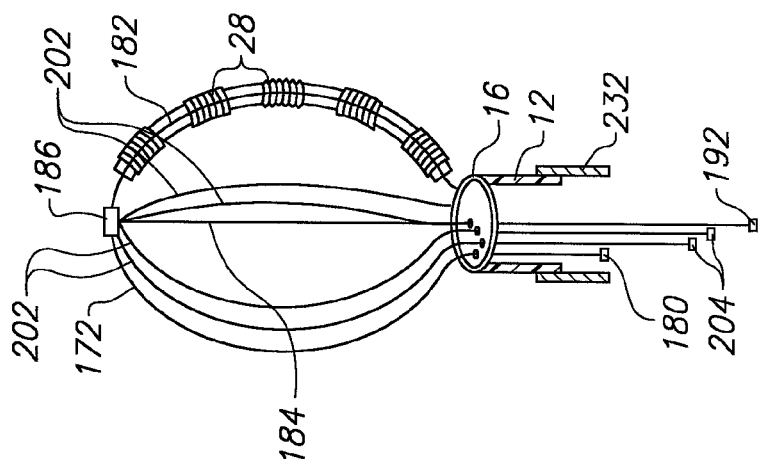
FIG. 32 is an enlarged, perspective side view of an alternative embodiment of the distal region of the probe shown in FIG. 1, showing a preformed, multiple spline loop structure.

As FIG. 32 shows, the structure 170 can include one or more auxiliary spline elements 202 in regions of the structure 170 spaced away from the electrode elements 28. In the illustrated embodiment, the auxiliary spline elements 202 slidably extend through the distal cap 186 as before described, and are also coupled to accessible controls 204 in the manner just described. In this way, the shape and loop stresses of the auxiliary spline elements 202 can be adjusted in concert with the spline element 172, to create further back pressures to urge the electrode 28 toward intimate contact with tissue. The existence of one or more auxiliary spline elements 202 in multiple planes also make it possible to press against and expand a body cavity, as well as provide lateral stability for the structure 170.

Figure 33:
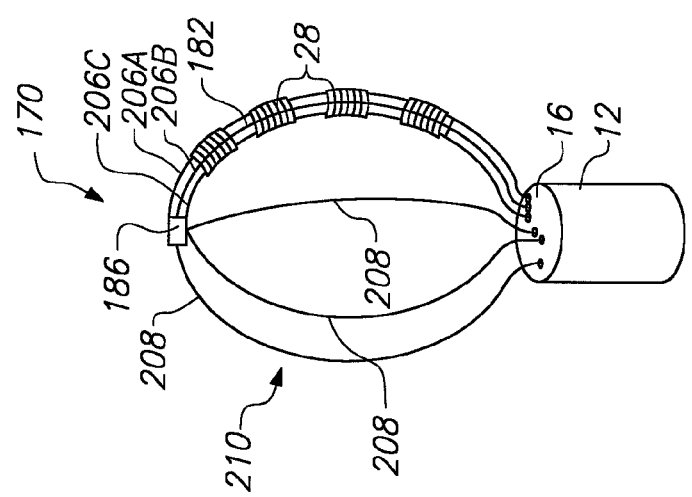
FIG. 33 is an enlarged, perspective side view of an alternative embodiment of the distal region of the probe shown in FIG. 32, showing a preformed, multiple spline loop structure with asymmetric mechanical stiffness properties.

As FIG. 33 shows, asymmetric mechanical properties can also be imparted to the structure 170, to improve contact between tissue and the electrode elements 28. In FIG. 33, the region of the structure 170 which carries the electrode elements 28 is stiffened by the presence of the closely spaced multiple spline elements 206 A, 206B, and 206C. Spaced apart, single spline elements 208 provide a back-support region 210 of the structure 170.

Figure 34:
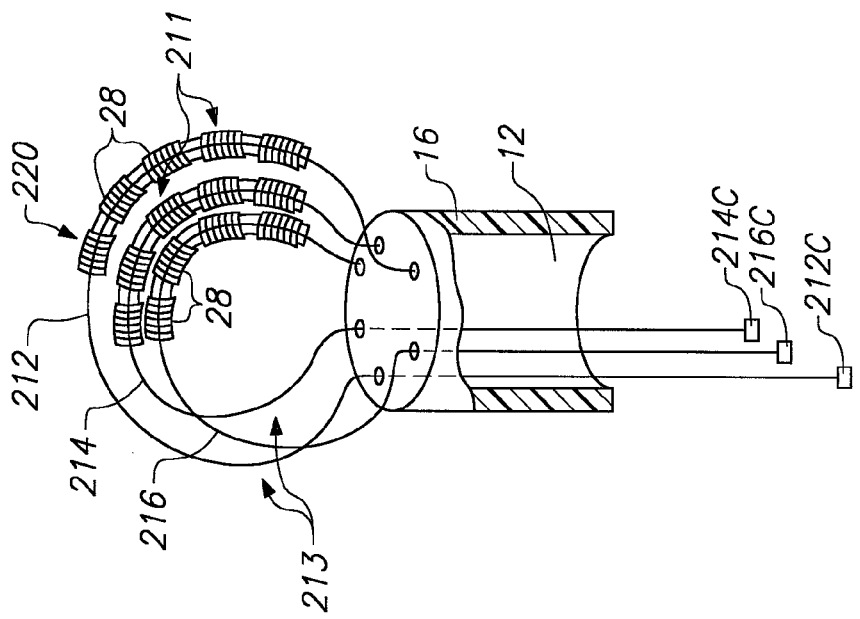
FIG. 34 is an enlarged, perspective side view of an alternative embodiment of the distal region of the probe shown in FIG. 1, showing a preformed, multiple independent spline loop structures.

FIG. 34 shows a multiple independent loop structure 220. The structure 220 includes two or more independent spline elements (three spline elements 212, 214, and 216 are shown), which are not commonly joined by a distal cap. The spline elements 212, 214, and 216 form independent, nested loops, which extend beyond the distal end 16 of the catheter tube 12.

A region 211 on each spline element 212, 214, and 216 carries the electrode elements 28. The other region 213 of each spline element 212, 214, and 216 is slidable within the catheter tube 12, being fitted with accessible controls 212C, 214C, and 216C, in the manner just described. Thus, independent adjustment of the shape and loop stresses in each spline element 212, 214, and 216 can be made, to achieve desired contact between tissue and the electrode elements 28.

Like the single loop structures shown in FIGS. 25 to 31, the various multiple loop structures shown in FIGS. 32 to 34 can be introduced into the targeted body region in a collapsed condition within a sheath 232 (see FIG. 32), which is slidably carried about the catheter tube 12. As FIG. 32 shows, movement of the sheath 232 away from the loop structure frees the loop structure for use.

E. Orthogonal Loop Structures

FIGS. 28 and 31 show embodiments of loop structures 170, which have been bent orthogonally to the main axis of the structure 170. In these embodiments, the orthogonal bending is in response to bending an interior wire 184.

FIGS. 35 and 36 show a loop structure 232 that assumes an orthogonal geometry (in FIG. 36) without requiring an interior wire 184. The structure 232, like the structure 170 shown in FIG. 25, is carried at the distal end 16 of a catheter tube 12, which is incorporated into a probe, as shown in FIG. 1.

Like the structure 170, the structure 232 comprises a single, continuous, flexible spline element 234. One proximal end 236 is secured to the distal catheter tube end 16. The other proximal end 238 passes through a lumen 240 in the catheter tube 12. The proximal end 238 is attached to an accessible control 242, e.g., mounted in the handle 18 shown in FIG. 1. As in the structure 170, the spline element 234 can be preformed in a normally bowed condition to achieve a desired loop geometry.

In FIGS. 35 and 36, the spline element 234 is formed, e.g., from inert wire, like Nickel Titanium or 17-7 stainless steel, or from resilient injection molded inert plastic, with two regions 244 and 246 having different cross section geometries. The region 244, which comprises the exposed part of the spline element 234 that carries the electrode elements 28, possesses a generally rectilinear, or flattened cross sectional geometry, as FIG. 37 shows. The region 246, which comprises the part of the spline element 234 extending within the catheter tube 12 and attached to the control 240, possesses a generally round cross sectional geometry, as FIG. 38 shows. To provide the two regions 244 and 246, a single length of round wire can be flattened and annealed at one end to form the rectilinear region 244.

Rotation of the control 242 (attached to the round region 246) (arrows 250 in FIG. 35) twists the rectilinear region 244 about the proximal end 236, which being fixed to the catheter tube 12, remains stationary. The twisting rectilinear region 244 will reach a transition position, in which the region 244 is twisted generally 90° from its original position (as FIG. 39 shows). In the transition position, the loop structure 232 bends orthogonal to its main axis, as FIG. 36 shows. By stopping rotation of the control 242 once the transition position is reached, the retained twist forces in the loop structure 232 hold the loop structure 232 in the orthogonally bent geometry.

FIGS. 42A and 42B show an alternative embodiment, in which each leg 554 and 556 of a loop structure 558 is attached to its own individual control, respectively 560 and 562. The region 564 of the loop structure 558 carrying the electrode element 28 possesses a generally rectilinear or flattened cross section. The regions of the legs 554 and 556 near the controls 560 and 562 possess generally round cross sections. Counter rotation of the controls 560 and 562 (respectively arrows 561 and 563 in FIG. 42B), twists the rectilinear region 564 to bend the loop structure 558 generally orthogonal to its axis (as FIG. 42B shows). The counter rotation of the controls 560 and 562 can be accomplished individually or with the inclusion of a gear mechanism.

In both embodiments shown in FIGS. 36 and 42B, once the orthogonal bend is formed and placed into contact with tissue, controlled untwisting of the spline legs will begin to straighten the orthogonal bend in the direction of tissue contact. Controlled untwisting can thereby be used as a counter force, to increase tissue contact.

The characteristics of the orthogonally bent geometry depend upon the width and thickness of the rectilinear region 244. As the ratio between width and thickness in the region 244 increases, the more pronounced and stable the orthogonal deflection becomes.

The diameter of the loop structure 232 also affects the deflection. The smaller the diameter, the more pronounced the deflection. Increases in diameter dampen the deflection effect. Further increases beyond a given maximum loop diameter cause the orthogonal deflection effect to be lost.

The characteristics of the electrical insulation sleeve 248, which carries the electrode elements 28, also affect the deflection. Generally speaking, as the stiffness of the sleeve 248 increases, the difficulty of twisting the region 244 into the transition position increases. If the sleeve 248 itself is formed with a non-round cross section, e.g. elliptical, in the rectilinear region 244 the orthogonal deflection characteristics are improved.

The orthogonal deflection effect that FIGS. 35 and 36 show can also be incorporated into the loop structure of the type previously shown in FIG. 14. In this embodiment (see FIG. 40), the loop structure 252 comprises a spline leg 254 (see FIG. 41 also) enclosed within an electrically conductive sleeve 256, which carries the electrode elements 28. The distal end of the structure 252 is attached by a joint wire 260 to a sheath 258. As previously described, advancing the structure 252 from the sheath 258 forms a loop (as FIG. 40 shows).

In the embodiment shown in FIG. 40, the spline leg 254 is rectilinear in cross section (see FIG. 41). Furthermore, as FIG. 41 shows, the spline leg 254 is preformed in a normally twisted condition, having two sections 262 and 264. The section 262 is distal to the section 264 and is attached to the joint wire 260. The sections 262 and 264 are arranged essentially orthogonally relative to each other, being offset by about 90°. When advanced outside the sheath 258, the twisted bias of the rectilinear spline leg 254 causes the formed loop structure 252 to bend orthogonally to its main axis, as FIG. 40 shows.

Figure 43:
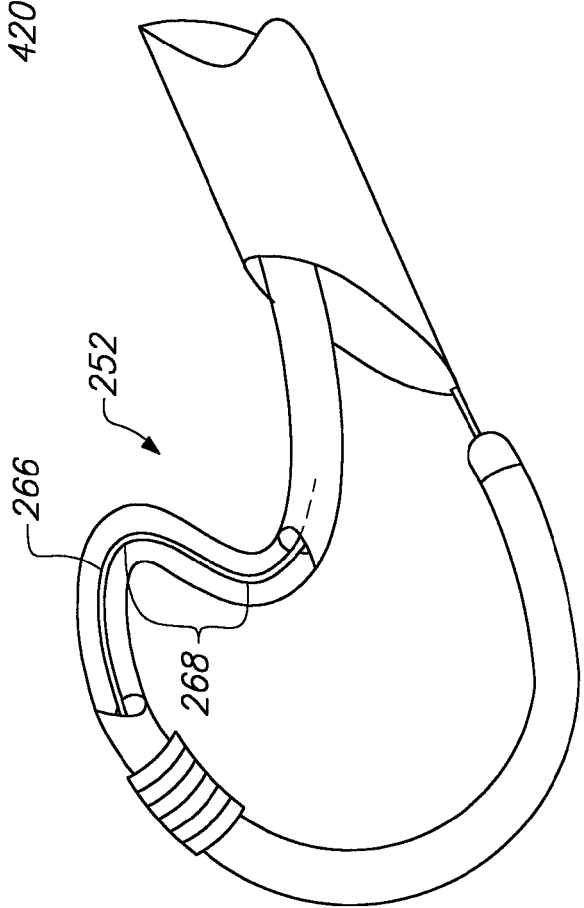
FIG. 43 is an enlarged side perspective view of an alternative embodiment of the distal region of the probe shown in FIG. 1, showing a preformed loop structure, which has a prestressed interior spline forming an orthogonal bend.

In an alternative embodiment (see FIG. 43), the structure 252 can include a spline leg 266 preformed to include along its length one or more stressed elbows 268. The prestressed elbows 268 impart an orthogonal deflection when the structure 252 is free of the constraint of the sheath 270. When housed within the sheath 270, the stiffness of the sheath 270 straightens the elbows 268.

F. Deployment of Flexible Loop Structures

1. Generally

Various access techniques can be used to introduce the previously described multiple electrode structures into a desired region of the body. In the illustrated embodiment (see FIG. 44), the body region is the heart, and the multiple electrode structure is generally designated ES.

During introduction, the structure ES is enclosed in a straightened condition within its associated outer sheath (generally designated S in FIG. 44) at the end 16 of the catheter tube 12. To enter the right atrium of the heart, the physician directs the catheter tube 12 through a conventional vascular introducer (designated with a capital-I in FIG. 44) into, e.g., the femoral vein. For entry into the left atrium, the physician can direct the catheter tube 12 through a conventional vascular introducer retrograde through the aortic and mitral valves, or can use a transeptal approach from the right atrium.

Once the distal end 16 of the catheter tube 12 is located within the selected chamber, the physician deploys the structure ES in the manners previously described, i.e., either by advancing the structure ES forward through the sheath S (e.g., as in the case of the structures shown in FIG. 3 or 15) or by pulling the sheath S rearward to expose the structure ES (e.g., as in the case of the structures shown in FIG. 21 or 25).

It should be appreciated that the structure ES discussed above in the context of intracardiac use, can also be directly applied to the epicardium through conventional thoracotomy or thoracostomy techniques.

2. Loop Structures

The various loop structures previously described (shown in FIGS. 1 to 31), when deployed in the left or right atrium tend to expand the atrium to its largest diameter in a single plane. The loop structure tends to seek the largest diameter and occupy it. The loop structures can also be adapted to be torqued, or rotated, into different planes, and thereby occupy smaller regions.

The addition of auxiliary splines, such as shown in FIGS. 32 to 34 serves to expand the atrium in additional planes. The auxiliary splines also make it possible to stabilize the structure against a more rigid anatomic structure, e.g. the mitral valve annulus in the left atrium, while the spline carrying the electrode elements loops upward toward anatomic landmarks marking potential ablation sites, e.g., tissue surrounding the pulmonary veins.

The various structures heretofore described, which exhibit compound or orthogonal bends (see, e.g., FIGS. 28, 31, 35, 40, 42, and 43) (which will be referred to as a group as "Compound Bend Assemblies") also make it possible to locate the ablation and/or mapping electrode(s) at any location within a complex body cavity, like the heart. With prior conventional catheter designs, various awkward manipulation techniques were required to position the distal region, such as prolapsing the catheter to form a loop within the atrium, or using anatomical barriers such as the atrial appendage or veins to support one end of the catheter while manipulating the other end, or torquing the catheter body. While these techniques can still be used in association with the compound bend assemblies mentioned above, the compound bend assemblies significantly simplify placing electrode(s) at the desired location and thereafter maintaining intimate contact between the electrode(s) and the tissue surface. The compound bend assemblies make it possible to obtain better tissue contact and to access previously unobtainable sites, especially when positioning multiple electrode arrays.

Compound bend assemblies which provide a proximal curved section orthogonal to the distal steering or loop geometry plane allow the physician to access sites which are otherwise difficult and often impossible to effectively access with conventional catheter configurations, even when using an anatomic barrier as a support structure. For example, to place electrodes between the tricuspid annulus and the cristae terminalis perpendicular to the inferior vena cava and superior vena cava line, the distal tip of a conventional the catheter must be lodged in the right ventricle while the catheter is torqued and looped to contact the anterior wall of the right atrium. Compound bend assemblies which can provide a proximal curved section orthogonal to the distal steering or loop geometry plane greatly simplify positioning of electrodes in this orientation. Compound bend assemblies which provide a proximal curved section orthogonal to the distal steering or loop geometry plane also maintain intimate contact with tissue in this position, so that therapeutic lesions contiguous in the subepicardial plane and extending the desired length, superiorly and/or inferiorly oriented, can be accomplished to organize and help cure atrial fibrillation.

A transeptal approach will most likely be used to create left atrial lesions. In a transeptal approach, an introducing sheath is inserted into the right atrium through the use of a dilator. Once the dilator/sheath combination is placed near the fossa ovalis under fluoroscopic guidance, a needle is inserted through the dilator and is advanced through the fossa ovalis. Once the needle has been confirmed to reside in the left atrium by fluoroscopic observation of radiopaque contrast material injected through the needle lumen, the dilator/sheath combination is advanced over the needle and into the left atrium. At this point, the dilator is removed leaving the sheath in the left atrium.

A left atrial lesion proposed to help cure atrial fibrillation originates on the roof of the left atrium, bisects the pulmonary veins left to right and extends posteriorly to the mitral annulus. Since the lesion described above is perpendicular to the transeptal sheath axis, a catheter which can place the distal steering or loop geometry plane perpendicular to the sheath axis and parallel to the axis of the desired lesion greatly enhances the ability to accurately place the ablation and/or mapping element(s) and ensures intimate tissue contact with the element(s). To create such lesions using conventional catheters requires a retrograde procedure. The catheter is advanced through the femoral artery and aorta, past the aortic valve, into the left ventricle, up through the mitral valve, and into the left atrium. This approach orients the catheter up through the mitral valve. The catheter must then be torqued to orient the steering or loop geometry plane parallel to the stated lesion and its distal region must be looped over the roof of the left atrium to position the ablation and/or mapping element(s) bisecting the left and right pulmonary veins and extending to the mitral annulus.

Preformed guiding sheaths have also been employed to change catheter steering planes. However, preformed guiding sheaths have been observed to straighten in use, making the resulting angle different than the desired angle, depending on the stiffness of the catheter. Furthermore, a guiding sheath requires a larger puncture site for a separate introducing sheath, if the guiding sheath is going to be continuously inserted and removed. Additional transeptal punctures increase the likelihood for complications, such as pericardial effusion and tamponade.

G. Loop Size Marking

FIG. 87 shows a probe 524 comprising a catheter tube 526 carrying a slotted sheath 528 of the type previously described and shown, e.g., in FIG. 1. The catheter tube 526 includes proximal handle 529 and a distal multiple electrode array 530. The multiple electrode array 530 is deployed as a loop structure from the slotted sheath 528, in the manner previously described and shown, e.g., in FIG. 3A.

In FIG. 87, the probe 524 includes indicia 532 providing the physician feedback on the size of the formed loop structure. In FIG. 87, the indicia 532 comprises markings 534 on the region of the catheter tube 526 extending through the proximal end of the sheath 528. The markings 534 indicate how much of the catheter tube 526 has been advanced through the sheath 528, which thereby indicates the size of the formed loop structure.

The markings 534 can be made in various ways. They can, for example, be placed on the catheter tube 526 by laser etching, or by printing on the catheter tube 526 using biocompatible ink, or by the attachment of one or more premarked, heat shrink bands about the catheter tube 526.

In FIG. 88, the slotted sleeve 528 is attached to the handle 529 of the probe 524. In this arrangement, the catheter tube 526 is advanced and retracted through the slotted sheath 528 by a push-pull control 536 on the handle 529. In this embodiment, the indicia 532 providing feedback as to the size of the formed loop structure includes markings 536 on the handle 529, arranged along the path of travel of the push-pull control 536. The markings 536 can be applied to the handle 529, e.g., by laser etching to printing. As in FIG. 87, the markings 536 indicate how much of the catheter tube 526 has been advanced through the slotted sheath 528.

G. Movable Steering

FIG. 89 shows a movable steering assembly 570. The assembly 570 includes a bendable wire 572 with at least one attached steering wire (two wires 574 and 576 are shown). The steering wires 574 and 576 are attached, e.g. by spot welding or soldering, to the bendable wire 572. The bendable wire 572 can be formed from resilient, inert wire, like Nickel Titanium or 17-7 stainless steel, or from resilient injection molded inert plastic, or from composites. In the illustrated embodiment, the wire 572 comprises a rectilinear strip of resilient metal, plastic material, or composite. Still, other cross sectional configurations can be used. The distal end 598 of the wire 572 is formed as a ball or another blunt, nontraumatic shape.

The steering wires 574 and 576 are attached to an accessible control 584. The control 584 can take the form, for example, of a rotatable cam wheel mechanism of the type shown in Lundquist and Thompson U.S. Pat. No. 5,254,088, which is already incorporated into this Specification by reference. Pulling on the steering wires 574 and 576 (arrows 600 in FIG. 89), e.g., by rotating the control 584, bends the wire 572 in the direction of the pulling force.

The bendable wire 572 is attached by a ferrule 580 to a guide coil 578. The guide coil 578 provides longitudinal support for the bendable wire 572. The guide coil 578 acts as the fulcrum about which the steering assembly 570 bends.

The assembly 570, comprising the bendable wire 572, steering wires 574 and 576, and guide coil 578, is carried within an outer flexible tube 582. Operation of the control 584, to deflect the wire 572 within the tube 582, bends the tube 582.

Taking into account the rectilinear shape of the bendable wire 572, the outer tube 582 is ovalized. The interference between the rectilinear exterior shape of the wire 572 and the oval interior shape of the tube 582 prevents rotation of the wire 572 within the tube 582. The interference thereby retains a desired orientation of the bendable wire 572 with respect to the tube 582, and thus the orientation of the applied bending forces.

The assembly 570 is attached to an accessible control 582. Pushing and pulling on the control 570 (arrows 602 and 604 in FIG. 89) axially moves the steering assembly 570 within the tube 582. Axial movement of the assembly 570 changes the axial position of the bendable wire 572 within the tube 582. The control 570 thereby adjusts the location where bending forces are applied by the wire 572 along the axis of the tube 582.

FIGS. 90 and 91 show the movable steering assembly 570 incorporated into a loop structure 586 of the type previously disclosed with reference to FIG. 25, except there is no interior wire 184. The loop structure 586 includes a spline 588 (see FIG. 91), which forms a loop. A sleeve 590 surrounds the spline 588. One or more electrode elements 28 are carried by the sleeve 590.

As FIG. 91 shows, the sleeve 590 includes an ovalized interior lumen 592, which carries the movable steering assembly 570. The steering assembly 570, attached to the accessible control 582, is movable within the lumen 592 along the spline 588, in the manner just described with respect to the ovalized tube 582 in FIG. 89.

As FIG. 92 shows, operating the control 584 to actuate the steering wires 574 and 576 exerts a bending force (arrow 604) upon the spline 588 (through the bendable wire 572). The bending force alters the shape of the loop structure 586 in the plane of the loop, by increasing or decreasing its diameter. Shaping the loop structure 586 using the steering mechanism 570 adjusts the nature and extent of tissue contact.

Because the steering mechanism 570 is movable, the physician can selectively adjust the location of the bending force (arrow 604) to take into account the contour of the tissue in the particular accessed body region.

As FIG. 93 shows, the loop structure 586 can carry more than one movable steering mechanism. In FIG. 93, there are two moveable steering mechanisms, designated 570(1) and 570(2), one carried on each leg of the structure 586. A separate steering control designated 584(1) and 584(2), and a separate axial movement control, designated 582(1) and 582(2) can also be provided. It is therefore possible to independently adjust the position of each steering mechanism 570(1) and 570(2) and individually apply different bending forces, designated, respectively, arrows 604(1) and 604(2). The application of individually adjustable bending forces (arrows 604(1) and 604(2)) allow diverse changes to be made to the shape of the loop structure 586.

It should also be appreciated that the movable steering mechanism 570 can be incorporated into other loop structures including those of the type shown in FIG. 33.

II. Self-Anchoring Multiple Electrode Structures

1. Integrated Branched Structures

FIGS. 45 and 46 show an integrated branched structure 272, which comprises an operative branch 274 and an anchoring branch 276 oriented in an angular relationship. The branched structure 274 occupies the distal end 16 of a catheter tube 12, and forms the distal part of a probe 10, as shown in FIG. 1.

It should be appreciated that there may be more than one operative branch or more than one anchoring branch. The two branches 274 and 276 are shown and described for the purpose of illustration.

The operative branch 274 carries one or more operative elements. The operative elements can take various forms. The operative elements can be used, e.g., to sense physiological conditions in and near tissue, or to transmit energy pulses to tissue for diagnostic or therapeutic purposes. As another example, the operative elements may take the form of one or more tissue imaging devices, such as ultrasound transducers or optical fiber elements. By way of further example, the operative elements can comprise biopsy forceps or similar devices, which, in use, handle tissue. The operative elements can also comprise optical fibers for laser ablation, or a fluorescence spectroscopy device.

In the illustrated embodiment, the operative elements take the form of the electrode elements 28 (as previously described). In use, the electrode elements 28 contact tissue to sense electrical events, or to transmit electrical pulses, e.g., to measure the impedance of or to pace heart tissue, or to transmit electrical energy to ablate tissue.

In the illustrated embodiment, the operative branch 274 comprises a spline element 282 enclosed within an electrically insulating sleeve 284. The spline element 282 can be formed, e.g., from resilient, inert wire, like Nickel Titanium or 17-7 stainless steel, or from resilient injection molded inert plastic. In the illustrated embodiment, the spline element 282 comprises a thin, rectilinear strip of resilient metal or plastic material. Still, other cross sectional configurations can be used. Furthermore, more than a single spline element may be used.

As before described in the context of other structures, a sleeve 282 made of, for example, a polymeric, electrically nonconductive material, like polyethylene or polyurethane or PEBAX™ material is secured about the spline element 282.

The sleeve 282 carries the electrode elements 28, which can also be constructed in manners previously described.

In the illustrated embodiment, the operative branch 274 extends at about a 45° angle from the anchoring branch 276. Various other angles between 0° (i.e., parallel) and 90° (i.e., perpendicular) can be used.

The angular relationship between the operative branches 274 and the anchoring branch 276 causes the operative branch 274 to inherently exert force against tissue as it is advanced toward it. The spline element 282, or the sleeve 284, or both, can be stiffened to bias the operative branch 274 toward the anchoring branch 276, to thereby enhance the inherent tissue contact force.

As FIG. 46 best shows, the anchoring branch 276 comprises a tubular body 286 defining an interior lumen 288, which extends through the catheter tube 12. The distal end 290 of the body 286 may be extended outward beyond the distal end 16 of the catheter tube 12, generally along the same axis 292 as the catheter tube 12. The proximal end 296 of the body 286 communicates with an accessible inlet 294, e.g., located on the catheter tube 12 or on the handle 18.

The inlet 294 accommodates passage of a conventional guide wire 306 into and through the lumen 288. The guide wire 306 includes a blunt distal end 308 for nontraumatic contact with tissue.

As FIG. 47 shows, the body 286 can be carried within the catheter tube 12 for sliding movement forward (arrow 298) or rearward (arrow 300). In this embodiment, an accessible control 302, e.g., located on the handle 18, is coupled to the body 286 to guide the movement. In this way, the physician can withdraw the body 286 within the catheter tube 12 during introduction of the structure 272 into the body region. The physician can also adjust the relative length of the body 286 beyond the distal end 16 of the catheter tube 16 to aid in positioning and anchoring the structure 272, once deployed within the targeted body region.

An exterior sheath 304 is slidable along the catheter tube 12 between a forward position (FIG. 48) and a rearward position (FIG. 45). In the forward position, the sheath 304 encloses and shields the operative branch 274, straightening it. When in the forward position, the sheath 304 also encloses and shields the anchoring branch 274. In the rearward position, the sheath 304 frees both branches 274 and 276 for use.

In use within the heart (see FIGS. 49A, 49B, and 49C), the physician maneuvers the guide wire 306 through and outwardly of the lumen 288, with the aid of fluoroscopy or imaging, to a desired anchor site. FIGS. 50A and 50B show candidate anchor sites within the heart, which surround anatomic structures that most commonly develop arrhythmia substrates, such as the superior vena cava SVC; right pulmonary veins (RPV); and left pulmonary veins (LPV); inferior vena cava (IVC); left atrial appendage (LAA); right atrial appendage (RAA); tricuspid annulus (TA); mitral annulus (MA); and transeptal puncture (TP). The physician positions the blunt end portion 308 near tissue at the anchor site (see FIG. 49A).

As FIG. 49B shows, the physician advances the structure 272, enclosed within the sheath 304, along the anchored guide wire 306. When near the anchor site, the physician retracts the sheath 304, freeing the structure 272.

As FIG. 49C shows, the physician advances the anchoring branch 276 along the guide wire 306 into the anchor site. The anchoring branch 276 provides a support to place the operative branch 274 in contact with tissue in the vicinity of the anchor site.

Radiopaque makers 326 can be placed at preestablished positions on the structure 272 for visualization under fluoroscopy, to thereby aid in guiding the structure 272 to the proper location and orientation.

FIG. 55 shows an alternative embodiment of the anchoring branch 276. In this embodiment, the anchoring branch 276 carries an inflatable balloon 346 on its distal end. The balloon 346 is inflated to secure the attachment of the anchoring branch 276 to the targeted vessel or cavity anchor site. The anchoring branch 276 includes a lumen 352 that extends through the balloon 346, having an inlet 348 at the distal end of the balloon 346 and an outlet 350 at the proximal end of the balloon 346. The lumen 352 allows blood to flow through the targeted vessel or cavity anchor site, despite the presence of the anchoring balloon 346. The lumen 306 also allows passage of the guide wire 306 for guiding the anchoring branch 276 into position.

As FIG. 46 shows, the operative branch 274 can carry one or more steering wires 310 coupled to a bendable spring 312. Coupled to an accessible control 314, e.g. on the handle 18, pulling on the steering wires 310 bends the spring 312, in generally the same fashion that the steering wires 66 affect bending of the spring 64, as previously described with reference to FIG. 2A. The physician is thereby able to affirmatively bend the operative branch 274 relative to the anchoring branch 276 to enhance site access and tissue contact. The steering wires 310 can be coupled to the spring 312 to affect bending in one plane or in multiple planes, either parallel to the catheter axis 292 or not parallel to the axis 292.

Alternatively, or in combination with the manually bendable spring 312, the spline element 282 can be prebent to form an elbow (like elbow 70 shown in FIG. 11 in association with the structure 20) generally orthogonal or at some other selected angle to the axis 292 of the catheter tube 12. The spline element 282 can also be prebent into a circular or elliptical configuration. For example, a circular configuration can be used to circumscribe the pulmonary veins in the left atrium.

Alternatively, or in combination with a bendable operative branch 274, the distal end 16 of the catheter tube 12 can include an independent steering mechanism (see FIG. 49C), e.g., including a bendable wire 64 and steering wires 66, as previously described and as also shown in FIG. 2A. By steering the entire distal end 16, the physician orients the branched structure 272 at different angles relative to the targeted anchor site.

2. Slotted Branch Structures

FIG. 51 shows an embodiment of a branched structure 272, in which the operative branch 274 can be moved in an outward direction (arrow 316) and an inward direction (arrow 318) relative to the catheter tube 12. In this embodiment, the operative branch 274 comprises a tubular body 322, which slidably extends through a lumen 324 in the catheter tube 12. An accessible control 328 on the proximal end of the body 322 guides the sliding movement.

The spline element 282, insulating sleeve 284, and operative elements (i.e., electrode elements 28), already described, are carried at the distal end of the slidable body 322. The catheter tube 12 includes a slot 320 near the distal end 16, through which the slidable body 322 passes during outward and inward movement 316 and 318.

The ability to move the operative branch 274 outside the catheter tube 12 enables the physician to define the number of electrodes 28 contacting the tissue, and thereby define the length of the resulting lesion. Alternatively, a movable operative branch 274 allows the physician to drag a selected activated electrode element 28 along tissue, while the anchoring branch 276 provides a stationary point of attachment.

The slidable body 322 can also be attached and arranged for rotation (arrows 352 in FIG. 51) with respect to the catheter tube 12, if desired, by making the exterior contour of the slidable body 322 and the interior of the lumen 324 matching and symmetric. Rotation of the slidable body 322 can be prevented or restricted, if desired, by providing an exterior contour for the slidable body 322 that is asymmetric, and sliding the body 322 through a matching asymmetric anchor or lumen within the slot 320 or within the catheter tube 12.

As FIG. 51 shows, radiopaque makers 326 are placed near the slot 320 and near the distal tip of the operative element 274 for visualization under fluoroscopy. The markers 326 can be located at other parts of the structure 274, as well, to aid in manipulating the operative branch 274 and anchoring branch 276.

The operative branch 274 shown in FIG. 51 can include a steering spring and steering wires in the manner previously shown and described in FIG. 46. All other mechanisms also previously described to bend the operative branch 274 in planes parallel and not parallel to the catheter axis 292 can also be incorporated in the FIG. 51 embodiment.

FIG. 52 shows an embodiment, like FIG. 51, except that the catheter body 12 also carries an accessible control 330 to rotate the slot 320 about the catheter tube axis 292 (arrows 352 in FIG. 52). If the operative branch 272 is free to rotated upon itself (as previously described), and if the spline element 282 within the operative branch 274 is circular in cross section, the operative branch 274 will rotate upon itself during rotation of the slot 320. In this arrangement, rotation of the slot 320 torques the operative branch about the catheter tube axis 292.

On the other hand, if the spline element 282 within the operative branch 274 is rectangular in cross section, the operative branch 274 will rotate upon itself during rotation of the slot 320, provided that rotation of the operative branch 274 about its axis is not prevented, and provided that the angle (α in FIG. 52) between the axis 332 of the operative branch 274 and the axis 292 of the catheter tube 12 is less than 20°. Otherwise, an operative branch 274 with a rectilinear spline element 282, will not rotate upon itself during rotation of the slot 320, and thus can not be torqued by rotation of the slot 320.

FIG. 53 shows an embodiment of the structure 272, which like FIG. 51, allows movement of the operative branch 274 through a slot 320. Unlike the embodiment in FIG. 51, the embodiment shown in FIG. 53 includes a pull wire 334 attached to the distal end 336 of the operative branch 274. The pull wire 334 passes through the exterior sheath 304 or through the catheter tube 12 (previously described) to an accessible stop 336. Advancing the operative branch 274 forward (arrow 338) through the slot 320, while holding the pull wire 334 stationary, bends the operative branch 274 into a loop, in much the same manner previously described in connection with the FIG. 15A embodiment. Pulling on the wire 334 (arrow 342) reduces the amount of exposed length beyond the distal end of the sheath 304. By advancing the catheter tube (arrow 340), the radius of curvature of the looped operative branch 274 can be adjusted, in much the same way previously shown in the FIG. 17A embodiment.

FIG. 54 shows an embodiment of the structure 272, which like FIG. 51, allows movement of the operative branch 274 through a slot 320. Unlike the embodiment in FIG. 51, the embodiment shown in FIG. 53 includes a flexible joint 344 which joins the distal end 336 of the operative branch 274 to the distal end 16 of the catheter tube 12. Advancing the operative branch 274 forward (arrow 338) through the slot 320, bends the operative branch 274 into a loop, in much the same manner previously described in connection with the FIGS. 3 and 15 embodiments. The flexible joint 344 can comprise a plastic material or a metal material, as the preceding FIGS. 3 and 15 embodiments demonstrate.

3. Spanning Branch Structures

Figure 56:
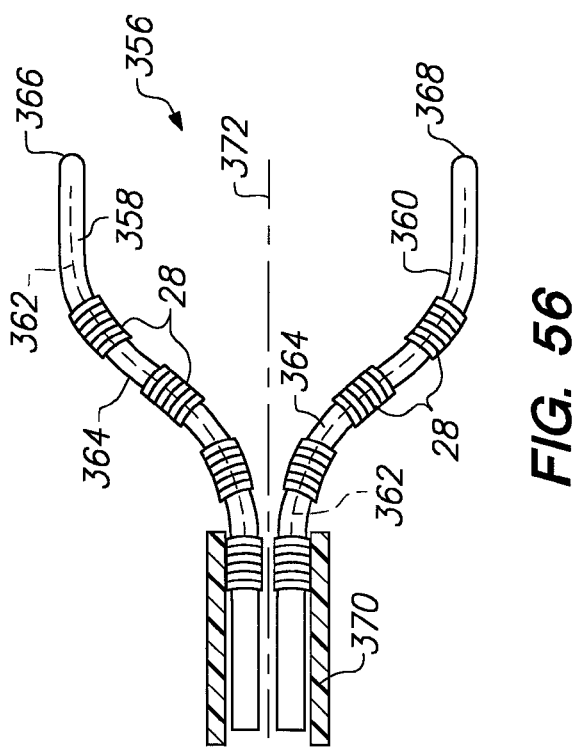
FIG. 56 is a side view of an alternative embodiment of the distal region of the probe shown in FIG. 1, showing a spanning branch structure.

FIG. 56 shows a self-anchoring multiple electrode structure 356 comprising multiple operative branches (two operative branches 358 and 360 are shown in FIG. 56). Like the operative branch 274 shown in FIG. 45, each operative branch 358 and 360 carries one or more operative elements, which can take various forms, and which in the illustrated embodiment comprise the electrode elements 28. Each operative branch 358 and 360 likewise comprises a spline element 362 enclosed within an electrically insulating sleeve 364, on which the electrode elements 28 are carried.

Figure 57:
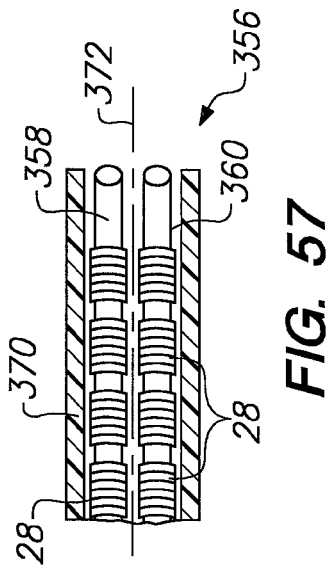
FIG. 57 is a side sectional view of the spanning branch structure shown in FIG. 56, with the associated sheath advanced.

In the illustrated embodiment, the operative branches 358 and 360 are jointly carried within a catheter sheath 370. Each operative branch 358 and 360 is individually slidable within the sheath 370 between a deployed position (FIG. 56) and a retracted position (FIG. 57). It should be appreciated that each operative branch 358 and 360 can be deployed and retracted in an individual sheath.

Each operative element 358 and 360 includes a distal region, respectively 366 and 368, which are mutually bent outward in a "bow-legged" orientation, offset from the main axis 372 of the sheath 370. This outwardly bowed, spaced apart relationship between the regions 366 and 368 can be obtained by prestressing the spline elements 362 into the desired shape, or by providing a spring which is actively steered by steering wires (as described numerous times before), or both. The desired mutual orientation of the branches 358 and 360 can be retained by making at least the proximal portion of the spline elements 362 not round, thereby preventing relative rotation of the branches 358 and 360 within the sheath 370.

Figure 58:
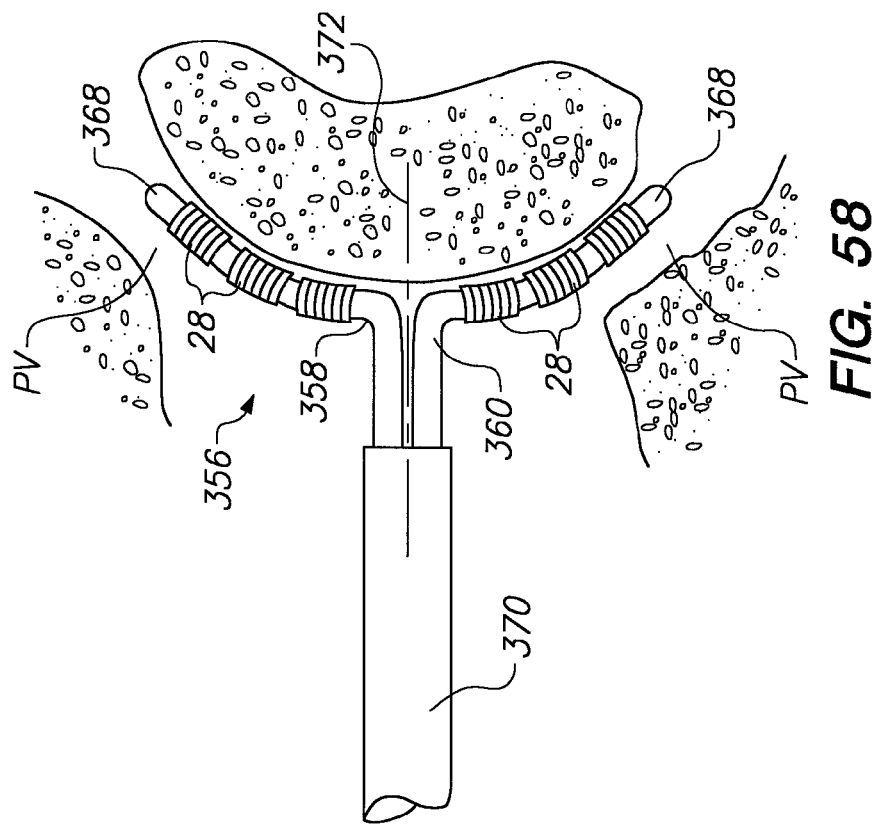
FIG. 58 is a side view of the spanning branch structure shown in FIG. 56, with the associated sheath retracted and the structure deployed in contact with tissue.

In use (see FIG. 58), each distal region 366 and 368 is intended to be individually maneuvered into spaced apart anchoring sites, e.g., the pulmonary veins (PV in FIG. 58). Once both regions 366 and 368 are suitably anchored, the operative branches 360 and 362 are advanced distally, toward the anchoring sites. The operative branches 360 and 362 bend inward, toward the sheath axis 372, to place the electrode elements 28 in contact with tissue spanning the anchoring sites.

Figure 59:
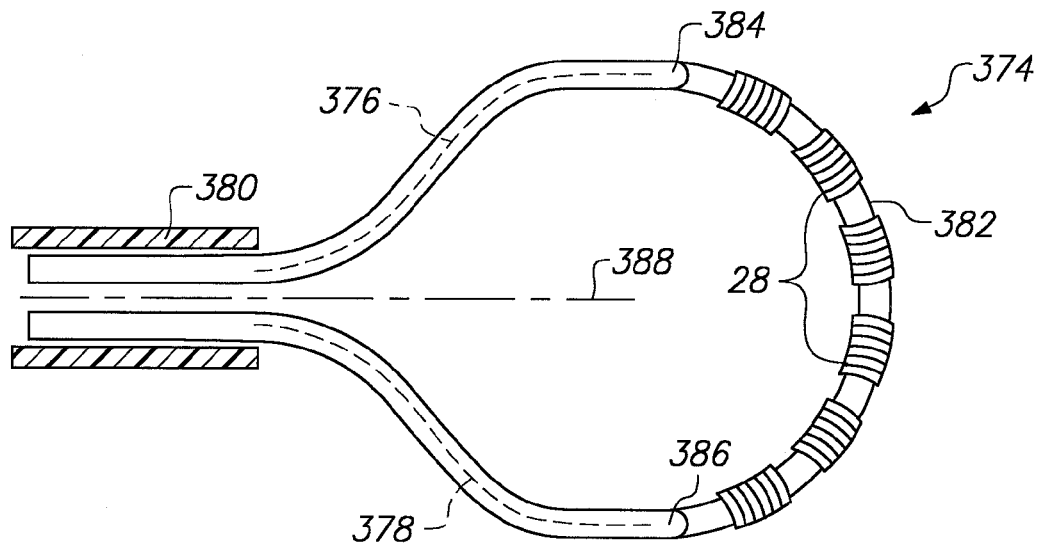
FIG. 59 is a side view of an alternative embodiment a spanning branch structure of the type shown in FIG. 56.

FIG. 59 shows an alternative embodiment of a self-anchoring structure 374. Like the structure 356 shown in FIG. 56, the structure 374 includes two branches 376 and 378, which are slidably carried within a sheath 380. When deployed outside the sheath 380, the distal ends 384 and 386 of the branches 376 and 378 are located in an outwardly bowed orientation relative to the axis 388 of the sheath 380. As earlier described in connection with the FIG. 45 embodiment, the branches 376 and 378 can be bent outwardly either by prestressing the associated interior spline elements 380, located in the branches 376 and 378, or providing active steering, or both.

In FIG. 59, a flexible element 382 spans the distal ends 484 and 386 of the branches 376 and 378. The flexible element 382 is made of material that is less rigid that the two branches 376 and 378. In the illustrated embodiment, the flexible element 382 is biased to assume a normally outwardly bowed shape, as FIG. 59 shows. The element 382 carries one or more operative elements, which can vary and which in the illustrated embodiment comprise electrode elements 28.

Figure 60:
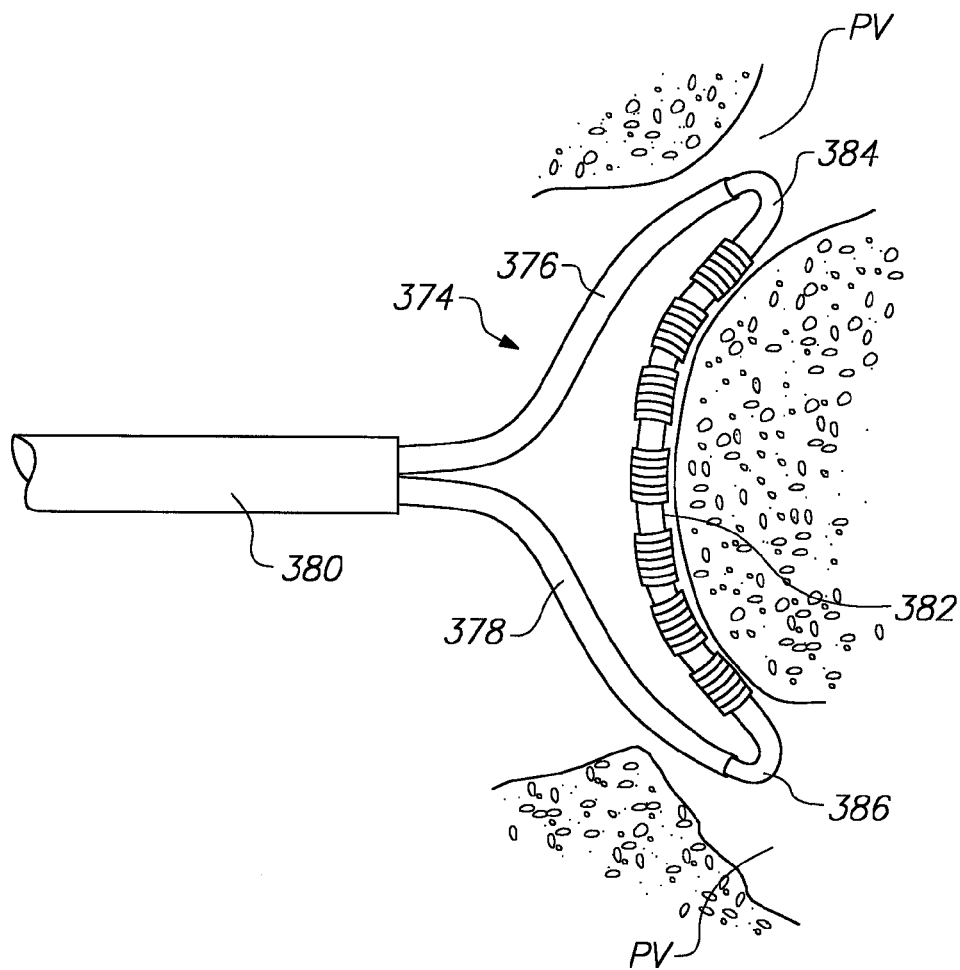
FIG. 60 is a side view of the spanning branch structure shown in FIG. 59 deployed in contact with tissue.

As FIG. 60 shows, in use, each distal region 384 and 386 is intended to be individually maneuvered into spaced apart anchoring sites, e.g., the pulmonary veins (PV in FIG. 60). When the regions 384 and 386 are suitably anchored, the spanning element 382 places the electrode elements 28 in contact with tissue spanning the anchoring sites. If the tissue region between the anchoring sites has a concave contour (and not a convex contour, as FIG. 60 shows), the outwardly bowed bias of the flexible element 382 will conform to the concave contour, just as it conforms to a convex contour.

4. Spring-Assisted Branch Structures

FIG. 61 shows another embodiment of a spring-assisted multiple electrode structure 390. The structure 390 includes two operative branches 392 and 394 carried at the distal end 16 of the catheter tube 12. The catheter tube 12 forms part of a probe 10, as shown in FIG. 1.

As previously described in connection with the embodiment shown in FIG. 56, each operative branch 392 and 394 comprises a spline element 396 enclosed within an electrically insulating sleeve 398. Operative elements, for example, electrode elements 28, are carried by the sleeve 398.

In the FIG. 61 embodiment, the spline elements 396 are preformed to move along the exterior of the distal catheter end 16 and then extend radially outward at an angle of less than 90°. The spline elements 396, prestressed in this condition, act as spring mechanisms for the operative branches 392 and 394. The prestressed spline elements 396 hold the branches 392 and 394 in a spaced apart condition (shown in FIG. 61), but resisting further or less radial separation of the branches 392 and 394.

A sheath 400 is slidable in a forward direction (arrow 402 in FIG. 62) along the catheter tube 12 to press against and close the radial spacing between the branches 392 and 394. This low profile geometry (shown in FIG. 62) allows introduction of the structure 390 into the selected body region. Rearward movement of the sheath 400 (arrow 404 in FIG. 61) frees the branches 392 and 394, which return due to the spring action of the spline elements 396 to a normally spaced apart condition (shown in FIG. 61).

The catheter tube 12 includes an interior lumen 406. As FIG. 61 shows, the lumen 406 accommodates passage of a guide wire 408 with a blunt distal end 410.

When deployed in an atrium (as FIG. 63A depicts) the distal end 410 of the guide wire 408 is maneuvered into a selected anchoring site (e.g., a pulmonary vein in the left atrium, or the inferior vena cava in the right atrium). The structure 390, enclosed within the sheath 400, is slid over the guide wire 408 to the targeted site (arrow 412 in FIG. 63A). As FIG. 63B shows, the sheath 400 is moved rearwardly (arrow 414 in FIG. 63B) to free the spring-like operative branches 392 and 394. Advancing the operative branches 392 and 394 along the guide wire 408 opens the radial spacing between the branches. The spring action of the spline elements 396 resisting this action exerts force against the tissue, assuring intimate contact between the electrode elements 28 and the tissue. The spline elements 396 can also be deployed within an atrium without use of a guide wire 408.

One or more spring-assisted spline elements 396 of the kind shown in FIG. 61 can also be deployed in a ventricle or in contact with the atrial septum for the purpose of making large lesions. As in the atrium, use of the guide wire 408 is optional. However, as shown in FIG. 63C, in these regions, a guide wire 408 can be used, which includes at its distal end a suitable positive tissue fixation element 542, e.g., a helical screw or vacuum port, to help stabilize the contact between the spline elements 396 and myocardial tissue. Several spline elements 396 can be arranged in a circumferentially spaced star pattern to cover a large surface area and thereby make possible the larger, deeper lesions believed to be beneficial in the treatment of ventricular tachycardia.

The spring action (i.e., spring constant) of the spline elements 396 can be varied, e.g., by changing the cross sectional area of the spline elements 396, or by making material composition or material processing changes.

5. Self-Anchoring Loop Structures

Figure 66:
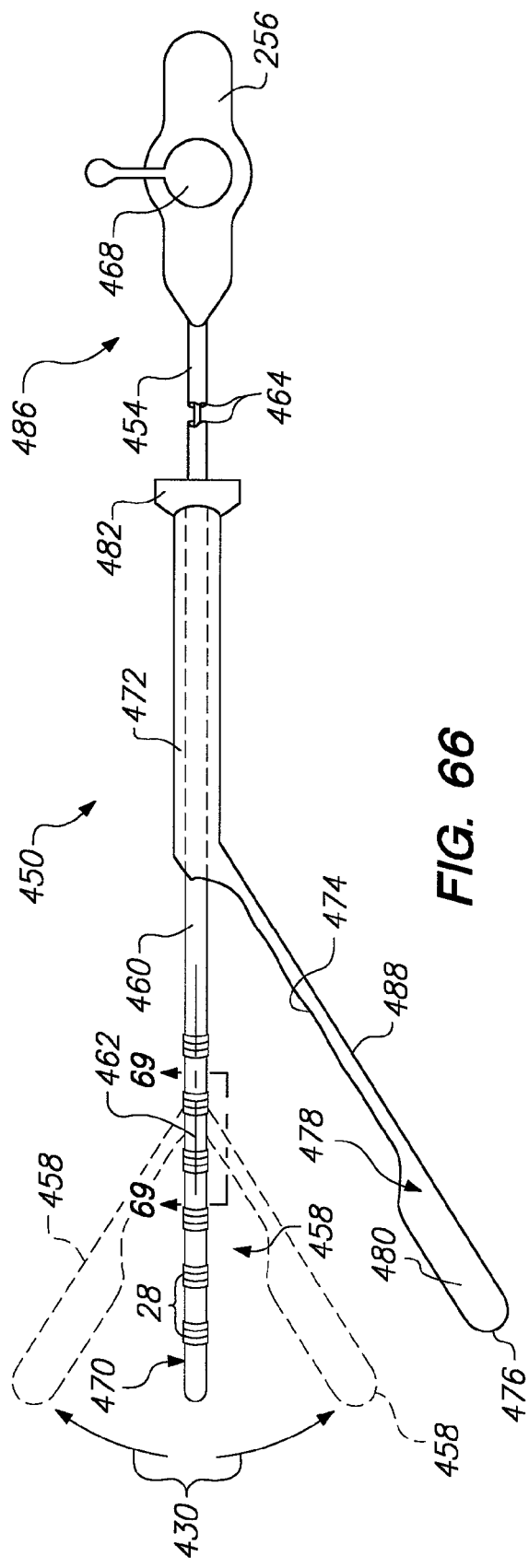
FIG. 66 is a side view of an alternative embodiment of a self-anchoring, loop structure, showing the catheter tube detached from the associated sheath.

FIG. 66 shows an assembly 450, which, in use, creates a self-anchoring loop structure 452 (which is shown in FIG. 68). The assembly 450 includes a catheter 486 comprising a flexible catheter tube 454 with a handle 256 on its proximal end, and which carries a multiple electrode array 458 on its distal end 470.

In the illustrated embodiment, the multiple electrode array 458 comprises electrode elements 28 attached to a sleeve 460 (see FIG. 69), which is made from an electrically insulating material, as already described.

As FIG. 69 best shows, a bendable spring 462 is carried within the sleeve 460 near the distal end 470 of the catheter tube 454. One or more steering wires 464 are attached to the spring 462 and pass through the catheter tube 454 to a steering controller 468 in the handle. While various steering mechanisms can be used, in the illustrated embodiment, the controller 468 comprises a rotatable cam wheel of the type shown in Lundquist and Thompson U.S. Pat. No. 5,254,088, which is already incorporated into this Specification by reference.

Operation of the steering controller 468 pulls on the steering wires 464 to apply bending forces to the spring 462. Bending of the spring 462 bends (arrows 490 in FIG. 66) the distal end 470 of the catheter tube 454 (shown in phantom lines), to deflect the multiple electrode array 458. As heretofore described, the catheter 486 can comprise a conventional steerable catheter.

The catheter tube 454 carries a sheath 472. The sheath 472 includes a proximal gripping surface 482 accessible to the physician. The sheath 472 also includes a closed distal end 476, and a slot 474, which is cut out proximal to the closed distal end 476. A region 480 of the sheath remains between the distal edge of the slot 474 and the closed distal catheter tube end 476. This region 480 peripherally surrounds an interior pocket 478.

Figure 67:
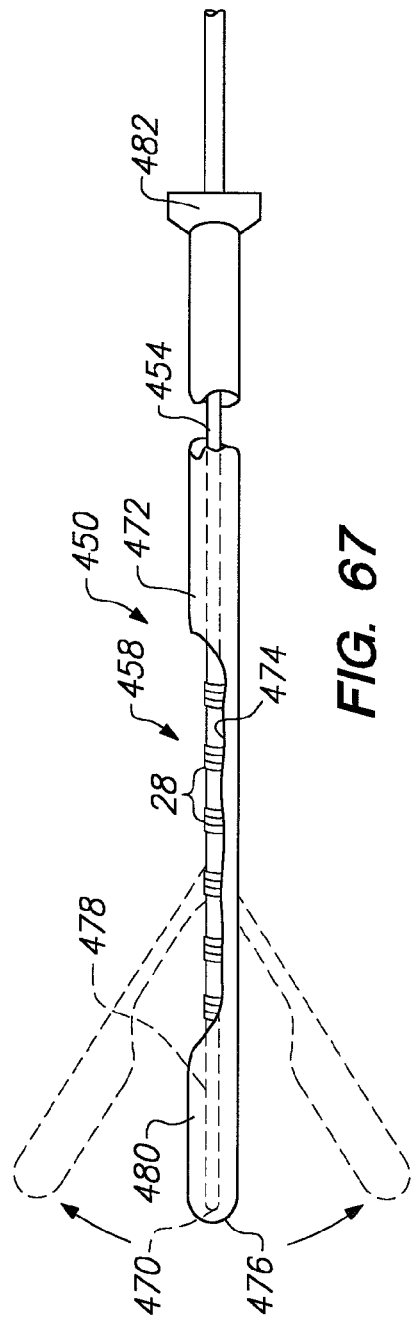
FIG. 67 is a side view of the self-anchoring, loop structure shown in FIG. 66, with the catheter tube attached to the associated sheath.

The catheter tube 12 is slidable within the sheath 472. When the distal end 470 occupies the slot 474, sliding the catheter tube 12 forward inserts the distal end 470 into the pocket 478, as FIG. 67 shows. The distal end 470 of the catheter tube 454 can be inserted into the pocket 478 either before introduction of the electrode array 458 into the targeted body region, or after introduction, when the electrode array 458 is present within the targeted body region. The pocket 478 is sized to snugly retain the inserted end 470 by friction or interference.

By holding the sheath 472 stationary and applying a rearward sliding force on the catheter tube 454, the physician is able to free the distal catheter tube end 470 from the pocket 478, as FIG. 66 shows. With the distal end 470 free of the pocket 478, the physician is able to slide the entire catheter tube 454 from the sheath 472, if desired, and insert a catheter tube of another catheter in its place.

Once the distal catheter tube end 470 is inserted into the pocket 478, the physician can form the loop structure 452. More particularly, by gripping the surface 482 to hold the sheath 472 stationary, the physician can slide the catheter tube 454 forward with respect to the sheath 472 (arrow 484 in FIG. 68). As FIG. 68 shows, advancement of the catheter tube 454 progressively pushes the multiple electrode array 458 outward through the slot 474. With the distal end 470 captured within the pocket 478, the pushed-out portion of the electrode array 458 bends and forms the loop structure 452.

In many respects, the loop structure 452 shown in FIG. 68 shares attributes with the loop structure 20, shown in FIG. 3A. The sheath region 488 underlying the slot 474 serves as a flexible joint for the loop structure 452, just as the flexible joint 44 does for the loop structure 20 in FIG. 3A. However, unlike the structure 20 in FIG. 3A, the physician is able to mate with the pocket 478 a catheter of his/her own choosing, since the pocket 478 allows easy insertion and removal of a catheter from the assembly 450. The physician is thereby given the opportunity to select among different catheter types and styles for use in forming the loop structure 452.

Figure 70:
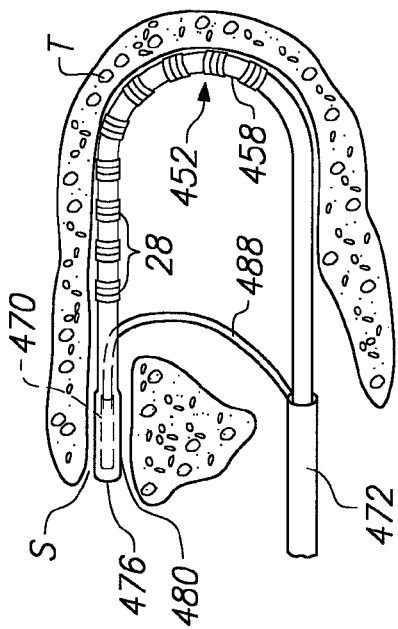
FIG. 70 is a side view of the self-anchoring, loop structure shown in FIG. 67, showing the structure deployed for use within a body cavity.

Furthermore, as FIG. 70 shows, the distal end 470 of the catheter tube 454, when retained within the pocket 478, can serve to establish contact with an anatomic structure S, while the loop structure 452 contacts nearby tissue T. As FIG. 67 shows, operation of the steering controller 468 serves to deflect the pocket region 480 of the sheath 472 along with the distal catheter tube end 470, to help maneuver and locate the sheath distal end 470 in association with the anatomic structure S. The distal end 470 of the catheter tube 454, retained within the pocket 478, can thereby serve to stabilize the position of the loop structure 452 in contact with tissue T during use.

The stiffness of the sheath 472 and the length of the flexible joint region 488 are selected to provide mechanical properties to anchor the loop structure 452 during use. Generally speaking, the sheath 472 is made from a material having a greater inherent stiffness (i.e., greater durometer) than the structure 452 itself. The selected material for the sheath 472 can also be lubricious, to reduce friction during relative movement of the catheter tube 454 within the sheath 472. For example, materials made from polytetrafluoroethylene (PTFE) can be used for the sheath 452. The geometry of the loop structure 452 can be altered by varying the stiffness of the sheath 472, or varying the stiffness or the length of the flexible joint 488, or one or more of these at the same time.

Figure 71:
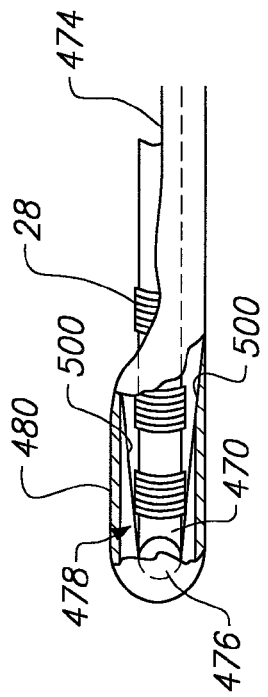
FIG. 71 is a side view, with parts broken away and in section, of an alternative embodiment of the self-anchoring, loop structure shown in FIG. 67, with an interference fit releasably coupling the catheter tube to the associated sheath.
Figure 72:
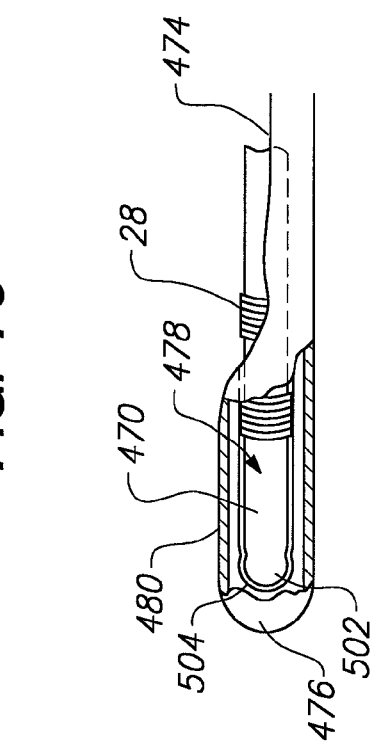
FIG. 72 is a side view, with parts broken away and in section, of an alternative embodiment of the self-anchoring, loop structure shown in FIG. 67, with a releasable snap-fit coupling the catheter tube to the associated sheath.

There are various ways to enhance the releasable retention force between the distal catheter tube end 470 and the pocket 478. For example, FIG. 71 shows a sheath 472 having a pocket region 480 in which the interior walls 500 of the pocket 478 are tapered to provide a releasable interference fit about the distal catheter tube end 470. As another example, FIG. 72 shows a distal catheter tube end 470, which includes a ball-nose fixture 502 which makes releasable, snap-fit engagement with a mating cylindrical receiver 504 formed in the pocket 478. By providing active attachment mechanisms within the pocket 478, the effective length of the pocket region 480 can be reduced. These preformed regions can be formed by thermal molding.

Figure 73:
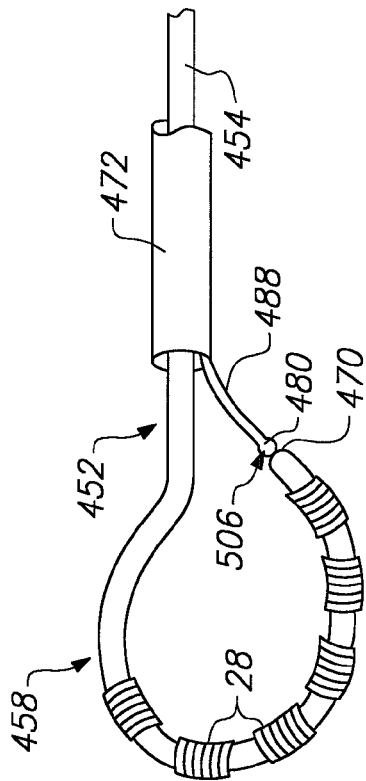
FIG. 73 is a side view of an alternative embodiment of the self-anchoring, loop structure shown in FIG. 67, with a pivoting connection releasably coupling the catheter tube to the associated sheath.

FIG. 73 shows a modification of the self-anchoring loop structure 452 shown in FIG. 68, in which the distal end 470 of the catheter tube 454 forms a pivoting junction 506 with the pocket region 480 of the sheath 472. FIGS. 74 and 75 show the details of one embodiment of the pivoting junction 506.

As FIG. 74 shows, the pocket region 480 includes an axial groove 508 that opens into the pocket 478. The distal end 470 of the catheter tube includes a ball joint 510. As FIG. 75 shows, forward sliding movement of the catheter tube 454 advances the distal end 470, including the ball joint 510, into the pocket 478. As FIG. 76 shows, as further advancement of the catheter tube 454 progressively pushes the multiple electrode array 458 outward through the slot 474, the ball joint 510 enters the groove 508. The ball joint 510 pivots within the groove 508, thereby forming the pivoting junction 506. The junction 506 allows the distal end 470 to swing with respect to the pocket region 480 (arrows 512 in FIG. 76), as the pushed-out portion of the electrode array 458 bends and forms the loop structure 452, shown in FIG. 73.

FIGS. 77A to 77D show another embodiment of the pivoting junction 506. In this embodiment, a separately cast plastic or metal cap 514 is attached to the end of the sheath 472. The cap 514 includes an interior cavity forming the pocket 478. Unlike the previously described embodiments, the pocket 478 in the cap 514 includes an interior wall 516 (see FIG. 77D), which is closed except for a slotted keyway 518.

The cap 514 includes the previously described groove 508. Unlike the previous embodiments, the groove 508 extends to and joins the slotted keyway 518 (see FIG. 77A). The groove 508 also extends through the distal end 520 of the cap 514 to an opening 522 (see FIG. 77B) on the side of the cap 514 that faces away from the sheath slot 474. As FIG. 77B shows, the opening 522 accommodates passage of the ball joint 510 carried at the distal end 470 of the catheter tube 454. Advancing the ball joint 510 from the opening 522 along the groove 508 locks the ball joint 510 within the pocket 478. Further advancement brings the ball joint 510 to rest within the slotted keyway 518 (see FIG. 77C). The slotted keyway 518 retains the ball joint 510, securing the distal catheter tube end 470 to the cap 514. The interference between the ball joint 510 and the keyway 518 prevents separation of the distal catheter tube end 470 from the sheath 472 by sliding axial movement of the catheter tube 545 within the sheath 472. However, as FIG. 77D shows, the ball joint 510 pivots within the groove 508 of the cap 514, thereby forming the pivoting junction 506, to allow the distal end 470 to swing with respect to the pocket region 478.

The distal catheter tube end 470 is separated from the cap 514 by sliding the ball joint 510 along the groove 508 into the opening 522. The ball joint 510 passes through the opening 522, thereby releasing the catheter tube 454 from the sheath 472.

FIGS. 78A to 78C show another embodiment of the pivoting junction 506. In this embodiment, like FIGS. 77A to 77D, a separately cast plastic or metal cap 606 is attached to the end of the sheath 472. The cap 606 includes an interior cavity forming the pocket 608. As FIG. 78A shows, the pocket 608 receives the ball joint 510 (carried by the distal loop structure end 470) through the sheath end 612 of the cap 606, in the manner previously described and shown with reference to FIG. 76.

As FIGS. 78B and 78C show, the ball joint 510 pivots within the pocket 608 through a groove 610 formed in the cap 514. The pivoting junction 506 is thereby formed, which allows the distal end 470 to swing with respect to the cap 606.

6. Deployment and Use of Self-Anchoring Multiple Electrode Structures

1. Left Atrium

The self-anchoring multiple electrode structures described above can be deployed into the left atrium to create lesions between the pulmonary veins and the mitral valve annulus. Tissue nearby these anatomic structures are recognized to develop arrhythmia substrates causing atrial fibrillation. Lesions in these tissue regions block reentry paths or destroy active pacemaker sites, and thereby prevent the arrhythmia from occurring.

Figure 79:
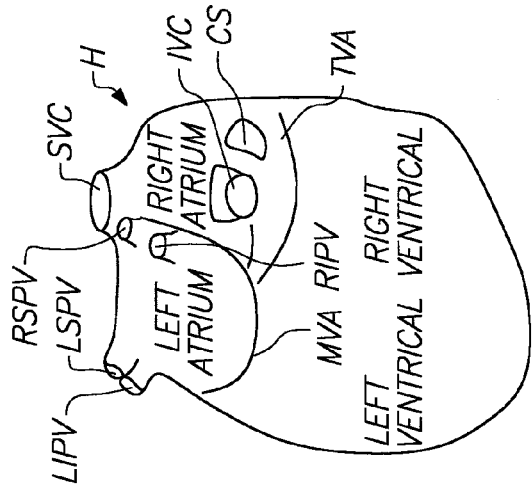
FIG. 79 shows, in diagrammatic form, sites for anchoring a self-anchoring structure within the left or right atria.

FIG. 79 shows (from outside the heart H) the location of the major anatomic landmarks for lesion formation in the left atrium. The landmarks include the right inferior pulmonary vein (RIPV), the right superior pulmonary vein (RSPV), the left superior pulmonary vein (LSPV), the left inferior pulmonary vein (LIPV); and the mitral valve annulus (MVA). FIG.

Figure 80C:
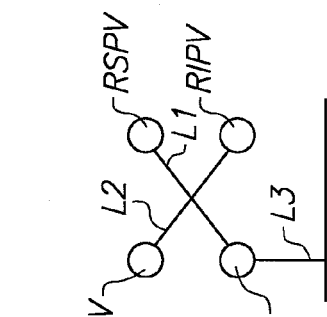
FIGS. 80A to 80D show representative lesion patterns in the left atrium, which rely, at least in part, upon anchoring a structure with respect to a pulmonary vein.
Figure 80B:
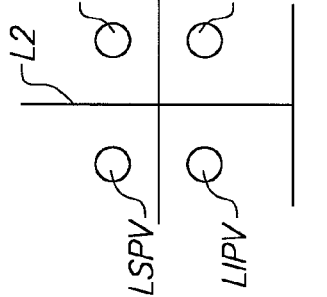
Figure 80A:
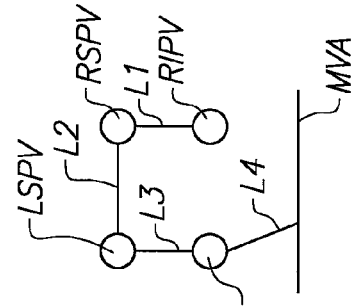
Figure 80D:
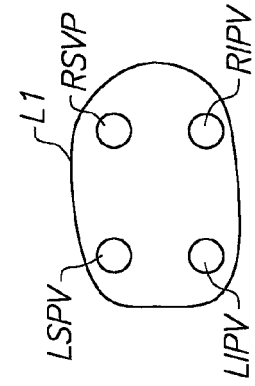

80A to FIG. 80D show representative lesion patterns formed inside the left atrium based upon these landmarks.

In FIG. 80A, the lesion pattern comprises a first leg L1 between the right inferior pulmonary vein (RIPV) and the right superior pulmonary vein (RSPV); a second leg L2 between the RSPV and the left superior pulmonary vein (LSPV); a third leg L3 between the left superior pulmonary vein (LSPV) and the left inferior pulmonary vein (LIPV); and a fourth leg L4 leading between the LIPV and the mitral valve annulus (MVA).

FIG. 80B shows an intersecting lesion pattern comprising horizontal leg L1 extending between the RSPV-LSPV on one side and the RIPV-LIPV on the other size, intersected by vertical leg L2 extending between the RSPV-RIPV on one side and the LSPV-LIPV on the other side. The second leg L2 also extends to the MVA.

FIG. 80C shows a criss-crossing lesion pattern comprising a first leg extending between the RSPV and LIPV; a second leg L2 extending between the LSPV and RIPV; and a third leg L3 extending from the LIPV to the MVA.

FIG. 80D shows a circular lesion pattern comprising a leg L1 that extends from the LSPV, and encircles to RSPV, RIPV, and LIPV, leading back to the LSPV.

The linear lesion patterns shown in FIGS. 80A, 80B, and 80C can be formed, e.g., using the structure 272 shown in FIGS. 45 and 46, by placing the anchoring branch 276 in a selected one of the pulmonary veins to stabilize the position of the operative branch 274, and then maneuvering the operative branch 274 to sequentially locate it along the desired legs of the lesion pattern. It may be necessary to relocate the anchoring branch 276 in a different pulmonary vein to facilitate maneuvering of the operative branch 274 to establish all legs of the pattern. The branched structures 356 (FIG. 56) or 374 (FIG. 59) can also be used sequentially for the same purpose, in the manner shown in FIG. 58 (for structure 356) and FIG. 60 (for structure 374).

The circular lesion pattern shown in FIG. 80D can be formed, e.g., using an anchored loop structure 458 as shown in FIG. 68 or 73. Using these structures, the distal end 470 of the catheter tube 454 (enclosed within the pocket 478) is located within a selected one of the pulmonary veins (the LSPV in FIG. 80D), and the loop structure is advanced from the sheath 472 to circumscribe the remaining pulmonary veins. As with other loop structures, the loop structure tend to seek the largest diameter and occupy it. Most of the structures are suitable for being torqued or rotated into other planes and thereby occupy smaller regions. The anchored loop structure 458 is also suited for forming lesion legs that extend from the inferior pulmonary veins to the mitral valve annulus (for example, L4 in FIG. 80A and L3 in FIG. 80C).

Figure 44:
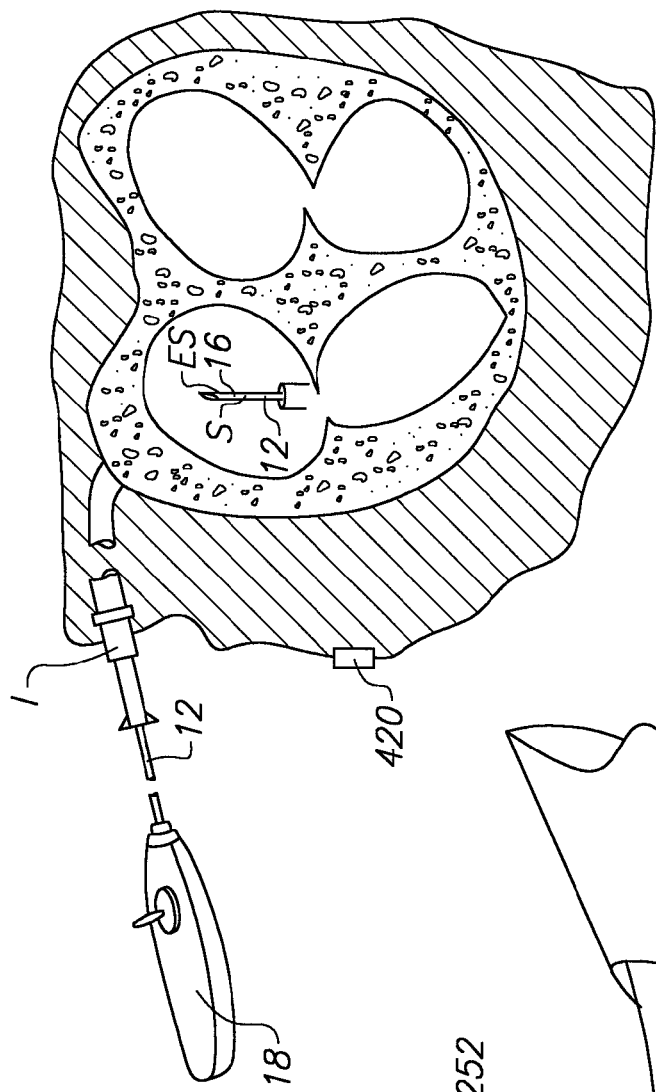
FIG. 44 is a largely diagrammatic view of the deployment of the distal region of the probe shown in FIG. 1 in the right atrium of a heart.

To access the left atrium, any of these structures can be introduced in the manner shown in FIG. 44 through the inferior vena cava (IVC) into the right atrium, and then into the left atrium through a conventional transeptal approach. Alternatively, a retrograde approach can be employed through the aorta into the left ventricle, and then through the mitral valve into the left atrium.

2. Right Atrium

FIG. 79 shows (from outside the heart H) the location of the major anatomic landmarks for lesion formation in the right atrium. These landmarks include the superior vena cava (SVC), the tricuspid valve annulus (TVA), the inferior vena cava (IVC), and the coronary sinus (CS). Tissue nearby these anatomic structures have been identified as developing arrhythmia substrates causing atrial fibrillation. Lesions in these tissue regions block reentry paths or destroy active pacemaker sites and thereby prevent the arrhythmia from occurring.

Figure 81C:
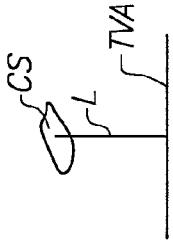
FIGS. 81A to 81C show representative lesion patterns in the right atrium, which rely, at least in part, upon anchoring a structure with respect to the superior vena cava, the inferior vena cava, or the coronary sinus.
Figure 81B:
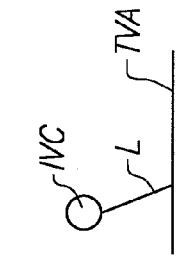
Figure 81A:

FIGS. 81A to 81C show representative lesion patterns formed inside the right atrium based upon these landmarks.

FIG. 81A shows a representative lesion pattern L that extends between the superior vena cava (SVC) and the tricuspid valve annulus (TVA). FIG. 81B shows a representative lesion pattern that extends between the interior vena cava (IVC) and the TVA. FIG. 81C shows a representative lesion pattern L that extends between the coronary sinus (CS) and the tricuspid valve annulus (TVA).

The self-anchoring multiple electrode structures described above can be deployed into the right atrium to create these lesions. For example, the structure 272 shown in FIGS. 45 and 46 can be used, by placing the anchoring branch 276 in the SVC or IVC to stabilize the position of the operative branch 274, and then maneuvering the operative branch 274 to locate it along the desired path of the lesion pattern. The branched structures 356 (FIG. 56) or 374 (FIG. 59) can also be used sequentially for the same purpose, in the manner shown in FIG. 58 (for structure 356) and FIG. 60 (for structure 374).

Any of these structures can be introduced in the manner shown in FIG. 44 through the inferior vena cava (IVC) into the right atrium.

3. Epicardial Use

Many of the structures suited for intracardiac deployment, as discussed above, can be directly applied to the epicardium through conventional thoracotomy or thoracostomy techniques. For example, the structures shown in FIGS. 56, 59, 61, 66, and 73 are well suited for epicardial application.

III. Flexible Electrode Structures

A. Spacing of Electrode Elements

In the illustrated embodiment, the size and spacing of the electrode elements 28 on the various structures can vary.

1. Long Lesion Patterns

For example, the electrode elements 28 can be spaced and sized for creating continuous, long lesion patterns in tissue, as exemplified by the lesion pattern 418 in tissue T shown in FIG. 64. Long, continuous lesion patterns 418 are beneficial to the treatment of atrial fibrillation. The patterns 418 are formed due to additive heating effects, which cause the lesion patterns 418 to span adjacent, spaced apart electrode 28, creating the desired elongated, long geometry, as FIG. 64 shows.

The additive heating effects occur when the electrode elements 28 are operated simultaneously in a bipolar mode between electrode elements 28. Furthermore, the additive heating effects also arise when the electrode elements 28 are operated simultaneously in a unipolar mode, transmitting energy to an indifferent electrode 420 (shown in FIG. 44).

More particularly, when the spacing between the electrodes 28 is equal to or less than about 3 times the smallest of the diameters of the electrodes 28, the simultaneous emission of energy by the electrodes 28, either bipolar between the segments or unipolar to the indifferent electrode 420, creates an elongated continuous lesion pattern 58 in the contacted tissue area due to the additive heating effects.

Alternatively, when the spacing between the electrodes along the contacted tissue area is equal to or less than about 2 times the longest of the lengths of the electrodes 28, the simultaneous application of energy by the electrodes 28, either bipolar between electrodes 28 or unipolar to the indifferent electrode 420, also creates an elongated continuous lesion pattern 58 in the contacted tissue area due to additive heating effects.

Further details of the formation of continuous, long lesion patterns are found in copending U.S. patent application Ser. No. 08/287,192, filed Aug. 8, 1994, entitled "Systems and Methods for Forming Elongated Lesion Patterns in Body Tissue Using Straight or Curvilinear Electrode Elements," which is incorporated herein by reference.

Alternatively, long continuous lesion patterns, like that shown in FIG. 64, can be achieved using an elongated electrode element made from a porous material. By way of illustration, FIG. 82 shows a loop electrode structure 424, like that shown in FIG. 2A. The structure 424 includes an electrode body 428, which includes a porous material 430 to transfer ablation energy by ionic transport.

As FIG. 82 shows, the distal end 426 of the electrode body 428 is coupled to a flexible joint 440, which is part of the slotted sheath 442, as previously described in connection with FIG. 3A. Advancement of the electrode body 428 from the slotted sheath 442 creates the loop structure 424, in the same manner that the loops structure 20 shown in FIG. 3A is formed.

As best shown in FIG. 83, the electrode body 428 includes a center support lumen 432 enveloped by the porous material 430. The lumen 432 carries spaced-apart electrodes 429 along its length. The lumen 432 also includes spaced-apart apertures 434 along its length.

The lumen 432 includes a proximal end 430, which communicates with a source of ionic fluid 438. The lumen 432 conveys the ionic fluid 438. The ionic fluid 438 passes through the apertures 434 and fills the space between the lumen 432 and the surrounding porous material 430. The fluid 438 also serves to expand the diameter of the structure 424. The structure 424 therefore possesses a low profile geometry, when no liquid 438 is present, for introduction within the targeted body region enclosed within the slotted sheath 442. Once advanced from the sheath 442 and formed into the loop structure 424, fluid 438 can be introduced to expand the structure 424 for use.

The porous material 430 has pores capable of allowing transport of ions contained in the fluid 438 through the material 430 and into contact with tissue. As FIG. 83 also shows, the electrodes 429 are coupled to a source 444 of radio frequency energy. The electrodes 429 transmit the radio frequency energy into the ionic fluid 438. The ionic (and, therefore, electrically conductive) fluid 438 establishes an electrically conductive path. The pores of the porous material 430 establish ionic transport of ablation energy from the electrodes 429, through the fluid 438, liquid, to tissue outside the electrode body 428.

Preferably, the fluid 438 possesses a low resistivity to decrease ohmic loses, and thus ohmic heating effects, within the body 428. The composition of the electrically conductive fluid 438 can vary. In the illustrated embodiment, the fluid 438 comprises a hypertonic saline solution, having a sodium chloride concentration at or near saturation, which is about 5% to about 25% weight by volume. Hypertonic saline solution has a low resistivity of only about 5 ohm·cm, compared to blood resistivity of about 150 ohm·cm and myocardial tissue resistivity of about 500 ohm·cm.

Alternatively, the composition of the electrically conductive fluid 438 can comprise a hypertonic potassium chloride solution. This medium, while promoting the desired ionic transfer, requires closer monitoring of the rate at which ionic transport occurs through the pores of the material 430, to prevent potassium overload. When hypertonic potassium chloride solution is used, it is preferred to keep the ionic transport rate below about 10 mEq/min.

Regenerated cellulose membrane materials, typically used for blood oxygenation, dialysis, or ultrafiltration, can be used as the porous material 430. Regenerated cellulose is electrically non-conductive; however, the pores of this material (typically having a diameter smaller than about 0.1 µm) allow effective ionic transport in response to the applied RF field. At the same time, the relatively small pores prevent transfer of macromolecules through the material 430, so that pressure driven liquid perfusion is less likely to accompany the ionic transport, unless relatively high pressure conditions develop within the body 428.

Other porous materials can be used as the porous material 430. Candidate materials having pore sizes larger than regenerated cellulous material, such as nylon, polycarbonate, polyvinylidene fluoride (PTFE), polyethersulfone, modified acrylic copolymers, and cellulose acetate, are typically used for blood microfiltration and oxygenation. Porous or microporous materials may also be fabricated by weaving a material (such as nylon, polyester, polyethylene, polypropylene, fluorocarbon, fine diameter stainless steel, or other fiber) into a mesh having the desired pore size and porosity. These materials permit effective passage of ions in response to the applied RF field. However, as many of these materials possess larger pore diameters, pressure driven liquid perfusion, and the attendant transport of macromolecules through the pores, are also more likely to occur at normal inflation pressures for the body 428. Considerations of overall porosity, perfusion rates, and lodgment of blood cells within the pores of the body 128 must be taken more into account as pore size increase.

Low or essentially no liquid perfusion through the porous body 428 is preferred. Limited or essentially no liquid perfusion through the porous body 428 is beneficial for several reasons. First, it limits salt or water overloading, caused by transport of the hypertonic solution into the blood pool. This is especially true, should the hypertonic solution include potassium chloride, as observed above. Furthermore, limited or essentially no liquid perfusion through the porous body 428 allows ionic transport to occur without disruption. When undisturbed by attendant liquid perfusion, ionic transport creates a continuous virtual electrode at the electrode body-tissue interface. The virtual electrode efficiently transfers RF energy without need for an electrically conductive metal surface.

FIGS. 84 and 85 show an embodiment of the porous electrode body 428 which includes spaced-apart external rings 446, which form porous electrode segments. It is believed that, as the expanded dimension of the body 428 approaches the dimension of the interior electrodes 429, the need to segment the electrode body 428 diminishes.

Alternatively, as FIG. 86 shows, instead of a lumen 432 within the body 438, a foam cylinder 448 coupled in communication with the ionic fluid 438 could be used to carry the electrodes 429 and perfuse the ionic fluid 438.

2. Interrupted Lesion Patterns

The electrode elements 28 can be sized and spaced to form interrupted, or segmented lesion patterns, as exemplified by the lesion pattern 422 in tissue T shown in FIG. 65. Alternatively, spaced-apart electrode elements 28 capable of providing long lesion patterns 418 can be operated with some electrode elements 28 energized and others not, to provide an interrupted lesion pattern 422, as FIG. 65 exemplifies.

When the spacing between the electrodes 28 is greater than about 5 times the smallest of the diameters of the electrodes 28, the simultaneous emission of energy by the electrodes 28, either bipolar between segments or unipolar to the indifferent electrode 420, does not generate additive heating effects. Instead, the simultaneous emission of energy by the electrodes 28 creates an elongated segmented, or interrupted, lesion pattern in the contacted tissue area.

Alternatively, when the spacing between the electrodes 28 along the contacted tissue area is greater than about 3 times the longest of the lengths of the electrodes 28, the simultaneous application of energy, either bipolar between electrodes 28 or unipolar to the indifferent electrode 420, creates an elongated segmented, or interrupted, lesion pattern.

3. Flexibility

When the electrode elements 28 are flexible, each element 28 can be as long as 50 mm. Thus, if desired, a single coil electrode element 28 can extend uninterrupted along the entire length of the support structure. However, a segmented pattern of spaced apart, shorter electrode elements 28 is preferred.

If rigid electrode elements 28 are used, the length of the each electrode segment can vary from about 2 mm to about 10 mm. Using multiple rigid electrode elements 28 longer than about 10 mm each adversely effects the overall flexibility of the element. Generally speaking, adjacent electrode elements 28 having lengths of less than about 2 mm do not consistently form the desired continuous lesion patterns.

4. Temperature Sensing

As FIG. 3A shows, each electrode element 28 can carry at least one and, preferably, at least two, temperature sensing elements 540. The multiple temperature sensing elements 540 measure temperatures along the length of the electrode element 28. The temperature sensing elements 540 can comprise thermistors or thermocouples. If thermocouples are used, a cold junction 24 (see FIG. 3A) can be carried on the same structure as the electrode elements 28.

An external temperature processing element (not shown) receives and analyses the signals from the multiple temperature sensing elements 540 in prescribed ways to govern the application of ablating energy to the electrode element 28. The ablating energy is applied to maintain generally uniform temperature conditions along the length of the element 28.

Further details of the use of multiple temperature sensing elements in tissue ablation can be found in copending U.S. patent application Ser. No. 08/286,930, filed Aug. 8, 1994, entitled "Systems and Methods for Controlling Tissue Ablation Using Multiple Temperature Sensing Elements."

Various features of the invention are set forth in the following claims.

The invention claimed is:

1. An apparatus for performing a diagnostic or therapeutic operation on tissue between first and second pulmonary veins having a distance therebetween, the apparatus comprising:
 a probe including a catheter body and a first portion sized and shaped for insertion into the first pulmonary vein, a second portion sized and shaped for insertion into the second pulmonary vein, and a third portion located between the first and second portions and defining a length that substantially corresponds to the distance between the first and second pulmonary veins and defining a shape, a flexibility and a relationship with the first and second portions that results in at least the substantial majority of the third portion being in contact with the tissue between the first and second pulmonary veins when the first and second portions are inserted into the first and second pulmonary veins; and
 at least one operative element carried by the third portion.

2. An apparatus as claimed in claim 1, wherein the at least one operative element comprises an energy transmission device.

3. An apparatus as claimed in claim 1, wherein the at least one operative element comprises an electrode.

4. An apparatus as claimed in claim 1, wherein the first portion comprises a first branch, the second portion comprises a second branch, and the third portion comprises respective portions of the first and second branches.

5. An apparatus as claimed in claim 4, wherein the first branch includes a first spline and the second branch includes a second spline.

6. An apparatus as claimed in claim 1, wherein the first portion comprises a first branch, the second portion comprises a second branch, and the third portion comprises a spanning element that extends from the first branch to the second branch.

7. An apparatus as claimed in claim 6, wherein the first branch, second branch, and spanning element define respective flexibilities and the spanning element is more flexible that the first and second branches.

8. An apparatus as claimed in claim 6, wherein the first branch includes a first spline and the second branch includes a second spline.

9. An apparatus for performing a diagnostic or therapeutic operation on tissue between first and second pulmonary veins having a distance therebetween, the apparatus comprising:
 a probe including a catheter body and a first portion sized and shaped for insertion into the first pulmonary vein, a second portion sized and shaped for insertion into the second pulmonary vein, and a third portion located between the first and second portions and defining a length that substantially corresponds to the distance between the first and second pulmonary veins; and
 a plurality of energy transmission devices carried by the third portion.

10. An apparatus as claimed in claim 9, wherein the plurality of energy transmission devices comprises a plurality of electrodes.

11. An apparatus as claimed in claim 9, wherein the first portion comprises a first branch, the second portion comprises a second branch, and the third portion comprises respective portions of the first and second branches.

12. An apparatus as claimed in claim 11, wherein the first branch includes a first spline and the second branch includes a second spline.

13. An apparatus as claimed in claim 9, wherein the first portion comprises a first branch, the second portion comprises a second branch, and the third portion comprises a spanning element that extends from the first branch to the second branch.

14. An apparatus as claimed in claim 13, wherein the first branch, second branch, and spanning element define respective flexibilities and the spanning element is more flexible that the first and second branches.

15. An apparatus as claimed in claim 13, wherein the first branch includes a first spline and the second branch includes a second spline.

16. An apparatus for performing a diagnostic or therapeutic operation on tissue located between first and second pulmonary veins, the apparatus comprising:
 a catheter body defining a distal region;
 a plurality of energy transmission devices; and
 anchoring means, associated with the distal region of the catheter body, for entering the first and second pulmonary veins and anchoring the plurality of energy transmission devices adjacent to the tissue located between the first and second pulmonary veins.

17. An apparatus as claimed in claim 16, wherein the plurality of energy transmission devices comprises a plurality of electrodes.

* * * * *